US010004656B2

(12) United States Patent
Whalen et al.

(10) Patent No.: US 10,004,656 B2
(45) Date of Patent: Jun. 26, 2018

(54) SYSTEMS, METHODS AND APPARATUS FOR DIFFERENTIAL AIR PRESSURE DEVICES

(71) Applicant: AlterG, Inc., Fremont, CA (US)

(72) Inventors: Sean Tremaine Whalen, Mountain View, CA (US); Mark A. Shughart, Palo Alto, CA (US); Douglas Frank Schwandt, Palo Alto, CA (US); Robert Tremaine Whalen, Los Altos, CA (US); Edward Liou, Los Altos, CA (US); Fritz Moore, Vacaville, CA (US)

(73) Assignee: AlterG, Inc., Fremont, CA (US)

( * ) Notice: Subject to any disclaimer, the term of this patent is extended or adjusted under 35 U.S.C. 154(b) by 0 days. days.

(21) Appl. No.: 15/143,351

(22) Filed: Apr. 29, 2016

(65) Prior Publication Data

US 2016/0242993 A1    Aug. 25, 2016

Related U.S. Application Data

(63) Continuation of application No. 12/761,316, filed on Apr. 15, 2010, now abandoned, which is a
(Continued)

(51) Int. Cl.
*A61H 9/00* (2006.01)
*A63B 21/00* (2006.01)
(Continued)

(52) U.S. Cl.
CPC ......... *A61H 9/00* (2013.01); *A63B 21/00181* (2013.01); *A63B 22/02* (2013.01);
(Continued)

(58) Field of Classification Search
CPC .......... A61H 1/006; A61H 1/008; A61H 9/00; A61H 9/005; A61H 2009/0035;
(Continued)

(56) References Cited

U.S. PATENT DOCUMENTS 44,198 A    9/1864  Jones
54,530 A    5/1866  Hadfield
(Continued)

FOREIGN PATENT DOCUMENTS

CN    2034152 U    3/1989
CN    2208414 Y    9/1995
(Continued)

OTHER PUBLICATIONS

"Feedback Control System.," The Encyclopedia Americana International Edition; pp. 82-84; Dec. 2003.
(Continued)

*Primary Examiner* — Colin W Stuart
(74) *Attorney, Agent, or Firm* — Shay Glenn LLP

(57) ABSTRACT

Described herein are various embodiments of differential air pressure systems and components for differential air pressure systems. The air pressure systems have a chamber for receiving at least a portion of a user's body. Pressure in the chamber can be changed to adjust force on the user's body. Described herein are various methods and related structures for sealing a user into a pressurizable chamber. Also described herein are various methods and related structures for changing the shape and/or height of the chamber. Described herein are various types and configurations of chambers and support structures for chambers. Also described herein are various methods and related systems for treating various conditions using the differential air pressure systems, including but not limited to obesity, cardiac disease, multiple sclerosis, cerebral palsy, or Down Syndrome.

20 Claims, 49 Drawing Sheets

Related U.S. Application Data continuation of application No. PCT/US2008/011832, filed on Oct. 12, 2008.

(60) Provisional application No. 60/999,102, filed on Oct. 15, 2007, provisional application No. 60/999,101, filed on Oct. 15, 2007, provisional application No. 60/999,061, filed on Oct. 15, 2007, provisional application No. 60/999,060, filed on Oct. 15, 2007.

(51) Int. Cl.

| | |
|---|---|
| *A63B 22/02* | (2006.01) |
| *A61F 7/02* | (2006.01) |
| *A63B 22/00* | (2006.01) |
| *A63B 22/06* | (2006.01) |
| *A63B 22/18* | (2006.01) |
| *A63B 71/00* | (2006.01) |

(52) U.S. Cl.
CPC .......... *A61F 2007/0239* (2013.01); *A61H 2009/0035* (2013.01); *A61H 2201/5058* (2013.01); *A63B 22/0023* (2013.01); *A63B 22/0056* (2013.01); *A63B 22/0076* (2013.01); *A63B 22/0605* (2013.01); *A63B 22/18* (2013.01); *A63B 2022/002* (2013.01); *A63B 2071/0072* (2013.01); *A63B 2208/0204* (2013.01); *A63B 2208/0228* (2013.01); *A63B 2208/0242* (2013.01); *A63B 2208/053* (2013.01); *A63B 2209/10* (2013.01); *A63B 2220/20* (2013.01); *A63B 2220/40* (2013.01); *A63B 2220/805* (2013.01); *A63B 2230/01* (2013.01); *A63B 2230/06* (2013.01); *A63B 2230/062* (2013.01); *A63B 2230/30* (2013.01)

(58) Field of Classification Search
CPC .......... A61F 2007/0239; A61G 10/00; A61G 10/005; A61G 10/02; A61G 10/023; A61G 10/026; A63B 21/00181; A63B 2208/05; A63B 2208/053; A63B 2208/056
USPC .............. 601/5–11, 23; 128/202.12, 205.26; 482/54; 600/19
See application file for complete search history.

(56) References Cited

U.S. PATENT DOCUMENTS

| | | | |
|---|---|---|---|
| 60,883 A | 1/1867 | Hadfield | |
| 72,631 A | 12/1867 | Hadfield | |
| 100,867 A | 3/1870 | Curran | |
| 871,074 A | 11/1907 | Stockton | |
| 1,336,774 A | 4/1920 | Cooper | |
| 1,504,166 A | 8/1924 | Thornley | |
| 2,785,004 A | 3/1957 | Cooper | |
| 3,165,314 A | 1/1965 | Clearman et al. | |
| 3,176,793 A | 4/1965 | Roland | |
| 3,332,176 A | 7/1967 | Knetzer | |
| 3,335,529 A | 8/1967 | Gedney | |
| 3,353,309 A | 11/1967 | Kwake | |
| 3,428,015 A | 2/1969 | Cloud | |
| 3,768,467 A | 10/1973 | Jennings | |
| 3,911,913 A | 10/1975 | June | |
| 4,149,712 A | 4/1979 | Murphy | |
| 4,257,407 A | 3/1981 | MacChi | |
| 4,343,302 A | 8/1982 | Dillon | |
| 4,411,422 A | 10/1983 | Solloway | |
| 4,509,513 A | 4/1985 | Lasley | |
| 4,536,163 A | 8/1985 | Schnirch et al. | |
| 4,576,376 A | 3/1986 | Miller | |
| 4,621,621 A | 11/1986 | Marsalis | |
| 4,712,788 A | 12/1987 | Gaudreau, Jr. | |
| 4,731,882 A | 3/1988 | Ekman | |
| 4,776,581 A | 10/1988 | Shepherdson | |
| 4,805,601 A | 2/1989 | Eischen, Sr. | |
| 4,887,317 A | 12/1989 | Phillips et al. | |
| 4,934,694 A | 6/1990 | McIntosh | |
| 4,959,047 A | 9/1990 | Tripp, Jr. | |
| 4,974,829 A | 12/1990 | Gamow et al. | |
| 5,029,579 A | 7/1991 | Trammel | |
| 5,075,902 A | 12/1991 | McReynolds et al. | |
| 5,133,339 A * | 7/1992 | Whalen .............. | A61H 9/005 128/202.12 |
| 5,221,241 A | 6/1993 | Bare | |
| 5,242,339 A | 9/1993 | Thornton | |
| 5,295,929 A * | 3/1994 | Weisz .............. | A63B 22/02 4/495 |
| 5,356,361 A | 10/1994 | Watenpaugh | |
| 5,368,532 A | 11/1994 | Farnet | |
| 5,398,678 A | 3/1995 | Gamow | |
| 5,527,242 A | 6/1996 | Gangloff | |
| 5,571,062 A | 11/1996 | Saganovsky | |
| 5,623,944 A | 4/1997 | Nashner | |
| 5,662,311 A | 9/1997 | Waedekin et al. | |
| 5,702,323 A | 12/1997 | Poulton | |
| 5,704,881 A | 1/1998 | Dudley | |
| 5,706,822 A | 1/1998 | Khavari | |
| 5,738,612 A | 4/1998 | Tsuda | |
| 5,799,652 A | 9/1998 | Kotliar | |
| 5,830,162 A | 11/1998 | Giovannetti | |
| 5,860,857 A | 1/1999 | Wasastjerna et al. | |
| 5,919,419 A | 7/1999 | Majuri | |
| 5,921,892 A | 7/1999 | Easton | |
| 5,960,480 A | 10/1999 | Neustater et al. | |
| 6,027,464 A | 2/2000 | Dahlquist | |
| 6,033,344 A | 3/2000 | Trulaske et al. | |
| 6,042,537 A | 3/2000 | Kaiser | |
| 6,273,844 B1 | 8/2001 | Kelsey et al. | |
| 6,332,290 B1 | 12/2001 | DeLamare | |
| 6,332,354 B1 | 12/2001 | Lalor et al. | |
| 6,405,685 B1 | 6/2002 | Cox | |
| 6,482,128 B1 | 11/2002 | Michalow | |
| 6,527,678 B1 | 3/2003 | Wang et al. | |
| 6,539,946 B2 | 4/2003 | Weyergans | |
| 6,554,747 B1 | 4/2003 | Rempe | |
| 6,565,624 B2 | 5/2003 | Kutt et al. | |
| 6,609,054 B2 | 8/2003 | Wallace | |
| 6,645,126 B1 | 11/2003 | Martin et al. | |
| 6,656,091 B1 | 12/2003 | Abelbeck et al. | |
| 6,666,831 B1 | 12/2003 | Edgerton et al. | |
| D495,384 S | 8/2004 | Rolfes | |
| 6,783,482 B2 | 8/2004 | Oglesby et al. | |
| 6,821,233 B1 | 11/2004 | Colombo et al. | |
| 6,905,459 B2 | 6/2005 | Humphries, Jr. | |
| 6,918,858 B2 | 7/2005 | Watterson et al. | |
| 7,141,007 B2 | 11/2006 | Egger | |
| 7,166,064 B2 | 1/2007 | Watterson et al. | |
| 7,556,040 B2 | 7/2009 | Meyer et al. | |
| 7,591,795 B2 * | 9/2009 | Whalen .............. | A61G 10/023 128/202.12 |
| 7,594,281 B1 | 9/2009 | Stinson et al. | |
| 7,780,587 B2 | 8/2010 | Thornton et al. | |
| 7,785,242 B2 | 8/2010 | Solomon | |
| 7,837,597 B2 | 11/2010 | Reyes et al. | |
| 7,850,629 B2 | 12/2010 | Ravikumar | |
| 7,857,731 B2 | 12/2010 | Hickman et al. | |
| 7,862,478 B2 | 1/2011 | Watterson et al. | |
| 7,914,420 B2 | 3/2011 | Daly et al. | |
| 8,235,724 B2 | 8/2012 | Gilley et al. | |
| 8,447,401 B2 | 5/2013 | Miesel et al. | |
| 8,464,716 B2 * | 6/2013 | Kuehne ............ | A63B 21/00181 128/202.12 |
| 8,840,572 B2 * | 9/2014 | Whalen .............. | A61G 10/023 601/11 |
| 2001/0018564 A1 | 8/2001 | Manor et al. | |
| 2002/0010056 A1 | 1/2002 | Borsheim | |
| 2002/0032103 A1 | 3/2002 | Cook | |
| 2003/0032904 A1 | 2/2003 | Egger | |
| 2003/0204148 A1 | 10/2003 | Lange et al. | |
| 2004/0019304 A1 | 1/2004 | West | |
| 2004/0171465 A1 | 9/2004 | Hald et al. | |

(56) References Cited

U.S. PATENT DOCUMENTS

| | | |
|---|---|---|
| 2004/0238285 A1 | 12/2004 | Stokes |
| 2005/0075680 A1 | 4/2005 | Lowry et al. |
| 2006/0009333 A1 | 1/2006 | Wang |
| 2006/0185065 A1 | 8/2006 | Allen |
| 2006/0190051 A1 | 8/2006 | Gerber et al. |
| 2006/0199712 A1 | 9/2006 | Barnard et al. |
| 2007/0016116 A1 | 1/2007 | Reinkensmeyer et al. |
| 2007/0054783 A1 | 3/2007 | Egger |
| 2007/0219059 A1 | 9/2007 | Schwartz et al. |
| 2007/0272484 A1 | 11/2007 | Helms |
| 2008/0246581 A1 | 10/2008 | Irie et al. |
| 2008/0281633 A1 | 11/2008 | Burdea et al. |
| 2008/0306412 A1 | 12/2008 | Nieminen et al. |
| 2009/0014004 A1 | 1/2009 | Whalen et al. |
| 2009/0036272 A1 | 2/2009 | Yoo |
| 2009/0047644 A1 | 2/2009 | Mensah et al. |
| 2009/0082700 A1 | 3/2009 | Whalen et al. |
| 2009/0221404 A1 | 9/2009 | Dorogusker et al. |
| 2009/0236176 A1 | 9/2009 | Sheu et al. |
| 2009/0255531 A1 | 10/2009 | Johnson et al. |
| 2009/0269728 A1 | 10/2009 | Verstegen et al. |
| 2010/0000547 A1 | 1/2010 | Johnson et al. |
| 2011/0098157 A1 | 4/2011 | Whalen et al. |
| 2011/0098615 A1 | 4/2011 | Whalen et al. |
| 2012/0238921 A1 | 9/2012 | Kuehne et al. |
| 2012/0277643 A1 | 11/2012 | Whalen et al. |
| 2013/0095459 A1 | 4/2013 | Tran |
| 2013/0324893 A1 | 12/2013 | Kuehne et al. |
| 2015/0011917 A1 | 1/2015 | Whalen et al. |
| 2015/0379239 A1 | 12/2015 | Basta et al. |
| 2016/0000155 A1 | 1/2016 | Marecek et al. |
| 2016/0001118 A1 | 1/2016 | Kuehne et al. |
| 2016/0001119 A1 | 1/2016 | Jue et al. |
| 2016/0007885 A1 | 1/2016 | Basta et al. |
| 2016/0008650 A1 | 1/2016 | Jue et al. |
| 2016/0073704 A1 | 3/2016 | Basta et al. |
| 2017/0128769 A1 | 5/2017 | Long et al. |

FOREIGN PATENT DOCUMENTS

| | | |
|---|---|---|
| DE | 20305670 U1 | 8/2003 |
| DE | 10362043 A1 | 5/2005 |
| DE | 102006010887 A1 | 9/2007 |
| JP | 59-002993 | 1/1984 |
| JP | 63109878 A | 5/1988 |
| JP | 05-500760 | 2/1993 |
| JP | 05-049596 A | 6/1993 |
| JP | 1022334 | 10/1998 |
| JP | 11-113988 A | 4/1999 |
| JP | 2000-342713 | 12/2000 |
| JP | 2001-112886 | 4/2001 |
| JP | 2001-517187 A | 10/2001 |
| JP | 2002-28202 A | 1/2002 |
| JP | 2002-360644 | 12/2002 |
| JP | 2004-073445 A | 3/2004 |
| JP | 2005-102798 A | 4/2005 |
| JP | 2007-151676 A | 6/2007 |
| JP | 2008-538511 A | 10/2008 |
| WO | WO2004/103176 A1 | 12/2004 |
| WO | WO 2006/050787 A1 | 5/2006 |
| WO | WO 2006/061834 A2 | 6/2006 |
| WO | WO 2007/038888 A1 | 4/2007 |
| WO | WO2007/115565 A2 | 10/2007 |
| WO | WO2008/058567 A1 | 5/2008 |
| WO | WO2014/138228 A1 | 9/2014 |
| WO | WO2015/195983 A1 | 12/2015 |

OTHER PUBLICATIONS

Hamilton; Low-Tech Alternative to AlterG on Market; Runner's World; 2 pgs.; Aug. 16, 2012; (printed from internet: http://www.runnersworld.com/elite-runners/low-tech-alternative-alterg-market).

Hargens et al.; Lower body negative pressure to provide load bearing in space; Aviat Space Environ Med; 62(10); pp. 934-937; Oct. 1991.

Kawai et al.; Rehabilitation apparatus for treadmill walking using lower body positive pressue (Japanese & English abstracts); Aerospace and Environmental Medicine; vol. 44; No. 4; (year of pub, sufficiently earlier than effective US filing date and any foreign priority date) 2007.

Vacu Well Wellness & Beauty; Company History and Vacu Well Power Professional treadmill specifications; printed from website (http://www.vacuwell.com); 3 pgs.; printed Apr. 4, 2012.

Whalen et al.; Design U.S. Appl. No. 29/337,097 entitled "Adjustable Positive Pressure Support System," filed May 14, 2009.

Whalen et al.; U.S. Appl. No. 15/046,358 entitled "System, method and apparatus for applying air pressure on a portion of the body of an individual," filed Feb. 17, 2016.

\* cited by examiner

Relaxed unconstricted (contracted length)

↑ Extending locks (constricts)
↓ Chinese Finger Trap Concept

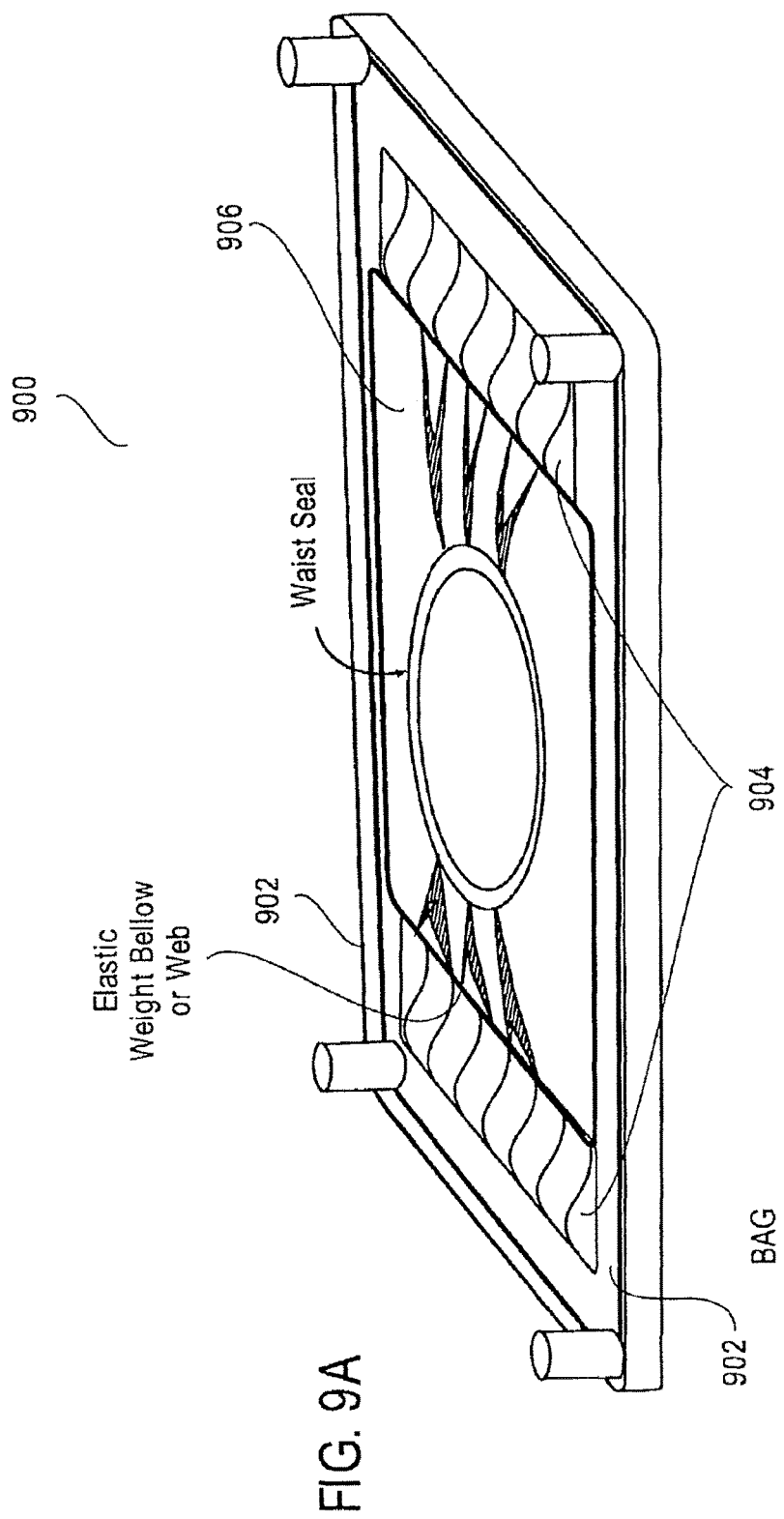

Plates form top of bag surface

Overlapping sealed plates $902_1...902_N$

Air flows to skeleton until Gate valve is opened to let air through second tube to main chamber

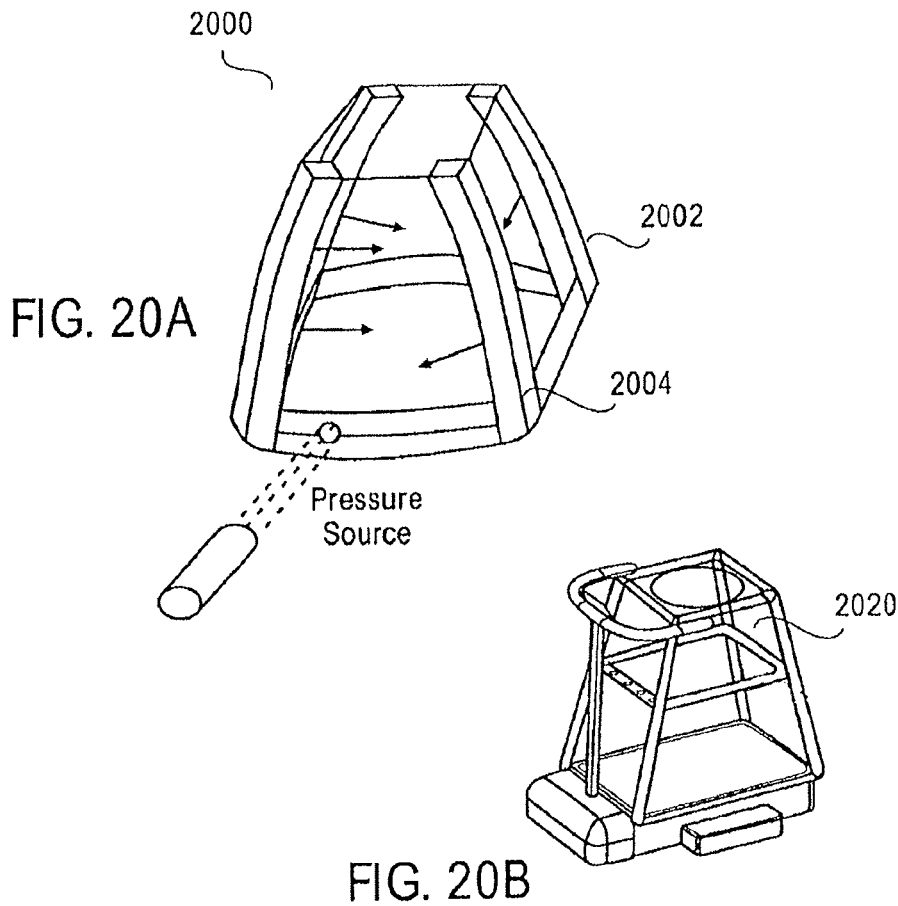
FIG. 20A
FIG. 20B
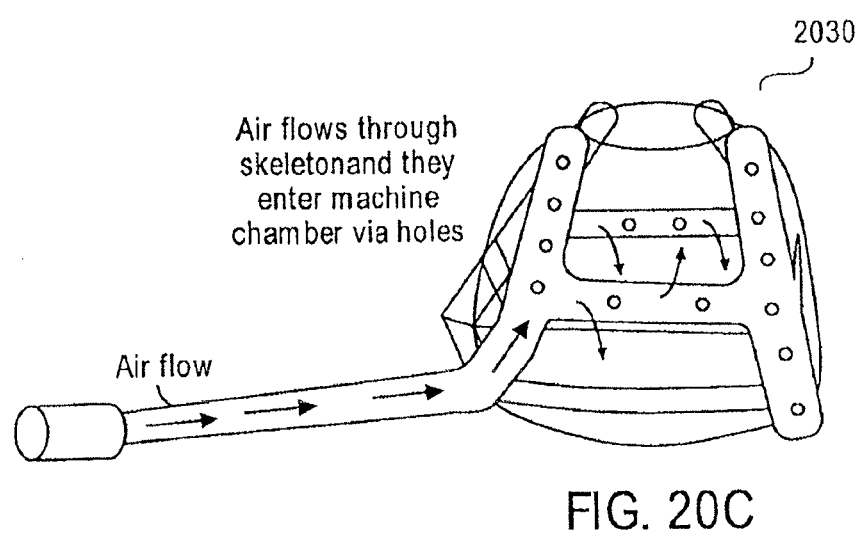
FIG. 20C inflate one ring at a time to vary the range of height adjustment Side View Top View

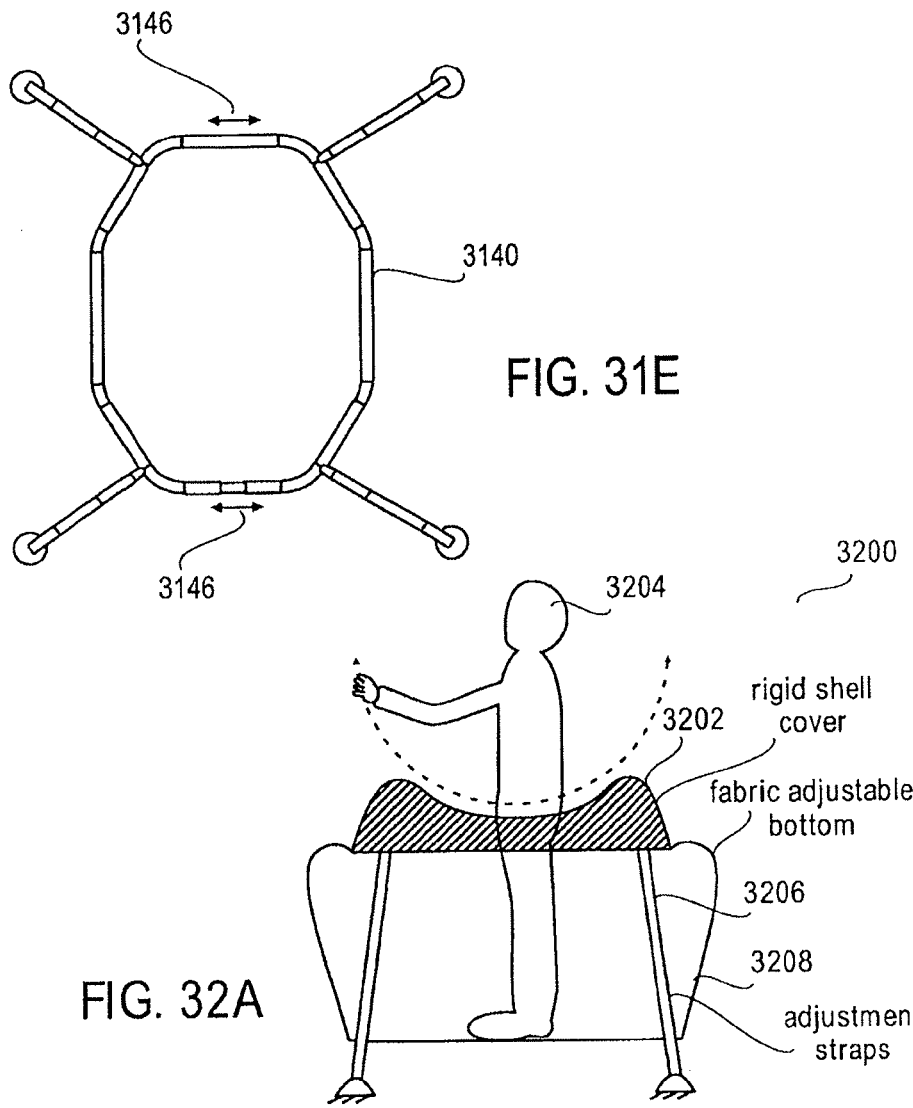
FIG. 31E
FIG. 32A
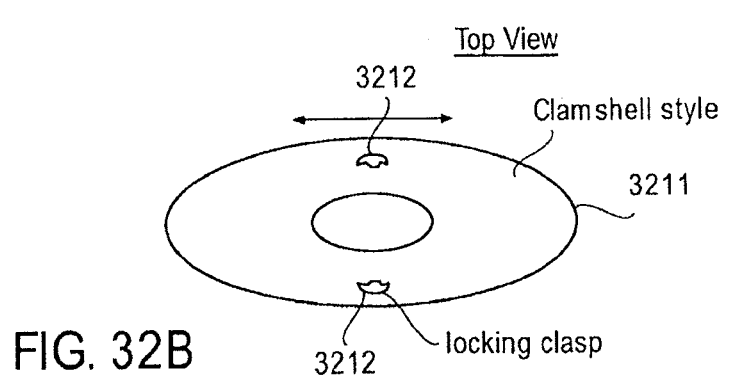
FIG. 32B

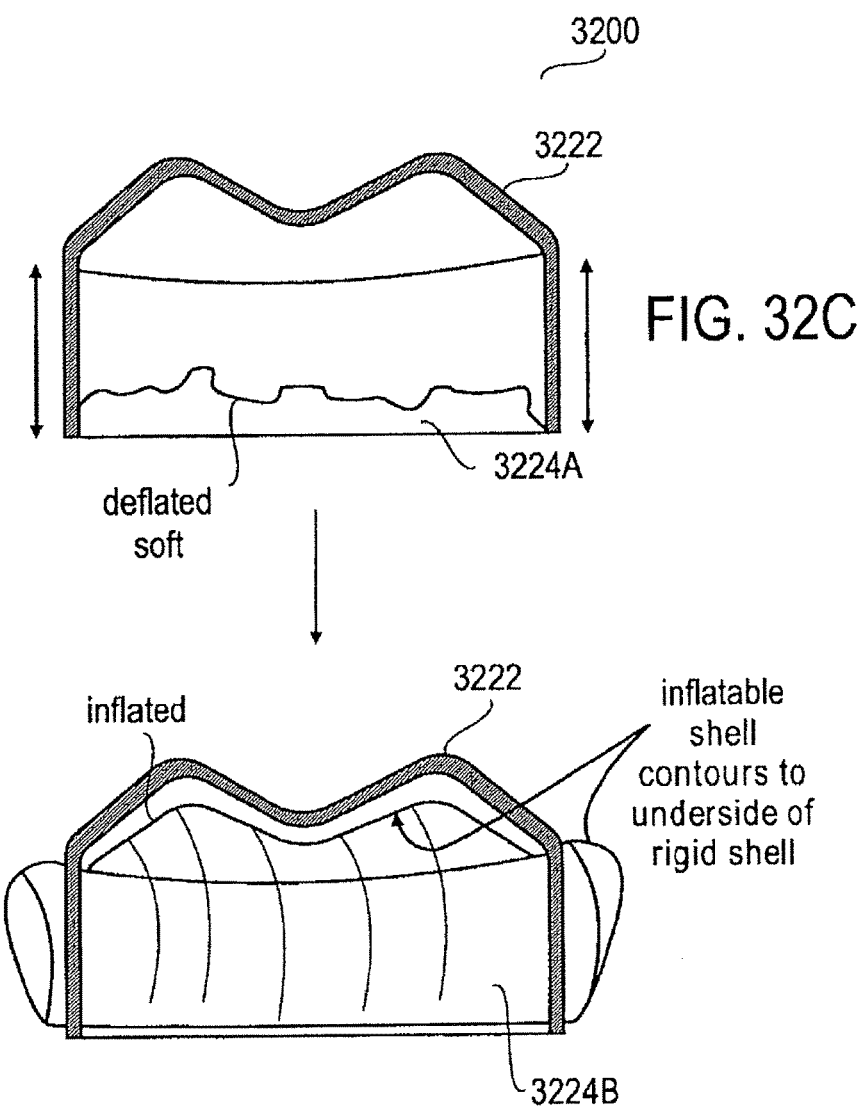

SYSTEMS, METHODS AND APPARATUS FOR DIFFERENTIAL AIR PRESSURE DEVICES

CROSS REFERENCE TO RELATED APPLICATIONS

This application is continuation of U.S. patent application Ser. No. 12/761,316, filed on Apr. 15, 2010, which is a continuation of International Patent Application No. PCT/US2008/011832, filed on Oct. 12, 2008; which claims priority benefit to Provisional Patent Application No. 60/999,102, filed on Oct. 15, 2007; Provisional Patent Application No. 60/999,101, filed on Oct. 15, 2007; Provisional Patent Application No. 60/999,061, filed on Oct. 15, 2007; and Provisional Patent Application No. 60/999,060, filed on Oct. 15, 2007, the contents of each of which are hereby incorporated by reference in their entirety.

The present application is also related to U.S. patent application Ser. No. 12/761,312, filed on Apr. 15, 2010, now abandoned, which is incorporated by referent herein in its entirety.

FIELD

The present invention relates to differential air pressure devices. More particularly, the present invention relates to systems, methods and apparatus for differential air pressure devices.

BACKGROUND

Gravity produces forces on the body. Methods of counteracting these forces have been devised for therapeutic as well as physical training uses. One way to counteract the effects of gravity on a body is to attach elastic cords at the waist and/or shoulder to produce either a positive or negative vertical force on the individual.

Other systems may use differential air pressure to simulate a low gravity effect, for example as described in U.S. Patent Publication No. 2007/0181121, which is incorporated herein by reference in its entirety.

A need exists for improved differential air pressure systems to be used for therapeutic and/or physical training uses.

SUMMARY OF THE DISCLOSURE

Described herein are various embodiments of differential air pressure systems. The air pressure systems comprise a chamber for receiving at least a portion of a user's body. Pressure in the chamber can be changed to adjust force on the user's body. Described herein are various methods and related structures for sealing a user into a pressurizable chamber. Also described herein are various methods and related structures for changing the shape and/or height of the chamber. Described herein are various types and configurations of chambers. Also described herein are various methods and related systems for treating various conditions using the differential air pressure systems, including but not limited to obesity, cardiac disease, multiple sclerosis, cerebral palsy, or Down Syndrome.

Structures for enclosing and sealing a portion of a body of a user into a differential air pressure system are described. In some variations, the structures comprise a chamber and a user seal coupled to the chamber. In these variations, the user seal comprises an adjustable opening that is capable of receiving and sealing around a user's body so that at least a portion of the user's body is sealed into the chamber. A sufficiently airtight junction is formed between the user's body and the chamber so that a nonzero differential pressure can be sustained in the chamber. The adjustable opening in the user seal may be capable of accommodating a range of user body sizes. In some variations, the user seal comprises a plurality of expansion slits distributed circumferentially around a perimeter of the user seal, and one or more of the expansion slits can be selectively closed or opened by the user to adjust a size of the opening in the user seal.

In some variations, a user seal configured for use in a differential air pressure system is configured to allow a user to rotate his body relative to a pressure chamber of the differential air pressure system. In these variations, the user seal is coupled to the chamber and comprises an opening that is capable of receiving and sealing around a user's body so that at least a portion of the user's body is sealed into the chamber, and a sufficiently airtight junction is formed between the user's body and the chamber so that a nonzero differential pressure can be sustained in the chamber. The user seal is configured to allow a user to rotate his body relative to the pressure chamber while maintaining the sufficiently airtight junction between the user's body and the chamber. In some variations, the user seals that allow user rotation comprise an outer structure coupled to the chamber, an inner structure comprising the opening that is capable of receiving and sealing around a user's body configured to seal around the user's body, wherein the inner structure is configured to mate with the outer structure and the inner structure is configured to rotate relative to the outer structure about a rotational axis of the outer structure.

Additional variations of user seals are described herein. Some user seals are configured to be anchored to a user's body so that the user seal maintains a relatively stable vertical position along the user's body as pressure in the chamber is varied. In these variations, the user seal is configured to be coupled to a chamber of a differential air pressure system. The user seal comprises an opening that is capable of receiving and sealing around a user's body so that at least a portion of the user's body is sealed into the chamber. A sufficiently airtight junction is formed between the user's body and the chamber so that a nonzero differential pressure can be sustained in the chamber. In some variations, the user seal comprises a body wrap that is anchored to a user's body. The body wrap may comprise a plurality of flaps. The flaps may be wrapped around one or more body parts of a user and secured to provide a grip between the body wrap and the user's body.

Still more variations of user seals are described herein. In some variations, a user seal may be configured to allow a user to translate along an axis of a chamber in a differential air pressure system. In these variations, the user seal is configured to be coupled to a chamber of a differential pressure system, and the user seal comprises an opening that is capable of receiving and sealing around a user's body so that at least a portion of the user's body is sealed into the chamber. A sufficiently airtight junction is formed between the user's body and the chamber so that a nonzero differential pressure can be sustained in the chamber. The user seal is configured to allow the user to translate his body along the axis of the chamber while maintaining the sufficiently airtight junction between the chamber and the user's body. For example, in some variations, the user seal may comprise a first section comprising an opening that is capable of receiving and sealing around a user's body and a second section that is coupled to the chamber. The first and second sections are slidably coupled to form a junction therebetween. A sufficiently airtight junction is formed between the user's body and the first section, between the first and section sections, and between the second section and the chamber so that at least a portion of the user's body is sealed into the chamber, a nonzero differential pressure can be sustained in the chamber, and the first section can translate relative to the second section to allow the user to translate along an axis of the chamber while substantially maintaining the nonzero differential pressure in the chamber.

Additional variations of user seals are provided herein. In some variations, a user seal comprises a lower section comprising an opening that is capable of receiving and sealing around a user's body and an upper section disposed on an upper surface of the lower section to form a junction between the upper and lower section. The upper section can be coupled to the chamber. A sufficiently airtight junction is formed between the user's body and the lower section, between the upper and lower sections, and between the upper section and the chamber so that at least a portion of the user's body is sealed into the chamber and a nonzero differential pressure can be sustained in the chamber.

Variations of pressurizable chambers for use in differential air pressure systems are described here. In some variations, a pressurizable chamber comprises an inflatable enclosure formed from a flexible material, and an adjustable frame that can be coupled to the inflatable enclosure. The adjustable frame controls at least one of a width and a height of the enclosure in its inflated state to reduce interference of the inflated enclosure with arm and/or leg motion of a user whose lower body is sealed into the pressurizable chamber and whose upper body is outside of the pressurizable chamber. In some variations, the adjustable frame comprises at least one contoured section to accommodate arm and/or leg motion of the user. In some variations, the adjustable frame comprises at least one telescoping member having a variable length, wherein the length of the at least one telescoping member is changed to adjust a dimension of the frame.

Additional variations of chambers for use in differential air pressure systems are described herein. In some variations, a pressurizable chamber comprises an inflatable enclosure and a height adjustable frame positioned around the enclosure, wherein the height adjustable frame capable of supporting a user's body weight in the event of a trip or a fall. The height adjustable frame can comprise a rear vertical support and a front vertical support. At least one of the rear and front vertical supports can comprise a height adjustment apparatus for engaging a lengthwise transverse member of the frame that extends between the rear vertical support and the front vertical support to adjust the height of the frame. In some variations, the height adjustment apparatus comprises a series of vertically arranged slots and the lengthwise tranverse member of the frame is engaged into one of the slots of the height adjustment apparatus to adjust a height of the frame.

Methods of treatment using a differential air pressure system are described herein. In some variations, the methods of treatment comprise creating a differential pressure in a chamber of a differential air pressure system, wherein the chamber is configured to receive at least a portion of a user's body and to adjust force on the user's body by adjusting pressure in the chamber, and adjusting pressure in the chamber in response to a condition-related metric determined for the user. The methods further comprise generating an initial setting of the differential air pressure system for the user based on a dependence of the condition-related metric on the adjustment of pressure. In some variations, the methods comprise generating an individualized treatment protocol for the condition based on the initial setting for the user. The methods may be used for treating a variety of health conditions, including but not limited to obesity, cardiac conditions, and musculoskeletal conditions.

Additional variations of methods of treatment are described herein. In some variations, the methods comprise creating a differential pressure in a chamber of a differential air pressure system, wherein the chamber is configured to receive at least a portion of a user's body and to adjust force on the user's body by adjusting pressure in the chamber. The methods comprise estimating an initial setting for the differential air pressure system based on a condition of the user. The methods further comprise receiving indication of pain experienced by the user as a function of pressure in the chamber and using the indication of pain at one or more pressure levels to set or modify a course of treatment for the condition. The methods may comprise receiving the indication of pain directly from a user in some variations, while in other variations the methods may comprise receiving the indication of pain from one or more sensors sensing a biological parameter of the user. The methods may for example be used for treating acute injuries or chronic injuries.

BRIEF DESCRIPTION OF THE DRAWINGS

The accompanying drawings, which are incorporated into and constitute a part of this specification, illustrate one or more embodiments of the present invention and, together with the detailed description, serve by way of illustration and not by illustration to explain the principles and implementations of the invention.

In the drawings:

FIGS. 9A-9G illustrate various embodiments of translational seals.

FIGS. 20A-20C illustrate other embodiments of skeleton enforced fabric shells for achieving height adjustment in a differential air pressure system.

FIGS. 31A-31E illustrate examples of structural bars that contour and constrain a flexible inflatable shell in a differential air pressure system.

FIGS. 32A-32D illustrate various embodiments of mechanisms for contouring an inflatable shell in a differential air pressure system.

DETAILED DESCRIPTION

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts. Unless clearly indicated otherwise explicitly or by context, the singular referents such "a," "an", and "the" are meant to encompass plural referents as well.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In accordance with one embodiment of the present invention, the components, process steps, and/or data structures may be implemented using various types of operating systems (OS), computing platforms, firmware, computer programs, computer languages, and/or general-purpose machines. The method can be run as a programmed process running on processing circuitry. The processing circuitry can take the form of numerous combinations of processors and operating systems, or a stand-alone device. The process can be implemented as instructions executed by such hardware, hardware alone, software, software alone, or any combination thereof. The software may be stored on a program storage device readable by a machine.

In addition, those of ordinary skill in the art will recognize that devices of a less general purpose nature, such as hardwired devices, field programmable logic devices (FPLDs), including field programmable gate arrays (FPGAs) and complex programmable logic devices (CPLDs), application specific integrated circuits (ASICs), or the like, may also be used without departing from the scope and spirit of the inventive concepts disclosed herein.

Differential Air Pressure Systems

Figure 1:
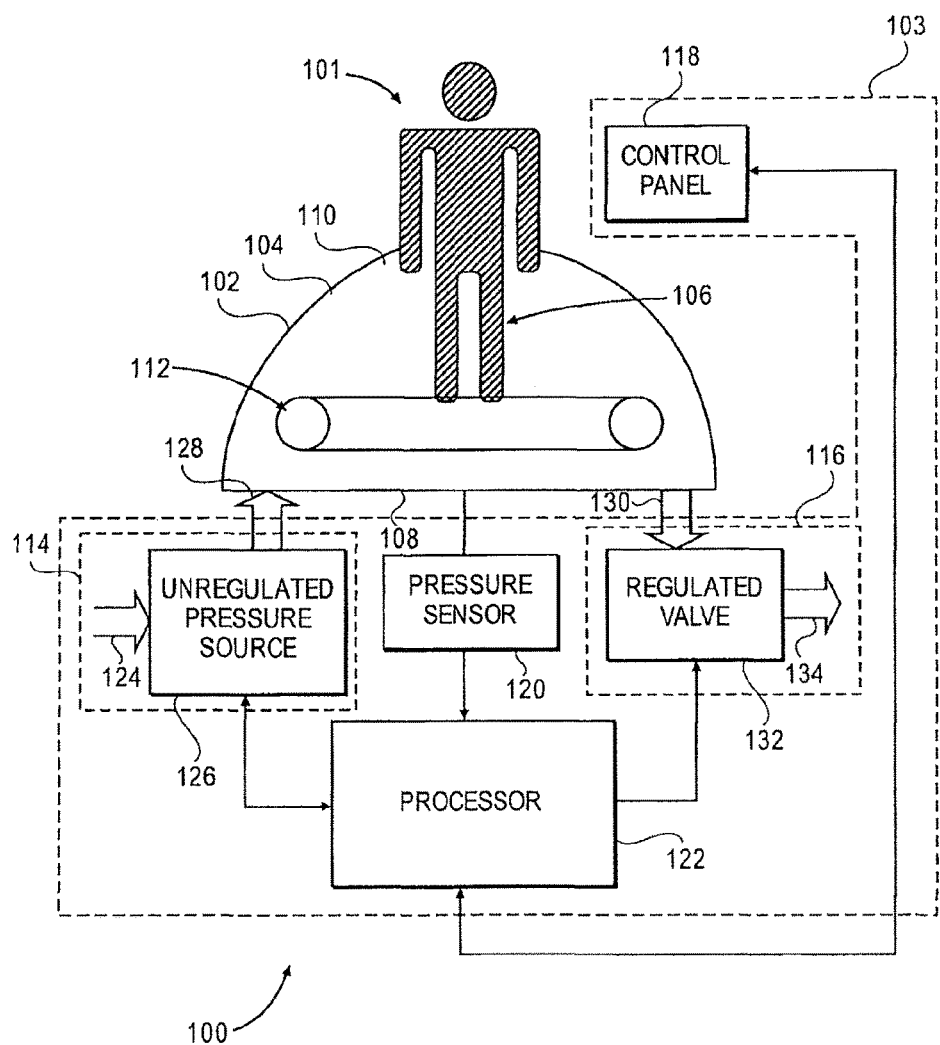
FIG. 1 is a block diagram schematically illustrating an example of a differential air pressure system that can be used for exercise in accordance with one embodiment.
Figure 2:
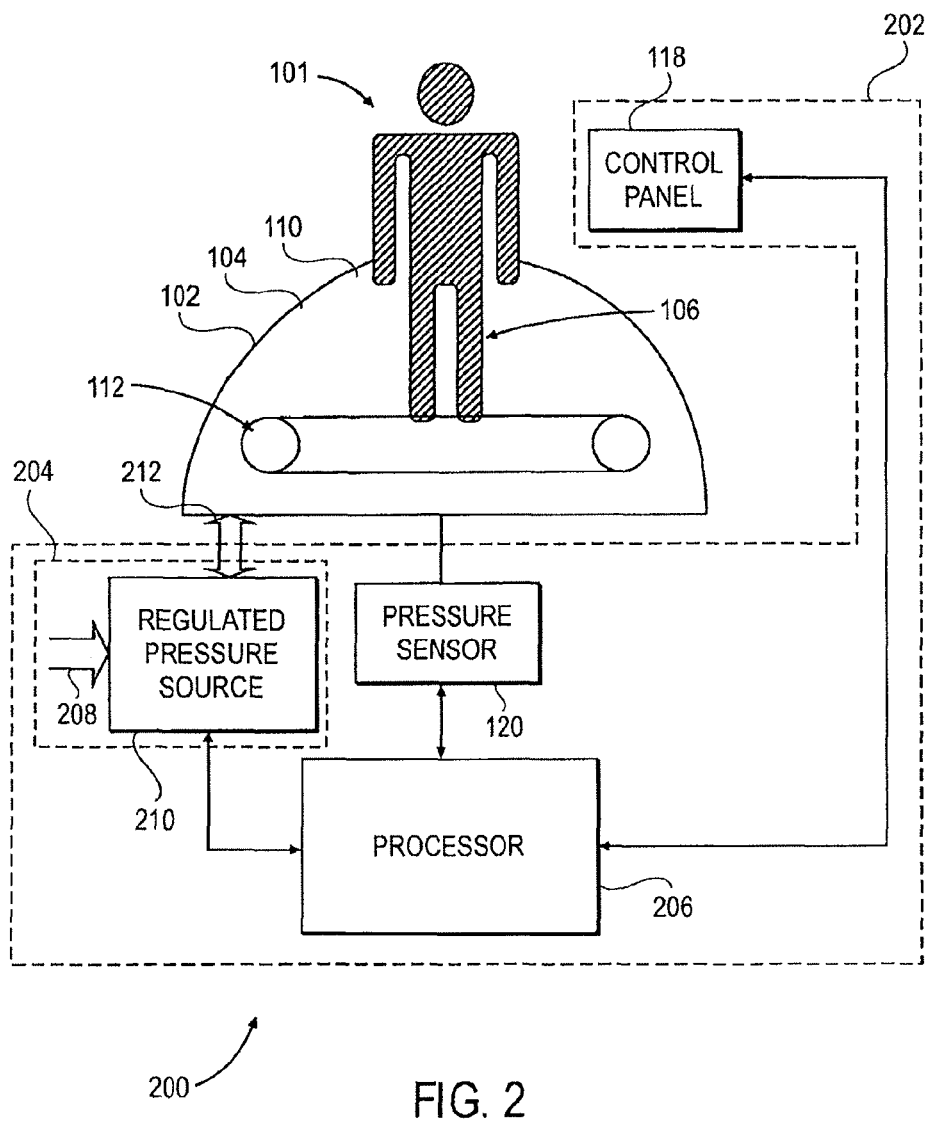
FIG. 2 is a block diagram schematically illustrating another example of a differential air pressure system that can be used for exercise in accordance with another embodiment.

Examples of differential air pressure systems are illustrated in FIGS. 1 and 2. In some variations, a differential air pressure system, such as the systems illustrated in FIGS. 1 and 2, operates by taking an individual, placing their lower body inside a sufficiently airtight chamber, and increasing the chamber pressure a desired amount above the room air pressure, ambient pressure. In certain embodiments, the pressure in the chamber can be controlled precisely. The effect is that the individual is modeled as a piston in a cylinder and the individual's normal weight due to gravitational force is unloaded a certain amount. By controlling the pressure with precision, the amount of offloading of the user's weight can also be controlled with precision. For example, for most individuals, the systems and methods described herein can incrementally change a user's effective body weight by as fine an adjustment as about 1% of the individual's body weight.

As described below, in some embodiments, a user seal describes a construction of a soft or flexible material, a stiff or rigid material, or a combination thereof, to span the gap between a user and a chamber in a sufficiently airtight manner. Various examples of constructions and methods of accomplishing a user seal are described below.

Furthermore, the differential air pressure systems and related methods described herein may be adapted for use used in a variety of different situations, such as, for example, dynamically (e.g., while a user is in motion and not simply standing still) or statically (e.g., while a user is stationary or relatively stationary). In some embodiments, the differential air pressure systems described herein may apply a positive pressure, where the pressure inside the chamber of a differential air pressure system is greater than the ambient pressure of the surroundings. In other embodiments, a negative pressure may be applied to the pressure chamber, the negative pressure being lower than that of the ambient pressure of the surrounding environment.

FIG. 1 is a block diagram schematically illustrating a system 100 for applying pressure to a lower body 106 of an individual 101 in accordance with one embodiment. The system includes a chamber 102 and controller 103 for adjusting or controlling (increasing or decreasing) and maintaining the pressure inside the chamber 102. An example of controller 103 is a negative feedback control system, e.g. as described in U.S. Patent Publication No. 2007/0181121, which is incorporated by reference herein in its entirety.

The chamber 102 includes an aperture 104 along an axis, such as a vertical axis, horizontal axis, etc., for receiving the lower body 106. In accordance with one embodiment, the chamber 102 may include a soft (flexible) or rigid (stiff) shell.

In variations in which the chamber 102 has a soft or flexible shell or a shell including a soft or flexible portion and a stiff or rigid portion, the soft shell or soft portion of the shell may be inflated or deflated accordingly. In certain variations, the chamber 102 may occupy an approximately hemi-spherical shape or half-ovoid shape when a soft shell or soft portion of a shell is inflated. FIG. 1 illustrates one embodiment where the chamber 102 includes a top portion of a sphere or ovoid-like shape with a planar cross-section as a base 108 of the chamber 102. The base 108 can support the individual user 101 in any position, e.g. standing or sitting, such as standing upright or sitting upright. It should be recognized a similar system may be constructed with the user in a horizontal position, e.g. by rotating the aperture 104 by about 90 degrees clockwise or counter-clockwise.

The soft shell or soft shell portion may be made of any suitable flexible material, e.g. a fabric (woven or nonwoven), a thin sheet of plastic, leather (natural or synthetic), and the like. In some variations, the soft shell or soft shell portion may be made from sufficiently airtight fabric that may be woven or non-woven. In some cases, a fabric used in a shell may be slightly permeable to air, but be sufficiently airtight so as to allow a desired degree of pressure to build up in the chamber. While the chamber is deflated, the soft shell or shell portion may allow for the lower body portion 106 to be positioned within the aperture 104. The aperture 104 may include for example an elliptical or circular shape and flexible fabric or other type of flexible material for accommodating various shapes of waistline of the individual lower body 106. The height of the flexible soft shell may be altered and the height restricted in a variety of embodiments, for example by using straps to pull down on the top surface. In some variations, the aperture 104 may include a rigid ring (not shown) that surrounds the waist or torso of the individual 101. The height of the chamber 102 can thus be adjusted by raising or lowering the rigid ring.

One or more bars (not shown) may be provided as part of the system 100 and may be configured to encompass at least a portion of the flexible shell below the waist of the individual 101. Such bar or bars may be configured to hold a flexible portion of shell in along the sides of the chamber to limit expansion, therefore keeping the shell close to the torso of the individual 101 allowing for comfortable arm swing. The bar or bars may limit the ability of a flexible shell from expanding into an undesired shape, e.g. a spherical shape. The bar or bars may have any suitable configuration. For example, in some variations, two parallel bars may be provided along sides. In other variations, one U-shaped bar may be used, where the base of the U-shaped bar may be positioned in front of the user. Similarly, a rigid shell or partially rigid shell may be configured to allow for keeping the arms of the individual 101 from touching or otherwise being interfered with by the rigid shell while the individual 101 is moving (walking or running) through a contoured shape, e.g. a saddle shape.

The system 100 may also include a rear entrance walkway (not shown) to facilitate entrance and exit to and from the chamber 102. A rear entrance walkway may in some variations include a step. In variations of the chamber 102 having a soft shell or soft shell portion, such a rear entrance walkway, if present, may be used a means for supporting the soft shell or soft shell portion in an deflated state, e.g. so that it is easier to attach a seal 110 to the individual 101. A walkway may also serve as a safety platform in case the shell of the chamber 102 rips (in the case of a flexible shell, e.g. a fabric shell) or breaks (in the case of hard shell). A walkway may also include one or more holding bars for the individual 101 to hold onto to support the individual or to prevent the individual from falling.

With respect to variations of the chamber 102 having a hard shell, the chamber 102 may include a door (not shown) or other type of opening that allows the individual 101 to enter and exit the chamber 102. For example, a door can be used, where the door can swing open, swing down, or slide open. A door can be comprised of fabric, plastic, leather or other type of flexible material that can be closed in a sufficiently airtight manner with a zipper, snaps, and/or other type of closure (e.g. Velcro™ type hook and loop closures). In some variations, aperture 104 may be created by moving two halves of chamber 102 apart and back together like a clam-shell or a cockpit. Additionally, the height of hard shell may be adjusted based on the height of individual 101.

A user seal 110 is provided between the lower body 106 and the aperture 104 at or near the torso or the waistline of the individual 101. In accordance with one embodiment, the seal 110 includes a plurality of openings/leaks around the torso of the individual 101 to cool the individual 101 and to better control distribution of pressure around the torso of the individual 101. For example, leaks positioned in front by the stomach of the individual 101 help with the bloating due to ballooning of the flexible waist seal under pressure. Such deliberate leaks may be implemented by sewing non-airtight fabrics, or by forming holes in the shell or fabric of the chamber 102. The seal 110 can be made of a substantially airtight material and/or non-airtight fabric. The seal 110 can be implemented using any suitable means for securing to the user's body, e.g. a skirt, pants, other means or technique as described herein in greater detail below, or any combination thereof.

In accordance with one embodiment, the seal 110 may include a separable seal closure. Non-limiting examples of separable seal closures include zippers, snaps, Velcro™ type hook and loop closures, kayak style attachment (e.g. using a zipper) over a rigid lip that is attached to the shell, clamps, and deformable loops. In some variations, the seal 110 may include means for anchoring to the individual lower body 106 and means for attaching to the aperture 104. Means for anchoring to the user's body may include, for example, Velcro™ type straps that extend around the circumference of a user's thighs for adjustment to accommodate different thigh sizes, and a belt that keeps the seal anchored at the hipbone. Other examples of means for anchoring to the user's body may include a high friction material that seals against the user's body and remains anchored because of a high friction coefficient. The seal 110 may be breathable and washable. In accordance with another embodiment, the seal 110 may seal up to the individual chest, and in some variations the seal may extend from the user's waist region up to the chest. In some variations, the seal 110 may include a skirt-type seal. Additional non-limiting examples of seals are described in detail herein.

An optional exercise machine 112 may be at least partially housed within the chamber 102. Any suitable exercise machine may be used, e.g. a treadmill, a stationary bicycle, a rowing machine, a stepper machine, an elliptical trainer, a balance board, and the like. The exercise machine 112 may be, for example, a treadmill having an adjustable height, inclination, and speed. Any parameter of the exercise machine can be adjusted based on a dimension of the individual user 101. For example, the height, position within the chamber, seat position, handgrip position, and the like, of the exercise machine 112 can be adjusted to accommodate a dimension of the individual 101. Those of ordinary skill in the art will appreciate that the treadmill shown is not intended to be limiting and that other exercise machines can be used without departing from the inventive concepts herein disclosed.

In some variations, a differential air pressure system includes a pressurizable chamber without an exercise machine 112. In these variations, the chamber 102 may be used without any exercise machines, e.g. as a means to improve jumping ability, balance, or general movement.

Any suitable type of controller 103 can be used for adjusting the pressure inside the chamber 102. As stated above, the controller 103 in some variations is configured to maintain the pressure in the chamber 102, e.g. if the controller 103 is configured as a negative feedback control system. In certain variations, the controller 103 includes an intake system 114 and an outtake system 116. In some cases, the controller 103 may include a pressure sensor 120, a processor 122, or a control panel 118, or any combination of two or more of the above.

In the variation illustrated in FIG. 1, intake system 114 includes an input port 124 for receiving a gas (for example, air), a pressure source 126 (pump or blower), and an output port 128. The gas flow from pressure source 126 may be unregulated. Pressure source 126 can be turned on or off. In accordance with another embodiment, the pressure source 126 may include a variable fan speed that can be adjusted for controlling the incoming airflow to the chamber 102. Pressure source 126 pumps gas from input port 124 to output port 128.

In the variation illustrated in FIG. 1, outtake system 116 includes an input port 130 for receiving gas from chamber 102, a pressure regulating valve 132, and an output port 134 to ambient pressure. The pressure regulating valve 132 controls the exhaust flow from the chamber 102. The input port 130 is an output port of the chamber 102. Gas leaves the chamber 102 via the output port 134. In accordance with another embodiment, a safety exhaust port (not shown) may be connected to the chamber 102 for allowing gas to exit the chamber 102 in case of pressure increasing beyond a limit such as a safety limit, e.g. in an emergency or a system failure.

In some variations, the differential air pressure system as illustrated in FIG. 1 includes a user interface system for allowing the individual 101 or an operator to interact with the system 100 via the processor 122. Any suitable user interface may be used, e.g. a touch sensor such as a touch screen, a handheld button, a handheld control box, or a voice-activated user interface. In certain variations, a control panel 118 includes a user interface system. The user interface and/or the control panel may be interfaced with the processor 122 in a wireless configuration or hardwired. In some variations, the individual 101 may use a touch-screen interface (not shown) on the control panel 118, e.g. to program the pressure within the chamber 102, and/or to control one or parameters of the exercise machine, e.g. the speed, the inclination, the resistance and/or the height of the exercise machine 112. The control panel 118 may also be used by the individual 101 to calibrate the system for correct body weight and/or to input a desired factor or parameter to determine an intensity of exercise. For example, the user may specify that he wants to exercise at a certain fraction of his body weight, or offset his body weight by a certain number of pounds, or exercise at a certain heart rate or blood pressure, or exercise at a certain pain level. Non-limiting examples of calibration processes are described in U.S. patent application Ser. No. 12/761,312, entitled "SYSTEMS, METHODS AND APPARATUS FOR CALIBRATING DIFFERENTIAL AIR PRESSURE DEVICES," which is incorporated by reference herein in its entirety.

In one embodiment, an optional pressure sensor 120 is connected to the chamber 102 for measuring a differential pressure between the pressure inside the chamber 102 and the ambient pressure. Those of ordinary skill in the art will appreciate that the pressure sensor 120 shown is not intended to be limiting and that other types of pressure transducer or pressure measuring sensors can be used without departing from the inventive concepts herein disclosed. The pressure sensor 120 communicates its measurements to the processor 122. System 100 does not need to include pressure sensor to accomplish the calibration, e.g. as described in U.S. patent application Ser. No. 12/761,312, entitled "SYSTEMS, METHODS AND APPARATUS FOR CALIBRATING DIFFERENTIAL AIR PRESSURE DEVICES," which is incorporated by reference herein in its entirety.

In some variations, the controller 103 can be configured to use input from the pressure sensor 120 to control the pressure source 126 and/or the pressure regulating valve 132. The processor 122 can communicate with the user interface or control panel 118, if present. An example of the algorithm of the processor 122 is the processor 122 receives an input from the control panel 118. For example, the input may include a desired pressure within the chamber 102, a desired percentage of body weight of the individual, an amount of weight to offset the user's body weight, and/or a pain level. The processor 122 can be configured to operate the pressure source 126 and/or the regulated valve 132 using a negative feedback loop, circuit, or system. The processor 122 can in certain variations monitor the pressure inside the chamber 102 with input from the pressure sensor 120. Based on the measurements from the pressure sensor 120 and the input from user, e.g. via the control panel 118, the processor 122 sends a drive signal to the regulated valve 132 and/or the pressure source 126 to increase or decrease the exhaust flow through the chamber 102 so as to maintain the pressure within chamber 102 as close as possible to the desired pressure. The desired pressure may be pre-set in some variations, and in some variations may be received from the control panel 118 or derived from information received from user, e.g. via the control panel. The pressure (positive or negative) inside the chamber 102 produces an upward or downward force on the individual 101 resulting in a lighter or heavier sensation.

The processor 122 may in some variations communicate with the exercise machine 112. The processor 122 may receive one or more input parameters via the control panel 118 for the exercise machine 112. For example, the exercise machine 112 may include a treadmill with speed or inclination adjusted by the processor 122 based on the pressure sensed inside the chamber 102.

In accordance with some embodiments, the system 100 may be controlled to monitor and/or maintain various performance parameters, such as to achieve a constant stride frequency. In some variations, the processor 122 may be configured to receive input from one or more user performance parameter sensors, e.g. heart rate, blood pressure, pain level, stride length, cadence or stride frequency, foot strike pressure, and the like. One or more parameters of the exercise machine such as speed, resistance and/or pressure inside the chamber may be adjusted in response to the one or more user parameters. For example, a sensor may be placed on a treadmill to detect the impact from the user's feet on the treadmill and compare with subsequent values to measure the time duration between strides. The machine can then adjust pressure, tilt, speed, etc. to maintain a specific stride rate.

In accordance with yet another embodiment, the system 100 may include an acceleration/deceleration sensor coupled to the individual 101 sensing whether the user is speeding up or slowing down. Those of ordinary skill in the art will recognize that there are many ways of implementing such a sensor. The processor 122 receives the measurement from the acceleration/deceleration sensor and may send a signal to increase or decrease the speed of the treadmill in response to the measurement in combination with increasing or decreasing the pressure inside the chamber 102.

The processor 122 may also include a data storage (not shown) such as a database storing various data and/or executable programs that may be selected or programmed in by the individual 101 or by an operator via the control panel 118. The data storage may include a repository of data that may be used to control the system 100. For example, while receiving data from one or more sensors (including the pressure sensor, performance sensors of the individual, a safety sensor, etc. . . . ) the processor 122 may determine that one or more parameters has reached a pre-set limit or a dangerous level. The processor 122 then alters the pressure and/or a parameter of the exercise machine 112, e.g. a resistance or speed, e.g. the speed of the treadmill. For example, a trainer could set a maximum speed, heart rate, resistance, cadence, blood pressure, or pain parameter for the individual 101. The processor 122 would ensure that that parameter is not to be exceeded. The data storage may also be used to store past performance data and personal records for different protocols and the system 100 could allow the individual 101 to run against previous performance data or personal records.

The data storage may also include various training programs based on the selection from the control panel 118. The processor 122 could then limit activity levels to non-harmful ranges for the individual 101 based on one variable, a combination of variables, e.g. a maximal allowed user heart rate. The data storage may also be able to log and record the performance and activities of the individual 101 as well as store any calibration data so that the individual 101, trainer, therapist or the like need not perform that the calibration process for every use of the differential air pressure system.

FIG. 2 is a block diagram schematically illustrating a system 200 for applying pressure to a lower body portion 106 the individual 101 in accordance with another embodiment. The system 200 includes the chamber 102 and controller 202 for adjusting (increasing or decreasing) the pressure inside the chamber 102. In some variations controller 202 can be configured to maintain pressure inside the chamber 102. An example of controller 202 is a negative feedback control system.

Controller 202 for adjusting (and in some variations maintaining) the pressure inside the chamber 102 includes an intake system 204. In some variations, the controller includes a user interface such as described in connection with FIG. 1. In certain variations, a user interface may be included as part of a control panel 118. In some variations, controller 202 includes a pressure sensor 120, and a processor 206.

In the variation illustrated in FIG. 2, the intake system 204 includes an input port 208 for receiving a gas (for example, air), a regulated pressure source 210, and an output port 212. The regulated pressure source 210 pumps gas from the input port 208 to the output port 212. The flow of air is regulated via the regulated pressure source 210. The regulated pressure source 210 may include an adjustable exhaust valve for controlling the gas flow rate through output port 212. In accordance with some variations, the regulated pressure source may include a pump having an adjustable fan blade size or fan speed. The gas flow rate can be adjusted by varying the fan speed or fan blade size. A safety exhaust port (not shown) may be connected to the chamber 102 for allowing gas to exit the chamber 102 in case of a pre-set limit is reached, e.g. in an emergency or a system failure.

The processor 206 communicates with the control panel 118, if present, and the pressure sensor 120 to control the regulated pressure source 210. An example of the algorithm of processor 122 is the processor 206 receives an input from the user, e.g. via control panel 118. For example, the input may include a desired pressure inside the chamber 102, a body weight of the individual, a factor to determine a percentage of body weight that the individual would like to experience during exercise, a weight offset the user would like use to offset his weight at relative to weight at ambient pressure, a pain limit, a heart rate, and/or a blood pressure, and the like. In the variation illustrated in FIG. 2, the processor 206 can operate the regulated pressure source 210 using a negative feedback loop, circuit, or system. The processor 206 monitors the pressure inside the chamber 102 with the pressure sensor 120. Based on the measurements from the pressure sensor 120 and the input from the user (e.g. via control panel 118), the processor 122 sends a drive signal to the regulated pressure source 210 to increase or decrease the gas flow through the chamber 102 so as to maintain the pressure within chamber 102 as close as possible to the desired pressure received from the user, e.g. via control panel 118. The pressure (positive or negative) inside the chamber 102 produces an upward or downward force on the individual 101 resulting in a lighter or heavier sensation.

In some variations, the processor 206 may communicate with an exercise machine 112 at least partially housed inside the chamber 102. Any suitable exercise machine 112 may be used, e.g. as described above in connection with FIG. 1. In some variations, no exercise machine is used. The processor 206 may receive one or more input parameters (e.g. speed, resistance, cadence, incline, workout algorithm, or the like) from the user, e.g. via control panel 118, for the exercise machine 112. For example, the exercise machine 112 may include a treadmill with speed or incline adjusted by the processor 206 based on the pressure sensed inside the chamber 102.

The processor 206 may also include a data storage (not shown) such as a database storing various data and/or executable programs that may be selected or programmed in by the individual 101 or an operator via the control panel 118. The data storage may include a repository of data that may be used to control the system 200. For example, while receiving data from all sensors, the processor 206 may determine that one or more parameters have reached a pre-set limit or a dangerous level. The processor 206 then alters the pressure and/or one or more parameters of the exercise machine 112, e.g. the speed of a treadmill. For example, a trainer or physical therapist could set a maximum speed parameter for the individual 101. The processor 206 could limit that speed so that it is not exceeded. The data storage may be used to store past performance data and/or personal records for different protocols and the system 200 could allow the individual 101 to train against previous performance data or personal records.

The data storage may also include various training programs based on a selection from the control panel 118. The processor 206 can in some variations limit one or more activity levels of the individual to non-harmful levels based on one or more variables, e.g. a maximal heart rate for the user. The data storage may also be able to log and record the performance and activities of individual 101.

User Seal for a Differential Air Pressure System

As described above, a user seal is provided between the user and the chamber of a differential air pressure system to allow the chamber to sustain a nonzero differential air pressure (i.e. sustain a pressure in the chamber that is different than ambient pressure). A functional user seal forms a sufficiently airtight junction to the user's body and a sufficiently airtight junction to the pressure chamber to sustain the desired nonzero differential air pressure. Further, any intermediate junction within the user seal must also be sufficiently airtight so as to sustain the desired nonzero differential pressure. In various embodiments, user seals can employ any suitable technique or attachment scheme to form the sufficiently airtight junction between the user's body and the seal itself, e.g. by using a sufficiently airtight elastic material, an elastic band, a cinch, an adhesive, friction, and/or close physical contact (e.g. a seal that is moldable or contoured to follow the shape of a user's body). As described herein, a user seal can be anchored to the user to form and maintain a sufficiently airtight junction even when the user is moving (i.e., up and down, rotationally, or forward or backward), for a wide range of clothing types that may be worn by users, and even when the user is sweating, etc.

If an adhesive is used to anchor a user seal to a user (alone or in combination with another anchoring mechanism), any suitable adhesive type may be used, and any suitable adhesive delivery may be used. For example, adhesive tape, a spray-on adhesive, solvent based glue, and/or a curing epoxy may be used.

To accommodate as many users as possible, it is desired for differential air pressure systems to include a user seal that can accommodate a range of different body sizes and body shapes. As discussed below, a system with a user seal that includes an adjustable orifice in the chamber for accepting the body of a user that does not require multiple discrete orifice sizes, shapes, etc may be a beneficial improvement on a differential air pressure system. Furthermore, a single adjustable orifice seal in a chamber that is adaptable to many users may speed up user entrance and exit from the system and/or may reduce the number of steps and/or specialized accessories needed to use the differential air pressure system. Additionally, variations of user seals are provided below that include an effective means of anchoring the user seal to the body of the user to create the seal between the user and the chamber.

In some embodiments, a separate insert may be added between the user's body and a deformable material of a user seal to collect sweat or other bodily substances, so that subsequent users can exercise in a clean sanitary environment. Such an insert may be applied to any of the adjustable orifice user seals described herein.

Seal Orifice Sizing

Various techniques and structures may be employed to form a user seal having an adjustable orifice that can accommodate a range of users. Non-limiting examples of user seals having an adjustable orifice are described herein. Further, various techniques and structures may be employed to anchor the seal to the user, e.g. an elastic material, an elastic band, a cinch, an adhesive, friction, and/or close physical contact such as when the seal is molded or contoured to the user's body.

Figure 3:
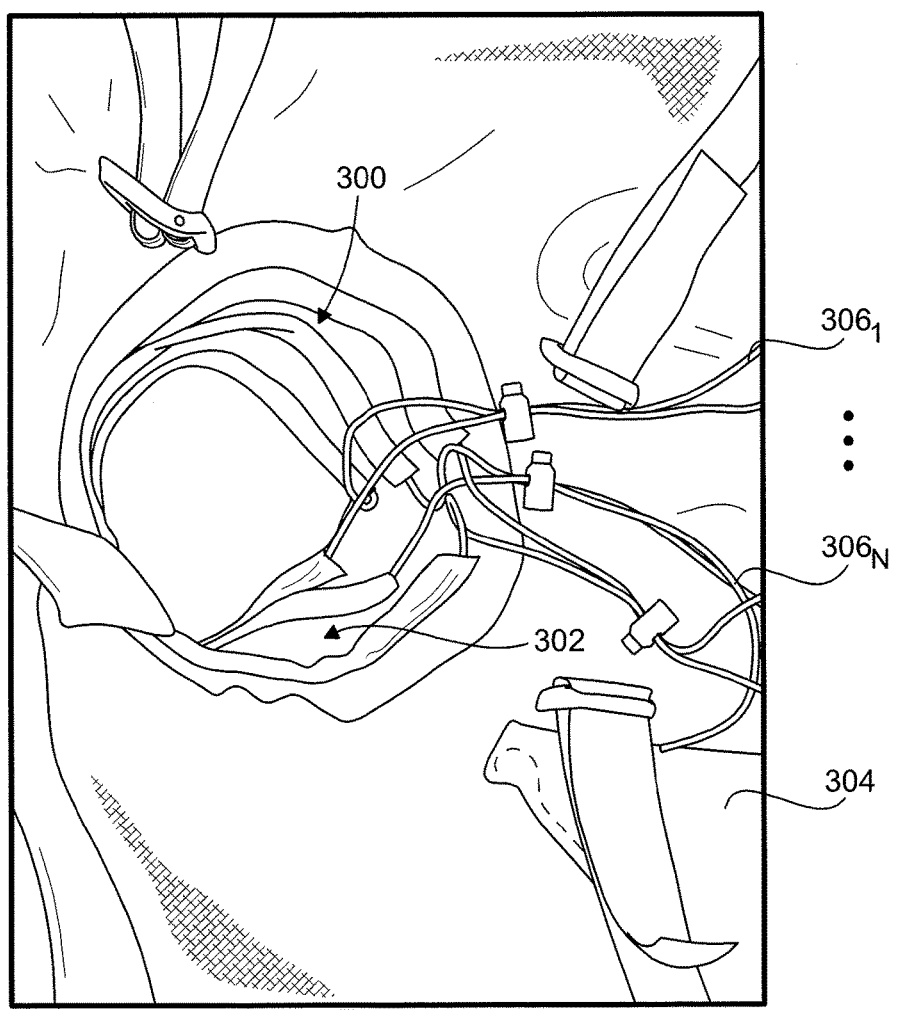
FIG. 3 illustrates one embodiment of an adjustable orifice.

FIG. 3 depicts one embodiment of a seal 300 including an adjustable orifice for use with a differential air pressure system, such as those illustrated in FIG. 1 and FIG. 2. As illustrated in FIG. 3, in some variations, the adjustable orifice seal 300 includes a circumferential skirt 302 that allows for vertical movement of the user and is in the shape of an upside-down skirt (e.g., an inverted volcano). The adjustable orifice seal 300 (including skirt 302) can be attached to a shell 304 of the differential air pressure system, for example using a sewing stitch, adhesive, magnets, zipper, snaps, buttons, Velcro™ type closures, or any other means described herein or otherwise known. Thus, a user of the differential air pressure system that includes seal 300 steps inside the central opening, and pull ups the skirt 302 around his or her torso. In one embodiment, a liner insert (not shown), or other easily interchangeable inner material, is included in the adjustable orifice seal 300, e.g. to avoid accumulation of bacteria from one user to the next.

In some variations, one or more drawstrings (laces) or other cinching mechanism (e.g. a ratchet) may be positioned circumferentially around the opening for the user in a user seal. Drawstrings or laces, if used, may be elastic or non-elastic. The cinching mechanism allows the size of the opening to be varied to accommodate a range of user sizes. Further, the one or more drawstrings or other cinching mechanism function to press a user seal against a user's body when cinched, thus anchoring the seal to the body to form a sufficiently airtight junction to sustain a desired differential pressure in the chamber. The one or more drawstrings or other cinching mechanism can be arranged in any suitable manner to cinch the user seal so as to urge the seal against the user's body. For example, one or more drawstrings may be circumferentially threaded around at least a portion of a circular or elliptical user seal to enable cinching. In certain variations, two or more drawstrings may be circumferentially threaded around at least a portion of a circular or elliptical user seal, e.g. so that the two or more drawstrings are arranged in a generally concentric fashion. In certain cases, multiple drawstrings may be arranged vertically relative to each other and circumferentially threaded around at least a portion of a seal so that the multiple drawstrings provide anchoring of the seal to the user vertically along a user's torso. Alternatively or in addition, one or more drawstrings may be threaded through a gap in the user seal, where the gap allows the user seal to open to accommodate entry or exit of the user. The one or more drawstrings may be cinched to close the gap to seal the user into the chamber before operation of the differential air pressure system.

For example, as illustrated in FIG. 3, the skirt 302 includes one or more drawstrings, such as drawstring $306_1$ to drawstring $306_N$. The one or more drawstrings can enable smaller users to tighten the skirt 302 as needed. The draw strings $306_{1\ldots N}$ further anchor the adjustable orifice skirt 302 to the body to prevent the skirt from inverting when the differential air pressure systems of FIG. 1 and FIG. 2 are pressurized.

Figure 4A:
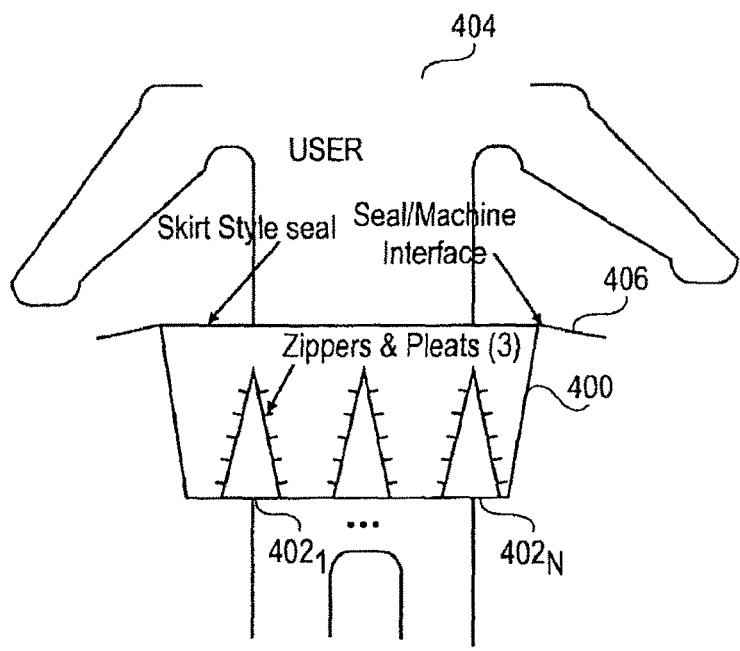
FIGS. 4A-4B illustrate another embodiment of an adjustable orifice.
Figure 4B:
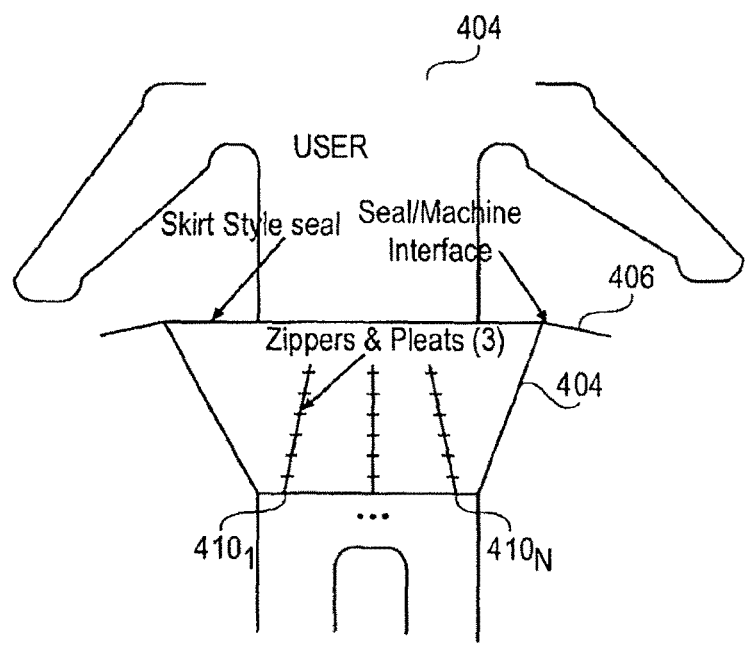

FIGS. 4A and 4B illustrate additional embodiments of an adjustable orifice seal that include an adjustable skirt 400, wherein the skirt is made of flexible material such as neoprene, rubber, etc. and is attached to a shell 406 of a differential air pressure system. In one embodiment, to make the circumference of the skirt 400 smaller (e.g., to transition the orifice skirt 400 from the configuration illustrated in FIG. 4A to that illustrated in FIG. 4B), a series of pleats, such as pleats $402_1$ to $402_N$, are included in the adjustable orifice. In one embodiment, the pleats $401_{1\ldots N}$ may be sections of fabric or other flexible material that can be tightened with a zipper, snap, button, or Velcro™ type closure, made of an elastic material, include fastening buckles, drawstrings, or other suitable closure. There may be additional flexible material (e.g. a fabric layer) disposed between the pleats for maintaining continuity of the skirt fabric layer and air seal if the pleat is not used.

By closing one or more of pleats $402_{1\ldots N}$ to form closed pleats $410_{1\ldots N}$ as shown in FIGS. 4A and 4B, the circumference of the skirt 400 is reduced about user's 404 waist. Conversely, to open up the circumference of the orifice skirt 400, one or more closed pleats $410_{1\ldots N}$, may be opened. Furthermore, because any distribution of closed and open pleats may be achieved with the adjustable orifice variation illustrated in FIGS. 4A-4B, the orifice is adjustable to fit a wide range of body sizes and shapes in a differential air pressure system.

Figure 5A:
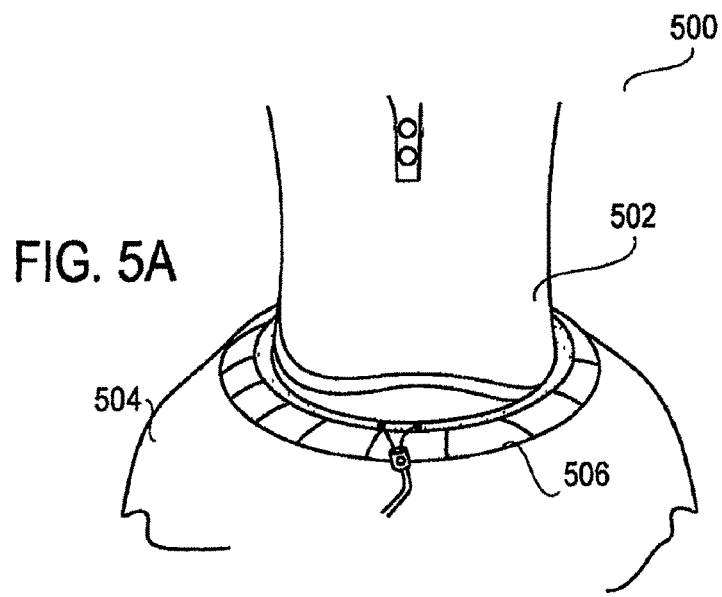
FIGS. 5A-5L illustrate additional embodiments of adjustable orifices, which in some variations may provide an anchor to the user's body.

FIG. 5A illustrates another embodiment of an adjustable orifice seal 500 utilizing drawstrings or belts. In the particular embodiment illustrated in FIG. 5A, a single drawstring 502 is threaded circumferentially around at least a portion of the adjustable seal orifice 500. The seal 500 may comprise a strip of elastic material 506 that is, in turn, connected to a flexible shell 504 of a differential air pressure machine. The drawstring, when cinched, gathers the elastic material 506 to form a sufficiently airtight seal around the torso of the user. In another embodiment, multiple drawstrings are utilized, e.g. as illustrated in FIG. 3. In some variations, multiple drawstrings loop around the orifice and may be individually tightened. Multiple drawstrings can provide an advantage of securing the orifice enclosure to the user's body at multiple locations in a generally vertical orientation (i.e. in a direction that is approximately orthogonal to a plane defined by the orifice) along the user's body. Furthermore, one drawstring (e.g. an upper drawstring) may secure a maximum diameter or circumference of the opening and the lower drawstring(s) may provide the sealing pressure of the flexible material of the seal surrounding the user's body. Multiple drawstrings may also serve to anchor the seal (e.g. fabric of the seal) to the body. As described, belts and draw strings are but one example and should not limit the type of securing apparatus for a seal having an adjustable orifice in a differential air pressure system.

Figure 5B:
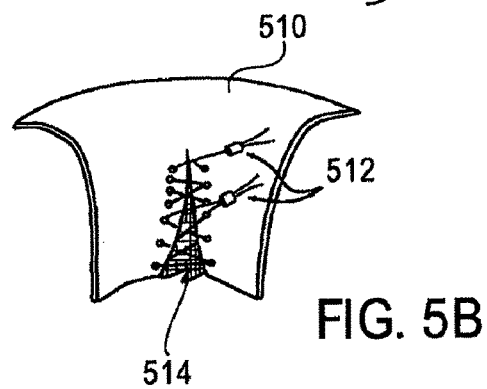

FIG. 5B illustrates another of an adjustable orifice seal 510 utilizing one or more laces 512 for adjustment of opening size. The laces 512 pull the fabric or other flexible material of the seal around the orifice together like a girdle. In one embodiment, the laces may reside along only a portion of the vertical surface of the opening. In one embodiment, the opening is constructed from a sufficiently airtight and flexible material, such as neoprene. Furthermore, additional flexible material 514 may be disposed between the laces 512 to maintain a sufficiently airtight seal over the laces 512. In one embodiment, multiple sets of laces may be distributed in more than one location around the perimeter of the opening.

Figure 5C:
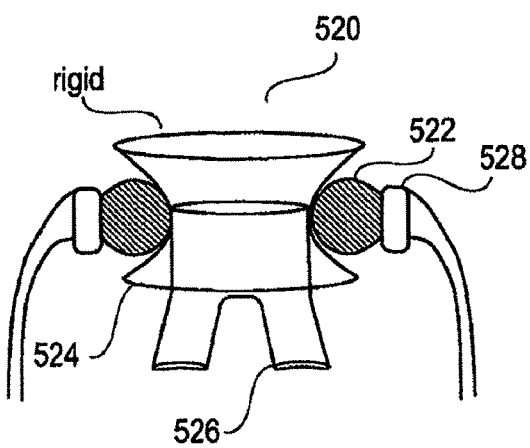

FIG. 5C illustrates another embodiment of an adjustable orifice seal 520 utilizing one or more expandable pouches 522. In one embodiment, the one or more expandable pouches 522 decrease the orifice circumference of an opening as pouches 522 are expanded to create a seal to a user 526. The pouches may be made of an expandable material such as rubber, neoprene, or other flexible airtight material. In one embodiment, the pouches are fixed to a stiff outer surface 528 attached to the enclosure or shell of a chamber of a differential air pressure system. The stiff outer surface 528, if present, limits the outward expansion of the pouches 522 when the pouches 522 are expanded, forcing the pouches to expand inward toward the user 526 around the perimeter of the user. The pouches may be filled with a substance such as air, other form of gas, liquid (e.g. water), gel, or other suitable substance to expand the pouches 522. The pouches 522, when expanded, fit against a shaped surface 524 that is attached in a sufficiently airtight manner to the user 526 thus effectively locking in the user and creating a seal. It should be noted that the seal 520 may allow for relative rotation between the stiff outer surface 528 and the one or more pouches 522, and/or relative rotation between one or more pouches 522 and the shaped surface 524, and/or relative rotation between the shaped surface 524 and the user 526. For example, in one embodiment, the surface 524 may comprise a low friction bearing coating, utilize bearings, or utilize lubrication to improve rotational properties of the user 526 when sealed in the orifice. In some variations, a second seal flap (not shown) may be disposed between the surface 524 and the expandable pouch or pouches 522 to enhance the sealing characteristics of this interface. By having pouches 522 that are initially unfilled, the user 526 can adjust his rotational position in the opening. The pouches 522 may then be filled to fit the user 526. The pouches 522 are backed by a constraining piece 528 that retains the position of the pouches 522 and limits outward expansion of the pouches. In one embodiment, the pouches 522 are filled and adjusted manually. In another embodiment, the pouches 522 are filled and adjusted using hardware, software, or a combination of both. In either case, the bags can be filled to levels according to sealing properties and user comfort.

Figure 5D:
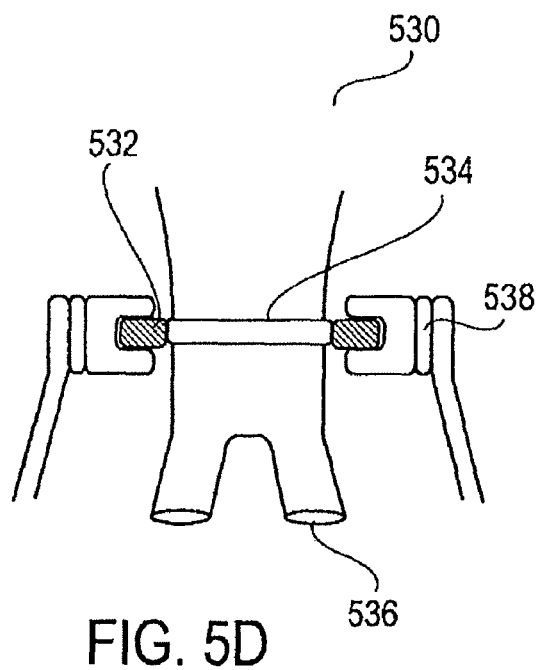

In some variations, one or more expandable pouches can be provided on either the enclosure of the chamber and/or on an attachment (e.g. shorts) worn by a user. FIG. 5D shows a cross-sectional view of a system where a stiff backing surface 534 and one or more expandable pouches 532 are disposed on the user 536, clothing worn by the user, etc. Pouches 532 expand against outer rigid surface 538 that may be attached to the enclosure of a differential air pressure system to seal the user 536 in the differential air pressure system. Similar to FIG. 5C described above, the expandable pouch or pouches 532 may rotate relative to the backing surface 534 and/or relative to the outer sealing surface 538.

Figure 5E:
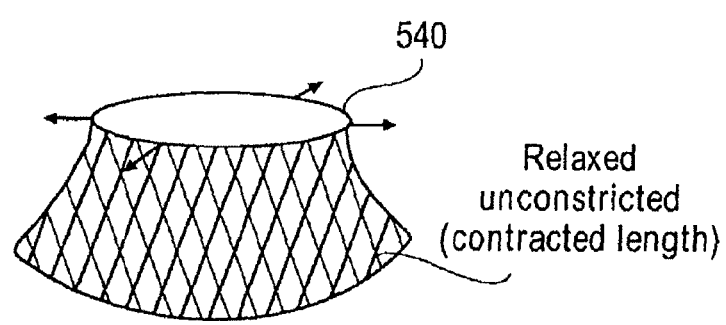
Figure 5E:
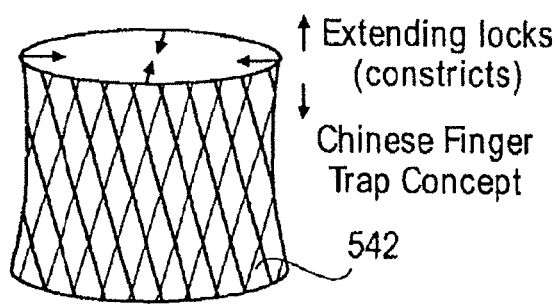

In one embodiment, a seal comprising an adjustable orifice is constructed in a weave similar to a Chinese finger trap to snugly fit individuals of varying dimensions, as illustrated in FIG. 5E. A Chinese finger trap is a woven cylinder that when expanded compresses radially. When a user is inserted into adjustable orifice seal as illustrated in FIG. 5E, and the seal is extended axially (e.g. from axially compressed configuration 540 to axially expanded configuration 542), a snug fit around a user can be created.

In some variations of woven adjustable orifice seals as illustrated in FIG. 5E, the weave is configured such that it will snugly fit around users having a variety of dimension, while also being easily releasable. In various embodiments, the weave can be an open weave or a closed weave, and can be constructed from any suitable material, e.g. a natural or synthetic textile. In some variations, the weave comprises NYLON™ polymer. Furthermore, in some variations, the weave can comprise a low porosity or non-porous overlay such as rubber skinned neoprene to assist with sealing and user comfort.

Figure 5F:
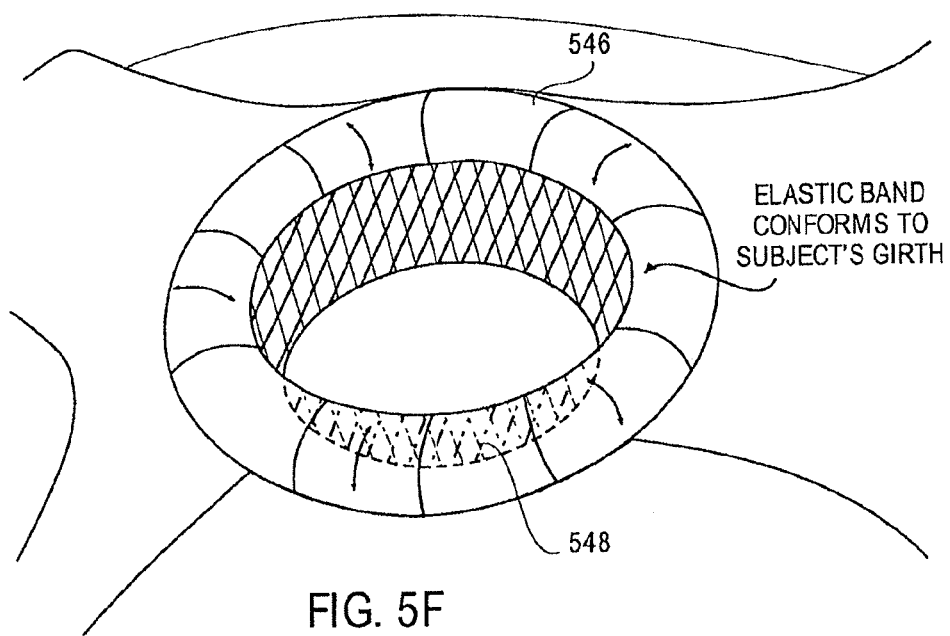

In another embodiment of an adjustable orifice seal as illustrated in FIG. 5F, an expandable band 546 may be used to adjust the size or shape of the orifice of the seal. By expanding a band 546 and allowing a user to insert himself into the orifice of the seal to enter the chamber, and then proceeding to release the band to close and conform to the body of the user, the user can be securely sealed in the chamber.

Any suitable expandable band may be used in adjustable orifice seals as illustrated in FIG. 5F. In one embodiment, the expandable band 546 utilizes an elastic band material that allows the circumference of the orifice to expand and contract. In some variations, expansion of the band 546 may be accomplished by a user squeezing his body into the orifice surrounded by the expandable band. In some variations, the expandable band may comprise an inflatable inner tube-like chamber 548 or other mechanical means that when inflated expands radially outward, and when released (deflated) urges the band 546 inward against the user. In certain variations, an expandable band 546 can comprise one or more deformable structures backed with an elastic band. The deformable structure may for example be formed from a material similar to foam or other conforming material that span the gap between the user and the elastic band. When the elastic band is released, the deformable material squeezes around the circumference of the user's body creating a sufficiently airtight seal.

Figure 5G:
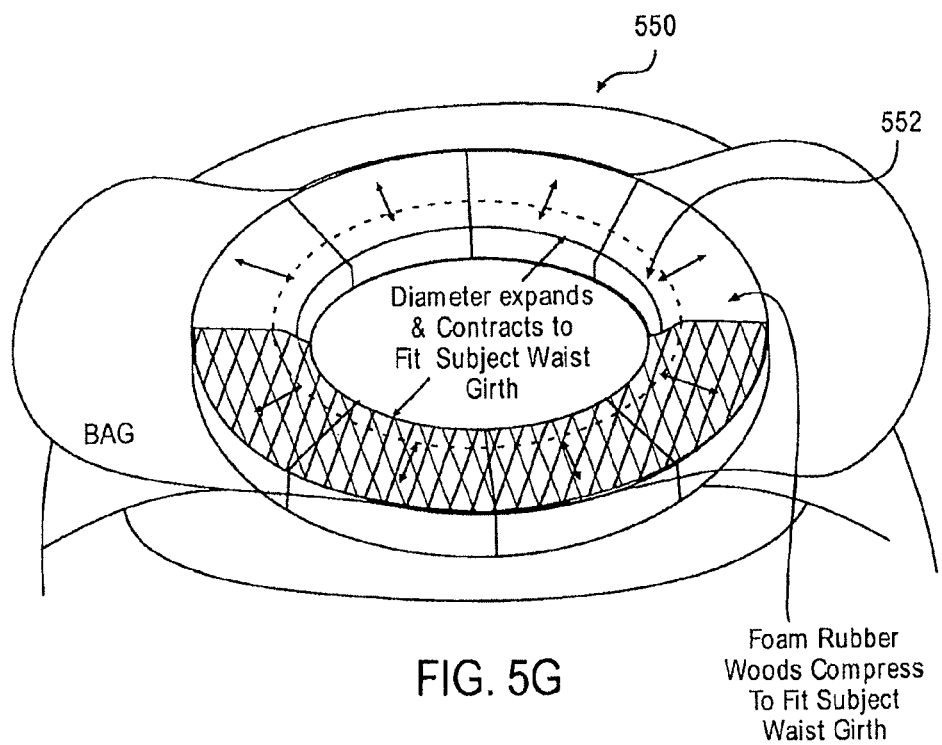

Yet another example of an adjustable orifice seal comprising an expandable band is illustrated in FIG. 5G. There, expandable band 550 comprises a deformable section 552 attached to springs (not shown). In some variations, the deformable pieces can be made to conform to the user's anatomy to create a seal. The springs (not shown) can be compressed and held to open the orifice for the user to enter, then released to create the seal. The deformable section 552 may comprise multiple, separable pieces of a deformable material, may be a unitary construction (e.g. a solid ring), or may comprise multiple pieces integrated together to form a single piece. In some variations, the deformable section 552 may be hollow, and the springs (not shown) may be disposed inside the hollow of the deformable section 552.

Figure 5H:
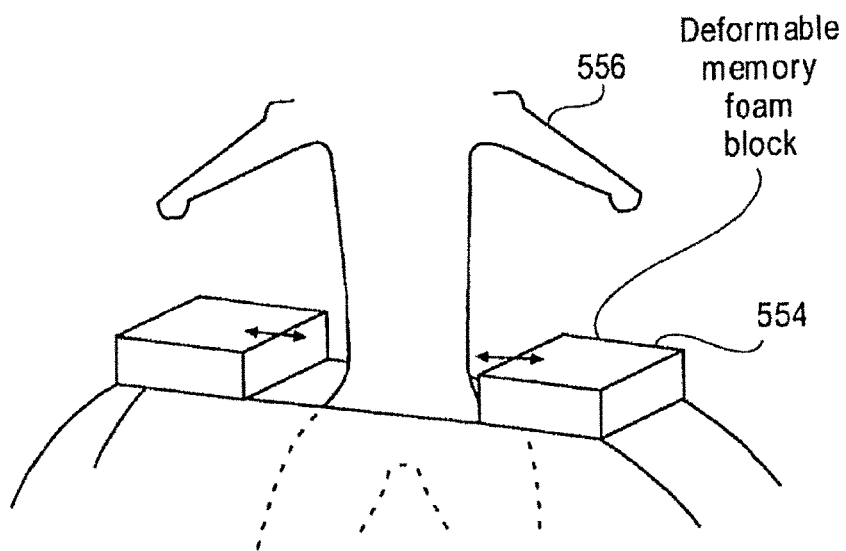

Other configurations and types of deformable structures can be used to adjust the size of an opening in a pressure chamber. In one embodiment, a deformable constructed form or shape-recovering material can be secured to all or part of a perimeter of the opening, and a user can deform the foam to get in the chamber. Once the user is in the chamber, a shape-recovering deformable structure, e.g. foam, will try to recover to its normal shape against the user, thereby forming a seal. In some variations, a deformable material may be permanently deformable and a molded insert specific to a user's body can be attached to the chamber prior to use and subsequently compressed around the user when the user enters the machine. FIG. 5H shows an example of a deformable material 554 that is compressed around the user's body 556 to span the opening of the chamber enclosure and to create a substantially airtight seal around the user. In one embodiment, the deformable material may recover its shape or form once released from the user's body (e.g. a memory material, foam, gel, etc.). In another embodiment, the deformable material is detachable, and specifically molded to the user's body. In some embodiments, compartments of deformable material, such as foam or gel, can be used for the same or similar purpose as shown in FIG. 5H.

Figure 5I:
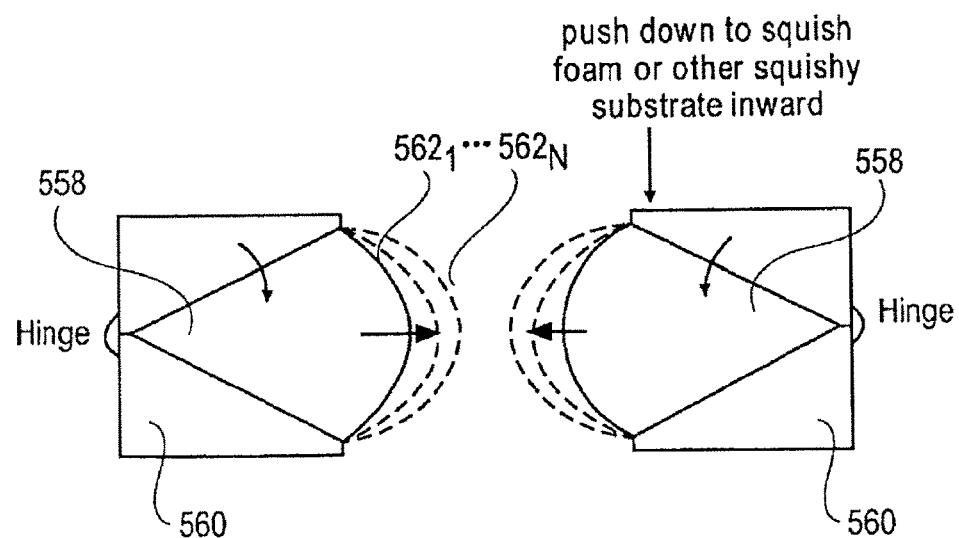

In one embodiment illustrated in FIG. 5I, deformable material 558 is disposed in a wedge-like volume between hinged elements 560. The hinged elements 560 may be wedges in some variations, but may have other than wedge shapes in other variations. By opening the wedge-like volume using the illustrated hinge, the deformable material 558 can be drawn outward (away from the user) (e.g. from position $562_1$ to position $562_N$), a larger orifice is created for a user to enter. By compressing the wedge-like volume between elements 560, the material is deformed inward (toward the user) (e.g. from $562_1$ to $562_N$) to form a ring-like seal against the user's body, thereby forming a sufficiently airtight seal. In some embodiments, the degree of compression of the hinged elements 560 may be controlled by, for example, a processor connected to a differential air pressure system. In some embodiments, the hinged elements 560 may be locked into one of a number of selectable positions corresponding to the amount of expansion of the deformable material required to seal to the user's body. In those embodiments, the hinged elements may be locked using any suitable locking element or locking mechanism, e.g. a pin, a clamp, a ratchet, or other locking mechanism described herein or otherwise known. Furthermore, in some variations, a separate insert (not shown) may be disposed around the user's body to create a smooth surface for the deformable material to compress against. If present, such an insert may form a sufficiently airtight seal to the user's body and may be sufficiently stiff to withstand the compression from the deformable material.

Figure 5J:
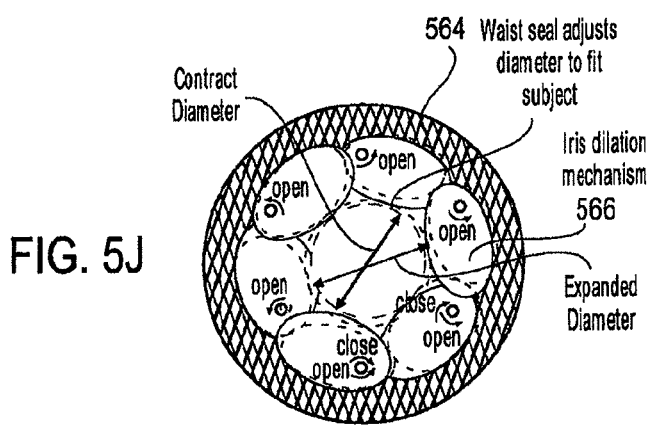

In one embodiment, as illustrated in FIG. 5J, an adjustable orifice seal 564 can be made adjustable by configuring the seal to include an iris diaphragm configured to form a sufficiently airtight seal against the user. In some variations, an iris used to make an adjustable orifice seal can include or be made from several stiff pieces of material, such as pieces 566, which are rotated open and closed to create a variable sized orifice. The stiff material may be a plastic, metal, or other sufficiently structural material that will not deform significantly under pressure. In one embodiment, the iris uses one or more locking mechanisms to keep the iris in an open, closed, or fixed in an intermediate position. Any suitable locking technique or locking device can be used, including pins, clamps, levers, or any other suitable locking mechanisms described herein or otherwise known. In some variations, a softer transition material (such as a rubber, fabric or leather) may be added to ends of iris diaphragm 566 components to form a softer interface between the iris diaphragm and the user's body to promote comfort and/or to improve the quality of the seal. For example, in some variation the iris diaphragm may be configured to be expandable from an approximately 12" diameter opening to an approximately 22" diameter opening to accommodate users of a wide range of body types.

Figure 5K:
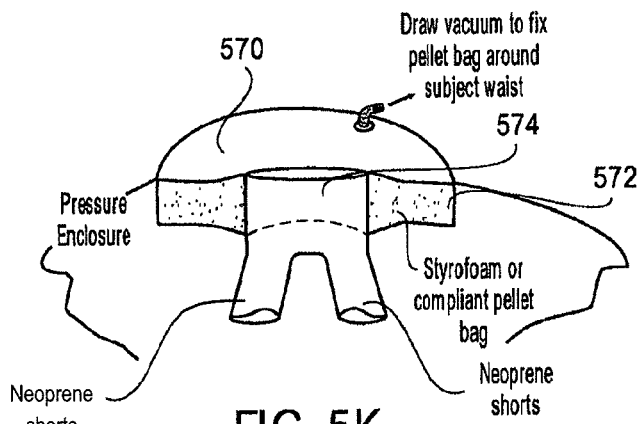

FIG. 5K illustrates another embodiment of an adjustable orifice seal 570 utilizing one or more bags 572 to seal against the user. In some variations, the bags 572 can be filled with pellets, and may be disposed around the perimeter of the user and attached to the pressurizable enclosure. In one embodiment, pellets in one or more bags 572 can be used to create a seal by applying a vacuum to the one or more bags. When air is removed from the bag, the pellets form a stiff surface that conforms to the user's body. The pellets can be constructed from any suitable material, e.g. plastic such as Styrofoam™ foamed polystyrene, glass, or other stiff material. Furthermore, the pellets are sized small enough that they form a contoured, stiff seal when put under a vacuum. The vacuum applied to the bag containing the pellets should be sufficiently strong such that it can pull the pellets to form a comfortable, stiff seal even when under pressure from the chamber. In one embodiment, a softer material 574 may be disposed between the body of the user and the bagged vacuum packed pellets to promote comfort during use and/or to enhance the seal between the user and the bagged vacuum packed pellets. The vacuum may be supplied by an external source such as a motor, a suction pump activated by the user, or other suitable means for pulling a vacuum in a bag or bags. In some variations, one or more components of a differential air pressure machine may be configured to supply a vacuum, e.g. a blower used to pressurize the chamber may be configured as a pump.

Figure 5L:
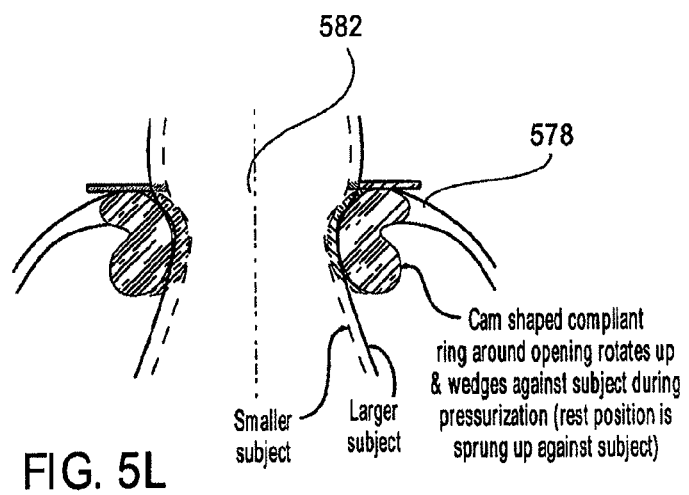

FIG. 5L illustrates another embodiment of an adjustable orifice seal 578 utilizing one or more cam 580. In this variation, one or more cams 580 are utilized to form a seal against the user 582. The cams 580 are shaped pieces that naturally have a center of mass that causing them to point downward. Their geometry can be formed in many different ways, but one end of their shape has a longer path around an axis than another part of the shape. If they are arranged in a loop configuration, this causes a larger diameter hole when they are pointed down than when they are pointed in towards the middle of the hole. When the user enters the opening, the cams either fall down or are already pointed downwards along their longest axis from their pivot points. When the cams 580 are pushed up, either by pressure, the user being raised, or through the use of a lever or the like, the cams are pushed up so that the circumference of the opening is reduced, forming a seal against the user. In one embodiment, the cams have a locking mechanism that keeps them in a stable orientation. Furthermore, a substantially airtight material (not shown) may be disposed between the cams to maintain a sufficiently airtight seal to the user. In one embodiment, the cams 580 are biased inward such that user 582, upon insertion of their body, pushes the cams 580 down and outward. The bias on the cams 580 causes them to create an initial pressure on the substantially airtight material spanning the cams 580, and therefore to create an initial seal to the body of the user. The air pressure within the chamber surrounding the user, when increased, can enhance the pressure on the cams 580 and therefore improve the seal.

Figure 6:
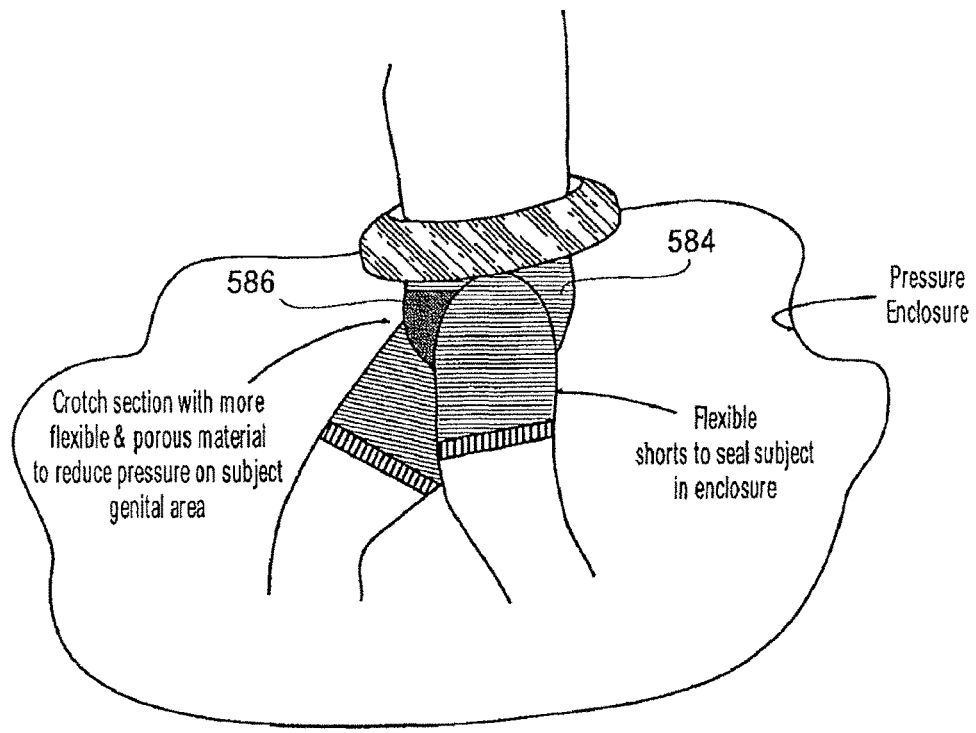
FIG. 6 illustrates one embodiment of user shorts.

In some variations, a pouch can be added to shorts worn by a user of some appropriate embodiments discussed herein to add comfort to the groin during use in a differential air pressure system. This pouch, if present, can be made using an elastic material. One embodiment of user shorts 584 with a pouch 586 is illustrated in FIG. 6. In one embodiment, the short may be constructed of a porous material that allows a pressure change, thereby reducing the pressure force around that area. This may be especially important for male users at low pressures.

Rotational Orifice Sealing

Currently devices that utilize differential air pressure technology for cosmetic, health, or fitness purposes are limited in the way that a user is able to move with respect to the pressure chamber. The chamber that has either a higher or lower pressure than the outside air allows a user to accomplish a variety of activities that can lead to bodily improvements. Currently, a user in one of these machines may want to increase their range of motion through allowing rotation of their body relative to the enclosure statically (i.e., prior to or after activity), or dynamically (i.e., during activity). A user seal that facilitates rotational movement is advantageous for many applications of differential air pressure technology. Dynamic adjustment gives the user the ability for a wider range of motion during their time in the chamber, and allows them to change position in the chamber without having to exit the chamber or to change a setting of the chamber. A rotational adjustment capability would allow users to perform normal forward motion, sideways motion, and backwards motion without having to adjust the direction or angle of the floor or moving surface underneath. While not required, further combination with a translational movement capability may also improve the experience and range of motion for a user inside a pressurized chamber. In one embodiment, one or both of the described rotational and translational movement capabilities may be assisted via automation, sensors, software, and/or hardware.

Figure 7A:
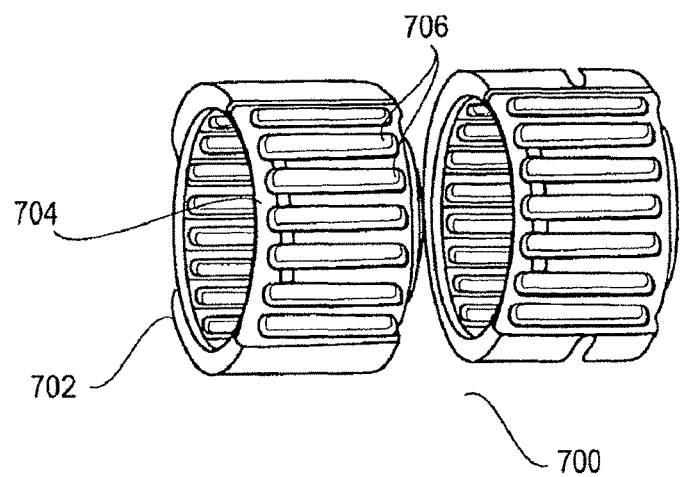
FIGS. 7A-7J illustrate various embodiments of rotational seals.

In one embodiment, a rotational seal is made via the use of bearings to allow a rotational motion about a seal in a differential air pressure system. In one embodiment, relative rotation motion of a user inside a chamber is enabled by disposing a bearing between the user and the enclosure. FIG. 7A illustrates one embodiment of a bearing enclosure incorporating needle bearings for use in a user seal in a differential air pressure system. For the particular example illustrated in FIG. 7A, the bearing enclosure 700 has an exterior tubular section 702 and an interior section 704 that is arranged in a concentric relationship with the exterior tubular section 704. The spacing tolerance between the outer surface of the interior section 702 and the inner surface of the concentrically arranged exterior tubular section 704 is such that the exterior section 704 is oversized just enough relative to the interior section 702 to accept insertion of a plurality of circumferentially distributed needle bearings 706 between those surfaces. Bearing enclosure 700 can be positioned around the user seal. As the user rotates and tries to move too far off-concentric from a center of the orifice in the chamber, the needle bearing resists this motion but the needle bearings (rollers) allow for rotation. The user is therefore kept generally concentric with the enclosure but is allowed to rotate freely. In some embodiments, a secondary seal (not shown), such as a flap seal or other sealing method described herein or otherwise known, may be used to seal the gap between the two concentric surfaces taken up by the needle bearing.

Figure 7B:
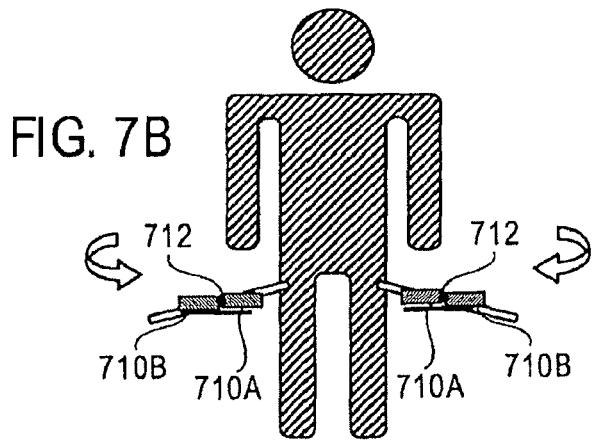
Figure 7C:
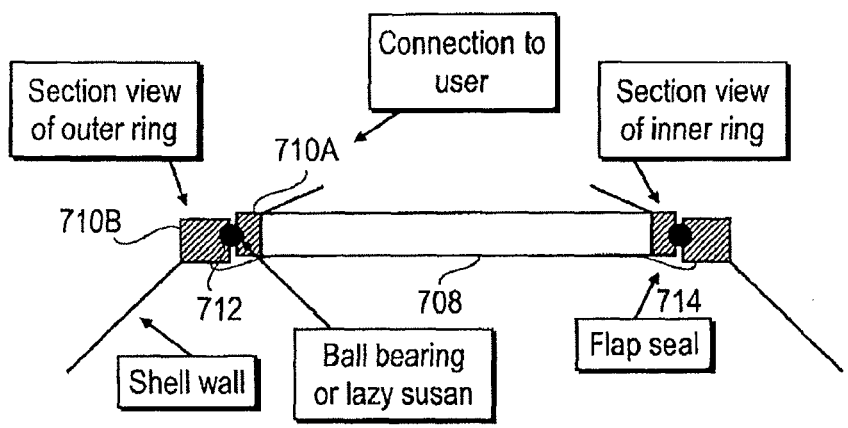

Rotation of the user relative to the enclosure can also accomplished by using ball bearings between layers of material. FIGS. 7B and 7C illustrates a section view of one embodiment of a seal 708 with bearings 712 between layers of materials 710A and 710B for use in a pressure chamber. A simplified example of ball bearings used between layers of material is a lazy Susan bearing. The lazy Susan bearing comprises concentric rings that are connected via multiple ball bearings that allow the two concentric rings to rotate relative to each other. The inner ring may connect to or contact the user via another medium (e.g. a fabric or rubber), and the outer ring may connect to the enclosure via a second medium. The bearing itself may be separable from the chamber but attachable to the chamber using a method described herein or otherwise known. In one embodiment, a flap seal 714 or other known sealing method may be disposed across the surfaces of the concentric rings of the bearing to seal the gap between the bearings. In one embodiment, a similar configuration may be used for a negative pressure chamber, when the flap seal is moved to the top surface of the bearing rather than the bottom surface. In one embodiment, the rotational seal 708 utilizes fluid bearings. There, by inserting a layer of gas or liquid, a bearing can be created that is useful for improving motion. The outer surfaces in such a bearing would be sealed to prevent leakage of the fluid.

Figure 7D:
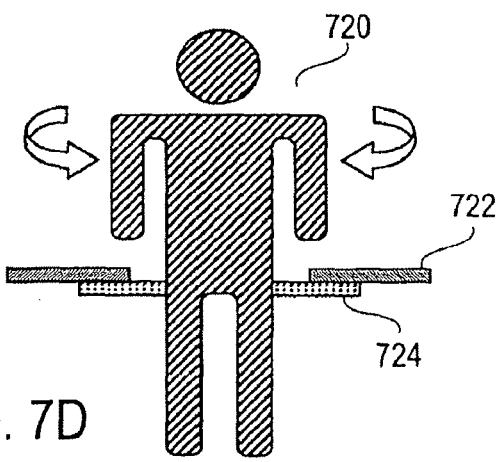

FIG. 7D illustrates another embodiment of a rotational seal 720 with one or more pieces of overlapping materials, illustrated as overlapping materials 722 and 724, with properties enabling them to spin relative to one another. In FIG. 7D, the multiple materials 722 and 724 are configured to overlap to create a seal between a pressure chamber and the outside, while allowing a user to rotate. The overlap may between two materials, as illustrated in FIG. 7D, or between more than two materials. The overlap may be between two pieces or between multiple pieces. In one embodiment, the relative rotational motion between the materials is achieved by sufficiently low coefficient of friction between the two surfaces of materials 722 and 724 (e.g., rollers or bearings between the two surfaces, or other known methods of allowing relative motion between two separate materials). In one embodiment, a rotational seal such as rotational seal 720 may include one or more stops, tracks, or guide surfaces to allow a specific rotational range of motion. In one embodiment, this rotational seal concept may be adapted to operate with a negative pressure inside the chamber, e.g. by putting the portion of the seal attached to user on the top surface of the chamber so that the vacuum within the chamber pulls the two surfaces together instead of pushing them apart.

In different embodiments, rotational seals may be configured via different geometries, as illustrated in FIGS. 7E-7I. In one embodiment, seal materials are configured in different geometries to take advantage of different variables such as the environment, pressure forces, chamber shaping, user motion, manufacturability, and cost. Some examples of these other geometries are cones, parabolas, semi-spheres, or hooking/locking mechanisms.

Figure 7E:
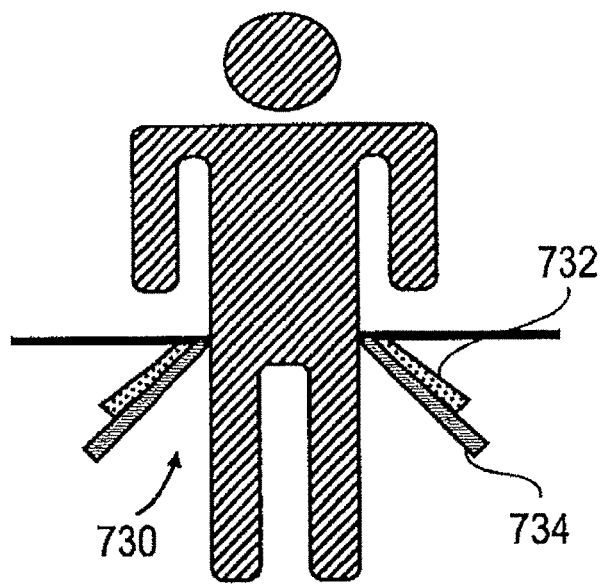

FIG. 7E illustrates a section view for one embodiment of a seal 730 of overlapping cones 732 and 734 that may rotate relative to each other. Overlapping cones are but one form of overlapping seal that may provide rotation.

Figure 7F:
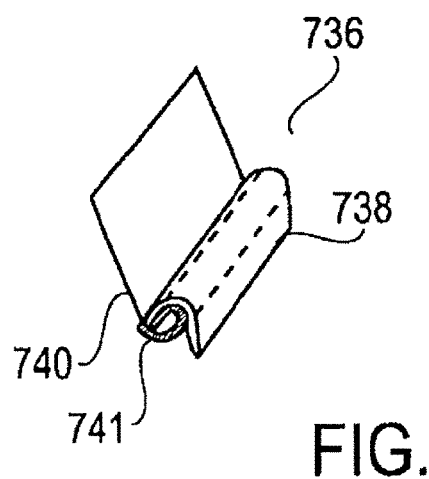

FIG. 7F illustrates one embodiment of a locking hook mechanism 736 that may be used to secure together two pieces 738 and 740 to form a seal around the circumference of an opening in a chamber. As illustrated, the first piece 738 has a hook-like cross-sectional shape that fits over the second piece 740. The second piece 740 can comprise a tube or rod (e.g. a plastic tube or rod) that may be part of a frame, or an extension of a frame. The tube or rod is sewn in the hem of a flexible shell enclosure 741. The locking hook first piece 738 is placed over the second cylindrical piece as illustrated, thereby forming a seal between first piece 738 and second piece 740 that allows for relative rotation between the two pieces 738 and 740 due to low coefficient of friction between surfaces of the two pieces 738 or 740 or due to any other technique that facilitates relative movement of the two pieces. Because the seal is formed by simply hooking the locking hook first piece 738 over the second piece, this variation of rotational seal allows relative quick sealing of a user into a chamber.

Figure 7G:
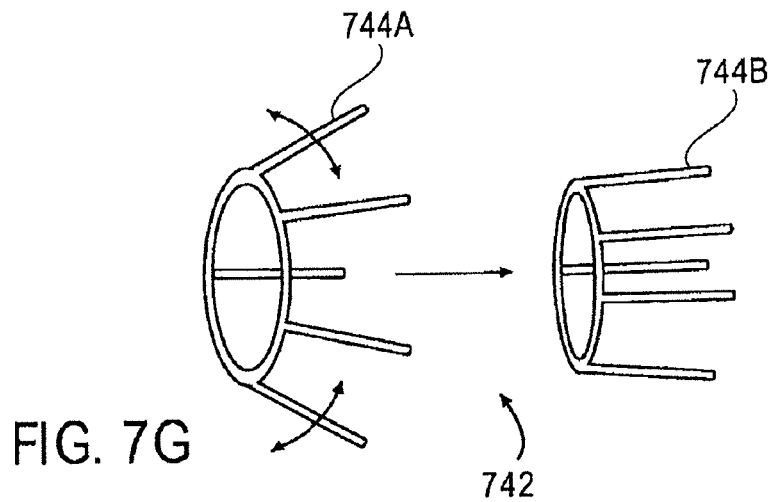

FIG. 7G illustrates one embodiment of a deformable insert 744A-744B. The deformable insert 744A-744B is configured to drop inside an orifice or to reside on a top surface of a pressurizable chamber and be positioned over an orifice of the chamber. The deformable insert may be constructed from stiff but deformable materials such as plastic, flexible materials such as neoprene, or a combination of both stiff and flexible materials. FIG. 7G shows an exemplary embodiment of a deformable skeleton 744A that would be spanned with a flexible sufficiently airtight material. The skeleton 744A would be deformable to a shape 744B with a smaller outer dimension and when released spring back 744A to achieve a larger outer dimension. The material that spans the gap in the chamber may be sufficiently airtight and must seal to both the chamber and the user. This deformation allows for insertion into an opening of a pressurizable chamber and the subsequent expansion provides overlap to create the seal to the enclosure.

Figure 7H:
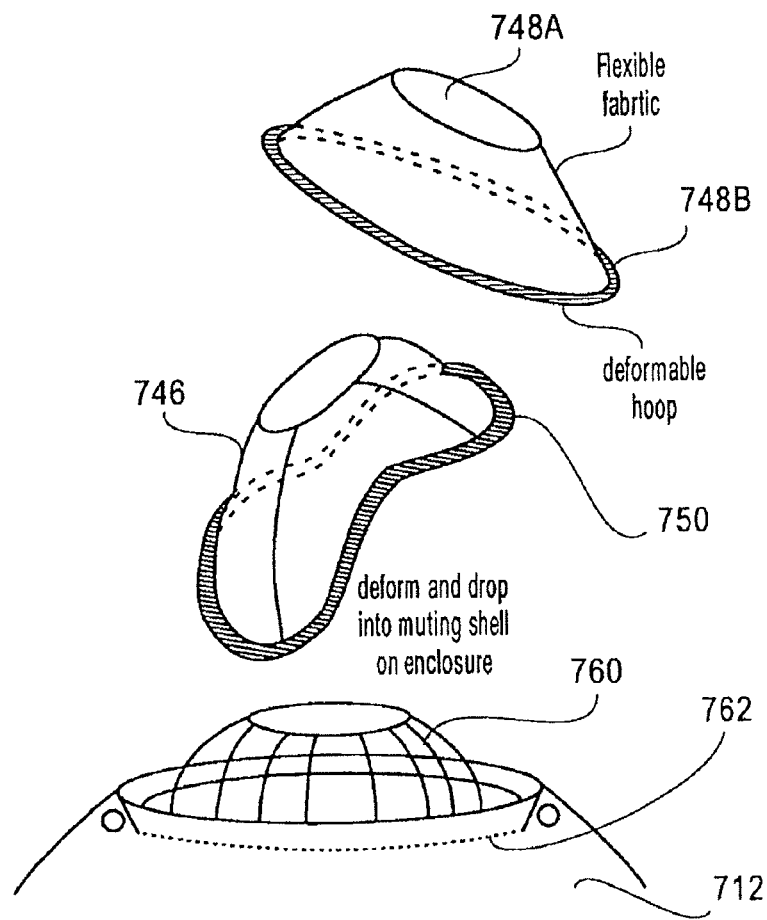

FIG. 7H illustrates another embodiment of a deformable insert 746. As illustrated in FIG. 7H, a rigid portion of insert 748A is an outer ring 748B positioned at the base of a flexible material constructed in a conical arrangement. The stiffer outer ring may be bent inward as illustrated to adopt configuration 750 to drop through the opening of a pressurizable chamber 762. Once dropped through the opening of the chamber, the insert may subsequently adopt expanded configuration 760. In one embodiment, the stiffer outer ring 748B may be shaped with a hooking shape such that it mates with an inner surface of the chamber 762, to enhance locking to the chamber 762 and to prevent the insert from separating and exiting the chamber as pressure is increased. In one embodiment, magnets or other attracting means may be used to enhance the seal during lower pressure operation by attracting the ring and/or a flexible portion of the seal to the inside or outside of the chamber. In other embodiments, buckles, straps, or other fastening devices may be used to secure the ring to the exterior of the chamber 712, e.g. to provide support for the user should the user fall and begin to drop through the orifice of the chamber. In a negative pressure system configuration, a deformable insert (similar to insert 746 illustrated in FIG. 7H) may reside on a top rigid surface of the pressure chamber, thereby preventing the deformable insert from being sucked through the opening under a vacuum; so that the deformable insert is essentially functioning as a cap to the chamber in a similar fashion described above. This can allow the user to easily enter the chamber and still provides a user seal that keeps pressure in and allows for user rotation.

Figures 1, 7I:
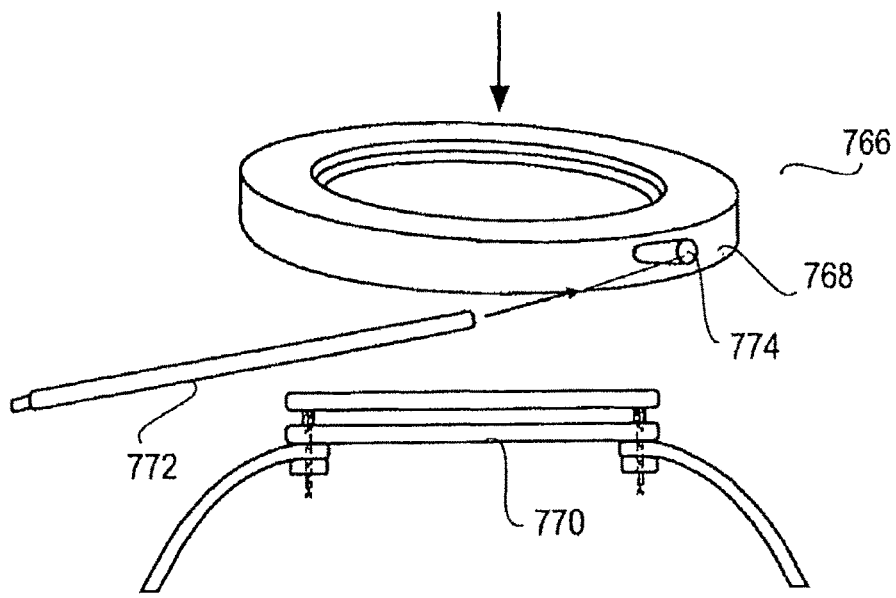
Figures 2, 7I:
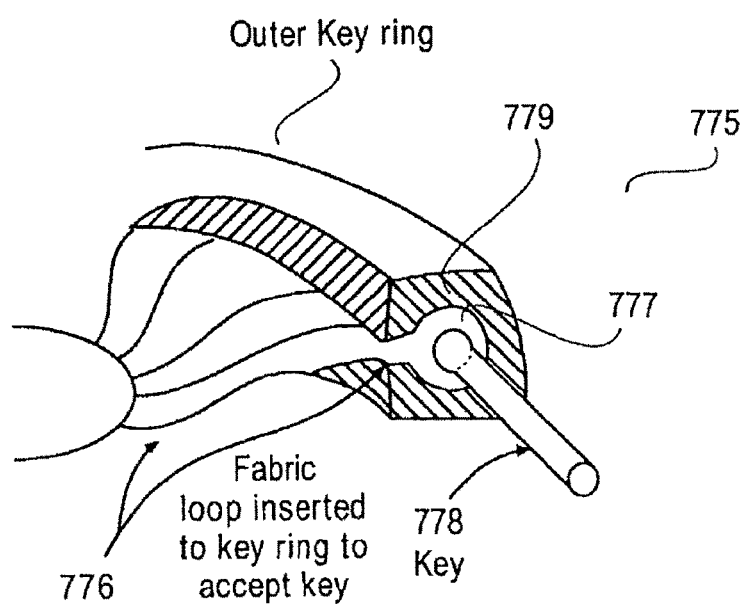

FIG. 7I-1 illustrates another embodiment of a rotating seal 766. In this particular example, the rotating seal comprises two separating pieces, an upper piece 768 and a lower piece 770, that when joined form a keyway 774, and a fitting "key" 772 that is insertable into the keyway 774 such a manner as to allow for rotation of one of the pieces 768 and 770 relative to the other, while anchoring a user in the orifice in a way that also retains pressure in the chamber. In the illustrated embodiment, the upper piece 768 including one half of a keyway 774 is lowered over the lower piece 770 which includes the other half of the keyway 774. When the two pieces are connected, a circular passage around the circumference of the seal is created. A key 772 (e.g. a round key) is inserted into the slot, locking the pieces together. To rotate the seal, the user may be connected to the upper or lower piece with the enclosure connected to the other of the upper and lower pieces. As the user attempts to rotate, the circular key allows movement of one piece relative to the other without breaking the junction or the seal. This seal can be constructed in a way that allows it to spin. In one embodiment, a secondary seal, for example a flap (not shown), may be disposed between the two halves that create the rotational seal 766 to maintain a sufficiently tight seal during rotation.

In another embodiment of a rotational seal 775, illustrated in FIG. 7I-2, a loop 777 of fabric 776 on the user side of the seal is inserted into a slot that runs the circumference of a stiff channel 779 attached to the top of the enclosure of a differential air pressure system. The key 778 is then pushed through the loop 777 of fabric 776, causing the loop 777 of fabric 776 to expand within the slot, which prevents the loop 777 from exiting the slot. Similarly, in other variations, a seal may be created if the loop is not necessarily made from fabric, but is made from a material which deforms and seals to the stiff chamber on the enclosure.

Another embodiment of rotational seal comprising a "key" rotation and locking mechanism is to create a stiff circumferential cavity around the user's waist such as depicted in FIG. 5C, discussed above. An expandable material, which may be an inflatable ring, is disposed around the perimeter of the chamber such that when the expandable material is expanded, it fills a portion of the cavity around the circumference of the user. This expandable "pouch" creates mechanical interference with the cavity surrounding the user which in turn causes a seal to be created as pressure is increased or decreased inside the chamber. A secondary seal may be included between the cavity and the expandable material to enhance the seal between these two parts. The expandable "pouch" then acts as the "key". The expandable material can be disposed on either the chamber or the user. An example of an expandable material comprising expandable pouches residing on the user side of the seal is illustrated above in FIG. 5D. In this embodiment, the circumferential cavity resides around the perimeter of the opening in the enclosure. The user inserts himself into the opening and expands the material that is disposed around the perimeter of the user seal until the expandable material (e.g. pouch or chamber) fills a portion of the cavity, thus securing the user seal to the chamber.

Figure 7J:
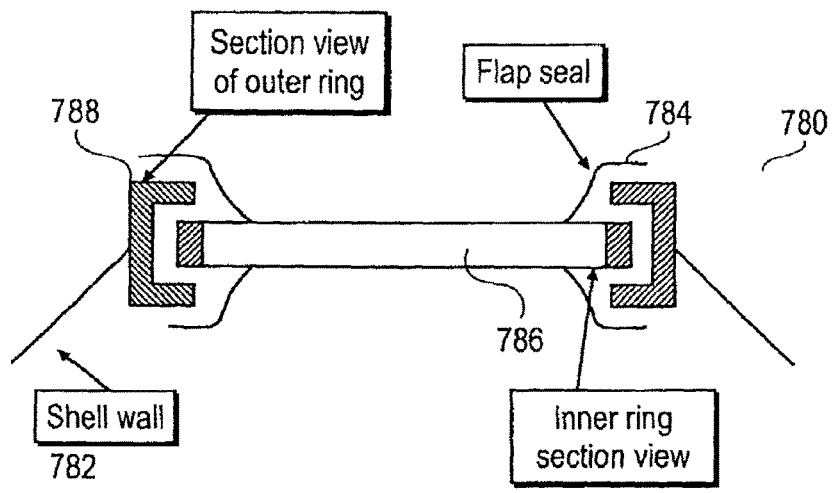

Rotating user seals, as discussed herein, may either be used alone or along with other known sealing methods to create a pressure seal that rotates, such as a flap seal a shown in FIG. 7J.

FIG. 7J illustrates a cross-sectional view of an adjustable orifice rotational seal 780 in accordance with one embodiment. In this particular embodiment, an outer wall ring 788 is built into, or coupled with, a shell wall 782 of a differential air pressure system, such as those described above with respect to FIG. 1 and FIG. 2. In the illustrated embodiment, a ring 786 slips inside a U-shaped channel in the outer wall ring 788. In some variations, the adjustable orifice rotational seal 780 further includes a flap seal 784 on the underside and top of ring 786. In one embodiment, under pressurization (either positive or negative) the flap seal 784 enables a sufficiently airtight seal of the adjustable orifice rotational seal 780, but allows a user to rotate in the orifice, when attached to the orifice by, for example, the inverted orifice skirt of FIGS. 3 and 4A-4B.

As can be seen in the cross sectional view of FIG. 7J, when the chamber sealed with the inner ring 786 is pressurized, the pressure inside the chamber created by shell wall 782 will suck or push the inner ring 786 against the surface of the outer wall ring 788 to form an airtight seal. Those of ordinary skills in the art will recognize that there are other ways of creating a spinning ring. In one embodiment, the inner ring 786 and outer ring 788 may be made of a plastic, metal, or other sufficiently stiff material. The flap seal 784 may be made of any rubber, fabric, or other suitable sealing material.

Translational Orifice Sealing

Enabling translational movement of a user relative to a base of a differential air pressure system may be desired in certain circumstances. For example, by adding one or more translational elements to a differential air pressure system, a user can experience a wider range of movement options, which can make differential air pressure technology more widely applicable and potentially more useful. The goal of the differential air pressure experience is to provide the unloading on the individual's body weight while restricting natural body movement as little as possible. Thus, allowing the user to translate along one or more axes is a step toward more degrees of freedom and an overall more natural experience during exercise. As used herein, a longitudinal axis of a chamber is meant to refer to a user moving in a forward or backward direction, relative to the user.

Figure 8:
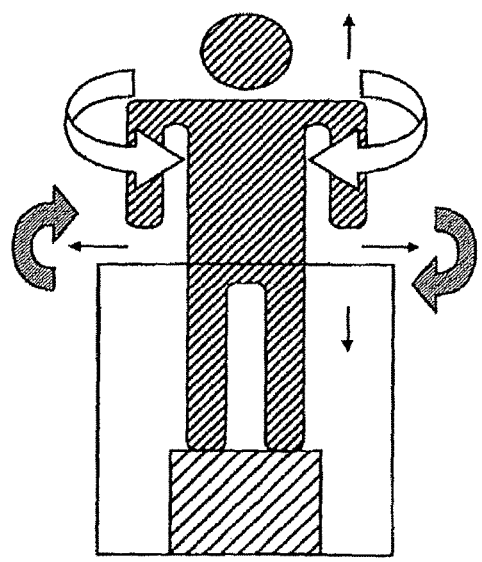
FIG. 8 illustrates various ranges of motion for a differential air pressure system.

Translational motion in a differential air pressure system may be accomplished in a variety of ways. Two broad categories can be considered: discrete translation, and dynamic translation. A discrete translation system refers to a variation in which the user can change translational position, but halts exercise to change position. A dynamic translation system refers to a variation in which the user has the ability to adjust position "on the fly," i.e., without halting exercise. The methods of accomplishing translation discussed below may be constructed in either a discrete or dynamic configuration. Other methods of motion, such as rotational motion, may be combined with translational motion to enhance the users experience and freedom of natural body movement as shown in FIG. 8.

FIG. 9A illustrates an example of a rail system 900 to enable translational motion in a differential air pressure system seal, e.g. along a longitudinal axis of the chamber. Rails 902 may be connected to one or more sides of the seal (user side or chamber side). A material 906, which may be a stiff or soft material, is disposed between the user's body (not shown) and the rail or rails 902. The material 906 may be attached to the user by friction, belts, straps, or any other methods of attaching to a body described herein or otherwise known. The material 906 may also be attached to the rails in such a manner that the material is allowed to translate along the length of the rail or rails. This translation is allowed due to a sliding motion of a suitably low friction interface between two surfaces, a rolling motion accomplished with wheels or castors, or other known methods of allowing materials to translate relative to one another. A flexible and sufficiently airtight material 904 is disposed between the user and each end of the rail 902 such that as the position of the user's body changes relative to one end of the rail or rails, the flexible material 904 expands on one side and contracts on the other side to maintain a closed opening along the length of the rail maintaining the air seal. As the user translates in a direction, forward for example, the wheels or castors are forced in that direction as well, thereby moving the seal. A seal may be disposed along the perimeter of the movable opening between the shell and all moving parts. Such a seal may be constructed of a flap seal or other form of seal described herein or otherwise known.

In one embodiment, the rail concept may be applied in more than one direction simultaneously, where one rail system slides within another rail system, e.g., like a laser cutting machine. For this embodiment, the same principles described above for maintaining a sufficiently air tight top surface during translation apply. The translation motion may be induced by the user's body, or assisted by a motor or other actuator, or a combination of manual or assisted operation. For example, an assistive actuation system may sense a user movement and react to assist the user in translating the seal opening in that direction at an appropriate rate.

Figure 9B:
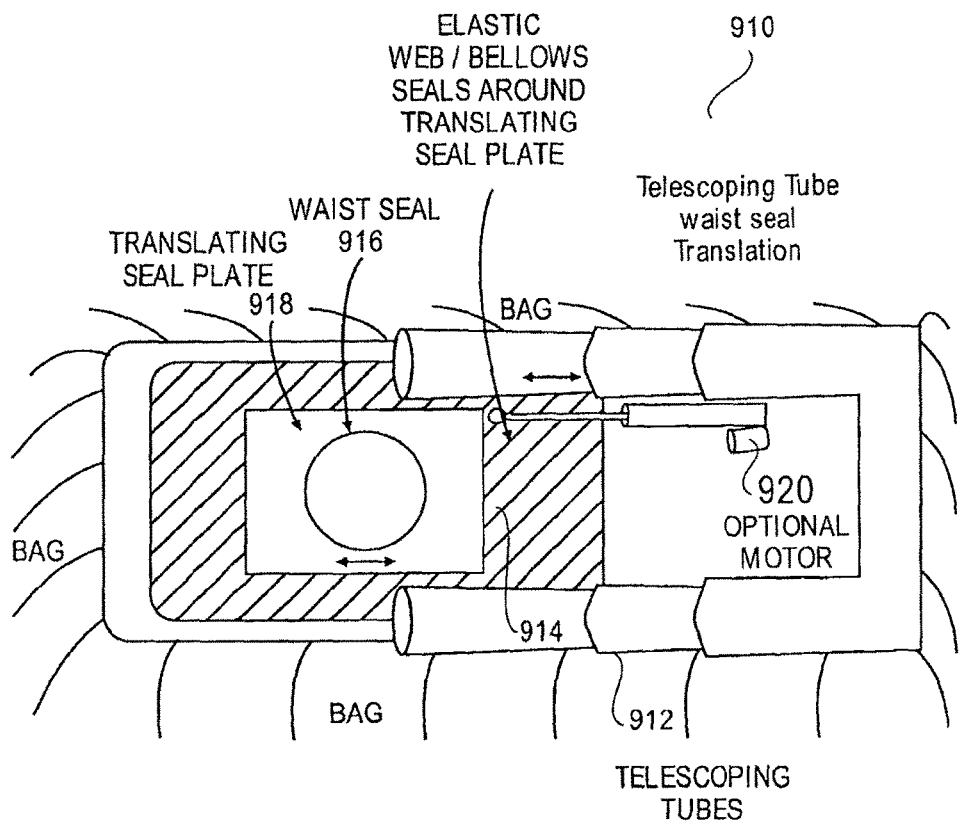

FIG. 9B illustrates telescoping members to enable translational motion in a differential air pressure system seal, e.g. along a longitudinal axis of the chamber. In one embodiment, one or more telescoping members are fitted inside one another and allowed to slide in and out, thereby allowing translational motion. In one embodiment, the motion of the telescoping pieces or members in a seal is assisted by including low friction materials, or by using bearings, fluid bearings, magnetism, and/or lubrication to assist in the telescoping motion. FIG. 9B illustrates telescoping members 912 on one side of the user's body. Another set of telescoping members 912 may be disposed on the opposite side of the user's body. A center portion 918 is attached to the user's body and one or more of the telescoping members 912, such that the center portion 918 translates along with the telescoping members 912. A sufficiently airtight flexible material 914 can expand and contract (e.g. a flexible material that can fold, or an elastic material that can stretch) as the center portion translates, while maintaining sufficient integrity in the seal. The telescoping members may be combined in such a manner so as to enable telescoping in multiple directions. In some variations, telescoping motion, e.g. multi-directional telescoping motion may be assisted by an actuation system 920 as described herein.

Figure 9C:
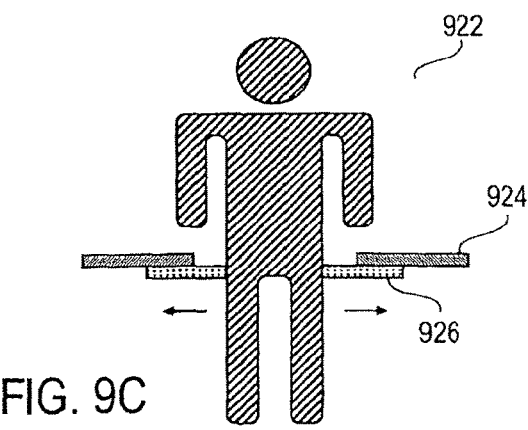
Figure 9D:
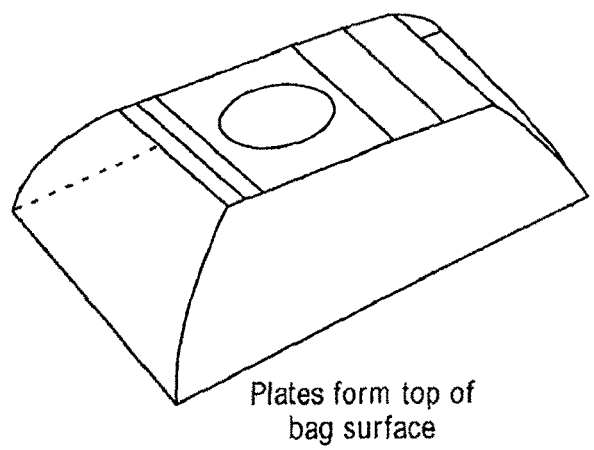
Figure 9D:
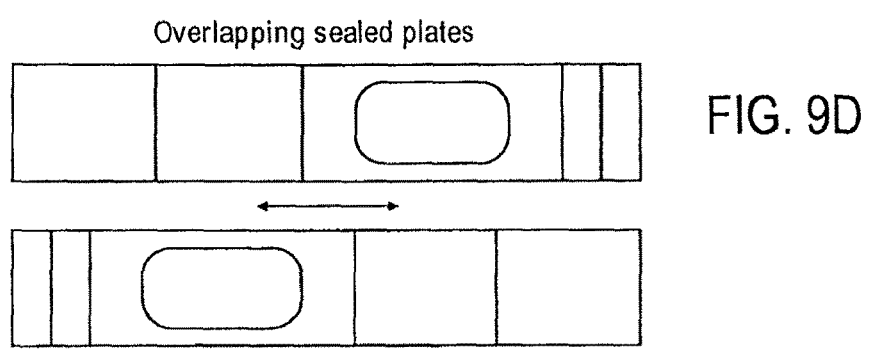
Figure 9E:
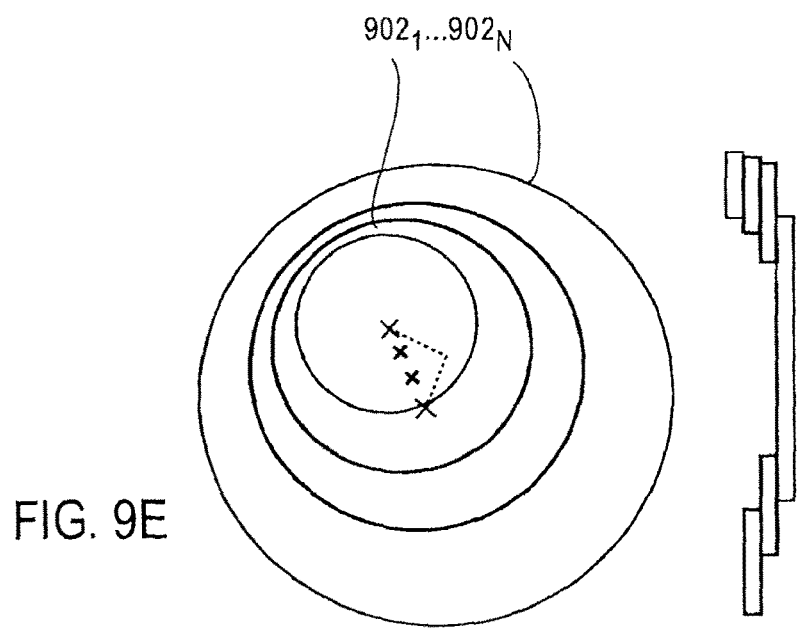

FIG. 9C illustrates another embodiment of a translational seal 922 with overlapping materials or structures 924 and 926. Other non-limiting examples of overlapping material geometries for a seal are illustrated in FIGS. 7D, 9D, and 9E. In various embodiments, these overlapping materials used to create a translational seal can be formed into a variety of geometries to allow for different ranges of motion. FIG. 9C illustrates one embodiment of multiple overlapping plates 924 and 926. The plates 924 and 926 can have a rigid border and flexible center in some variations, or may be fully rigid in other variations. In one embodiment, the seal 922 may also include a flap or other sealing method disposed on the overlapping edges of plates 924 and 926 to maintain a sufficiently airtight seal under pressure and during motion. In one embodiment, magnets or other attractive means may additionally be used to keep the sliding portion and the chamber close together, e.g. under low pressure conditions.

Non-limiting examples of geometries for overlapping materials or structures include rectangles, circles, ovals, etc. FIG. 9E illustrates one embodiment of overlapping plates $902_1$ to $902_N$ (which may or may not be circular as illustrated). The overlapping plates $902_1$ to $902_N$ may allow translational motion in all directions simultaneously. A flap or other sealing method may be disposed around the perimeter of the overlapping plates $902_1$ to $902_N$ to maintain pressure inside the chamber during motion. In some variations, there may be one or more stops or limits, or a track or a boundary to constrain the piece attached to the user via a seal from traveling too far, thereby creating a gap between the overlapping pieces. In another embodiment, the position of the overlapping pieces, e.g. as illustrated in FIG. 9E, may be reversed in conjunction with a negative pressure chamber to create a seal under vacuum conditions.

Any of these overlap methods to create a translational seal can use bearings, fluid bearings, magnetism, or lubrication to assist in either sealing or motion. Furthermore, overlapping materials can be either stiff, flexible, or a combination of both. For example, a translational seal can be formed using a deformable angled shape, e.g. such as that shown and described above in connection with FIG. 7H. The angled shape when not deformed may resemble the contour of the inside of the shell and be of sufficient size that when inserted into the shell there is mechanical interference between the shell and the angled shape. The angled shape may be made from or comprise any suitable material, e.g. a flexible fabric such as neoprene, or may be a deformable plastic or other flexible material. The angled shape may have a lip around the base that may mate with a lip on the shell enclosure to assist in locking the two pieces (the angled shape and the shell enclosure) together when pressure is applied inside the chamber. The material which forms the angled shape may form a seal by virtue of its flexibility and airtight qualities, or there may be a flap or other sealing mechanism disposed between the perimeter of the angled shape and the shell of the enclosure. The center hole of the angled shape may be configured to seal to the user's body by a method described herein or otherwise known. Deformation of the angled shape can allow for easy and simple access to coupling the user's body to the enclosure, which can speed time to exercise and facilitate de-coupling from the chamber, e.g. in an emergency. Magnets or other means of attracting or coupling the angled shape to the shell may be used to assist in creating a seal under low pressure operation. Such systems may be configured to allow for rotation between two substantially low friction surfaces or translation achieved by the same means.

Figure 9F:
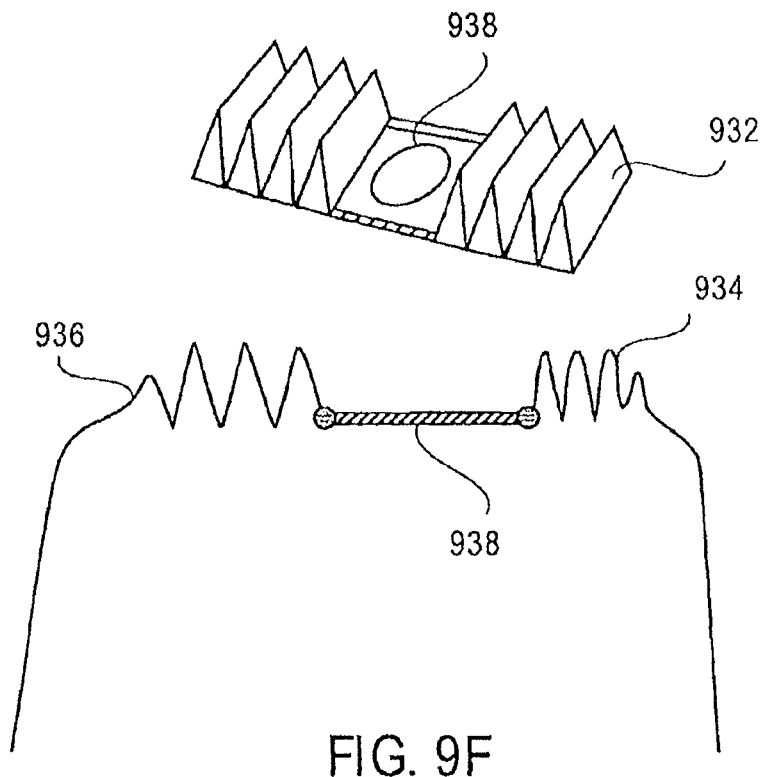

FIG. 9F illustrates another embodiment of a translational seal that utilizes a folded material resembling a bellows. In the example illustrated in FIG. 9F, two separate bellows 932 are disposed on either side of the user's body and connected by a center portion 938 into which a user (not shown) may be inserted and an airtight seal created via, for example a skirt, or other seal described herein or otherwise known. A rail system, similar to that discussed herein, is disposed along the length of the opening, and the bellows 932 and center portion 938 translate along the rail system as the user translates during motion. As the user translates, one bellows contracts 934 as the other expands 936, thereby maintaining full coverage of the opening during motion and maintaining a sufficiently airtight seal around the perimeter. One or more sections may be used in the bellows. As more sections are used, the material may become lower in height as each portion has a shorter distance to cover, thus becoming less obstructive to a user. In one embodiment, a sealing method such as a flap seal or other known sealing method may be disposed along the perimeter of the rails to maintain a sufficiently airtight environment inside the chamber.

Figure 9G:
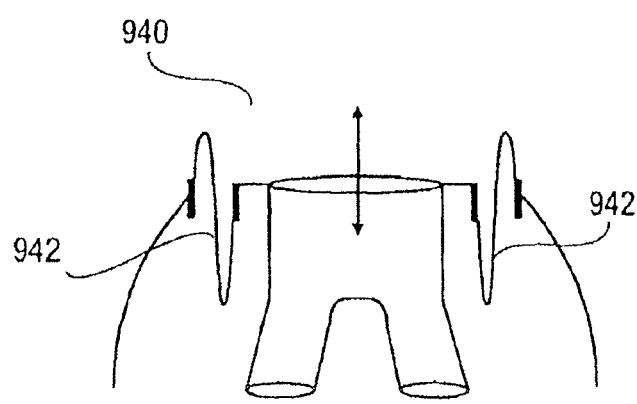

Translational motion may occur in one or multiple planes in various embodiments of a differential air pressure system. This may be advantageous in an air pressure chamber where exercises are to be performed required significant vertical movement such as jumping, squats, assisted pull-ups or dips. One way to allow vertical translation is to use extra material to create a flexible rolling diaphragm, sometimes seen in piston/cylinder configurations. One embodiment of a user seal 940 enabling vertical translation is illustrated in the section view shown in FIG. 9G. A flexible flap 942 is extruded around the perimeter of the piston or user's body to create a rolling diaphragm around the perimeter of the user. As the user's body translates up or down, the flexible material unrolls to allow for movement and rolls back to opposite direction when the user's body switches direction. The outer opening of the shell may be preset or adjustable by any means described herein or otherwise known. By restricting the outer dimensions of the opening, the force from the pressure on the rolling diaphragm is minimized because there is a very low surface area to act upon and the stiffness of the material of the diaphragm may hold the diaphragm from expanding and forming a large balloon inside or outside the chamber depending whether positive or negative pressure is applied inside the chamber. The diaphragm may be attachable to the user by any means described herein or otherwise known. In one embodiment, this configuration allows for vertical translation with respect to the chamber.

In one embodiment, these translational seals and related methods can be used alone or along with other seal features or sealing methods as described herein or otherwise known to create a pressure seal that translates. Examples of secondary seals are flap seals. Furthermore, these translational seals and methods utilizing the translational seals may be used alone or in conjunction with any of the other concepts described herein.

Secure Anchoring Seal

As described herein, the effectiveness of differential air pressure technology, which involves a user in a pressure chamber, is partially dependent on how the user is able to seal in the pressure chamber. The ability of the user to get in and out of the chamber also can determine how positive the user experience is.

In one embodiment, a user may be connected to a pressurized chamber by using adhesives. Application of the adhesive to the user or to a piece of clothing on the user would allow a seal to be created simply. One or more layers of tape could be used to attach a person to the chamber opening, creating a quick seal. Solvent based glues that dry are also possibilities to attach a user to the chamber.

In one embodiment, the pleated, or zipper, inverted skirt of FIGS. 4A and 4B are utilized to enable a user to quickly size the seal around them. The inverted skirt can in some variations be constructed from a stiff but deformable material, a flexible deformable material, or a combination of a stiff but deformable material and a flexible deformable material. The flexible deformable material allows parts of the skirt to be folded when necessary. These folds can cause the inverted skirt to attach and seal to the body. By attaching zippers or other closing mechanisms that allow the folding or unfolding of the inverted skirt, a user can choose what parts of the skirt need to be tightened and which do not. Additionally, in some variations, a high friction material or an adhesive (e.g. a spray-on adhesive or tape) may be disposed on the inner surface of the inverted skirt to increase grip on the user and to help prevent the user seal from separating from the user's body under pressure.

An aspect of many sealing methods the contact the body only around the user's waist is that they may "blow out" when under higher pressures or ride up on the user's body during movement. The seal deforms, or reverses, to a form where it can no longer hold pressure. One way of countering this problem is to seal a user to the chamber with vertically overlapping surfaces that attract one another. This allows a user to drop into the opening, but then would be sealed to the chamber.

A user seal that resists "blow out" as described above can be accomplished by any suitable method, including the use of high friction or "sticky" surfaces, Velcro™ type closures, material interactions that take advantage of van der Waals type forces, or magnetism to adhere a portion of the seal to the user, to the user's clothing, or to another portion of the seal, or to a portion of the chamber. Two surfaces can interact on their own to create a user seal, or they could be assisted. For example, a drawstring or other band may be used to pull together two high friction materials to secure the user into a differential air pressure system. A drawstring can restrict the outer diameter of the opening through which the inverted skirt would need to blow out and if tightened against the user's body there will be no space for the inversion to occur. Other methods beside a drawstring could be used to help the mechanical interference such as a rod or other keyway to lock the top of each seal material to each other so that the "sticky" surfaces do not also have to withstand the vertical force, which is the force that causes a "blow out" scenario.

Figure 10A:
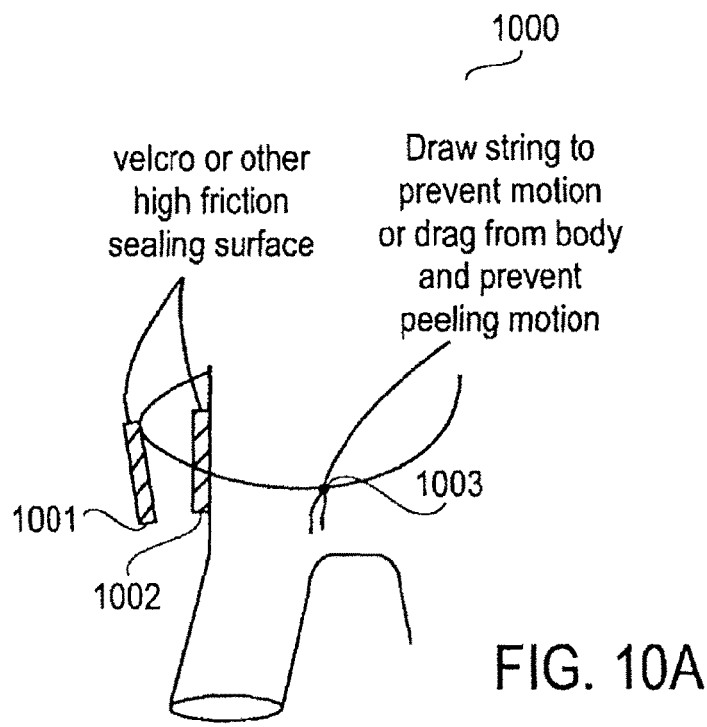
FIGS. 10A-10C illustrate various embodiments of mechanisms to grip the user's body and create a sufficiently airtight seal.

FIG. 10A illustrates one embodiment of a sealing mechanism 1000 for a differential air pressure system where a sealing flap 1001 is attached to the chamber and comes in contact with a mating flap 1002 attached to the user, and the mating is assisted and vertical force constrained by use of a drawstring 1003. (For example, FIG. 5B illustrates one embodiment of a laced seal attachment). In certain variations, the drawstring 1003 helps ensure the integrity of a multi-layer user seal, by preventing sealing materials from peeling away from one another.

Figure 10B:
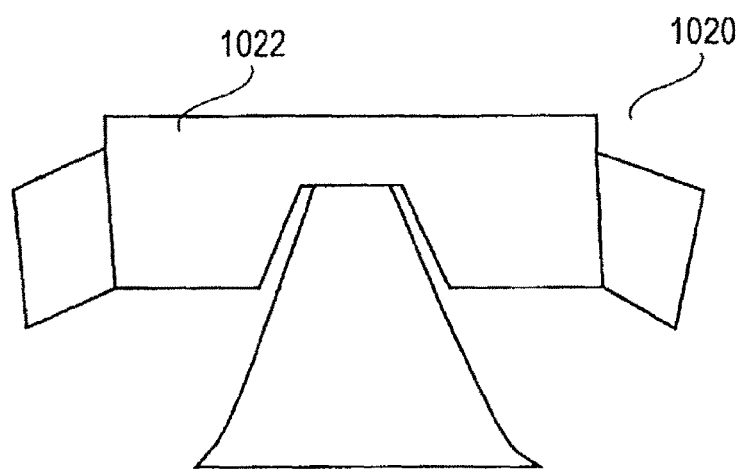
Figure 10C:
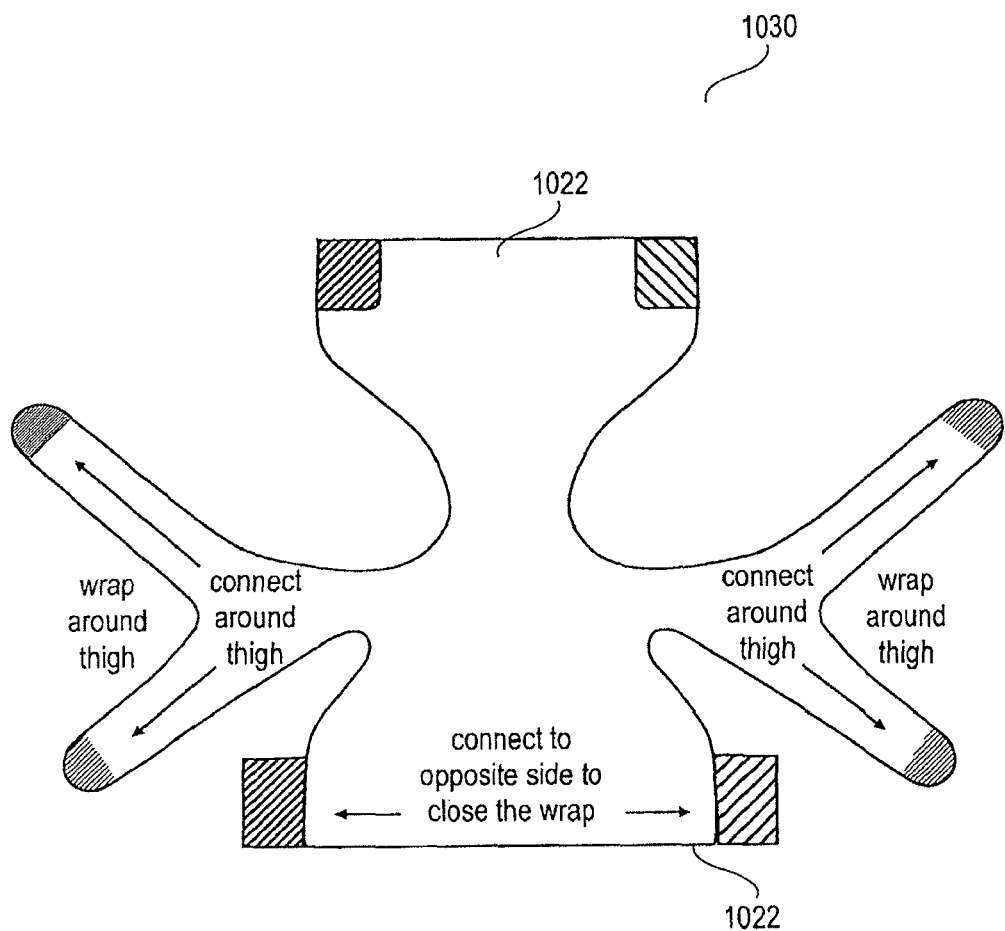

In one embodiment, a folding pattern (e.g., like a diaper) is also a way to anchor a user to the pressure chamber. FIG. 10B and FIG. 10C illustrate embodiments of a folded material sealing mechanism for a differential air pressure system. By making a series of cuts in a body friendly pattern 1020 as illustrated in FIG. 10B or in an alternate body friendly pattern 1030 as illustrated in FIG. 10C, users having a range of body sizes and shapes can seal themselves into a pressurized chamber. The body friendly pattern can be wrapped around the user and secured using any suitable sealing technique or attachment means, e.g. tape, adhesive, clips, Velcro™ type closures, snaps, buttons, or any other suitable attachment means. The top surface 1022 of the body friendly pattern 1020 and 1030, which when wrapped surrounds the user's body at approximately the waist level, attaches to the pressure chamber via a method or structure discussed herein or otherwise known.

Adjustable Height and Support Bars for a Differential Air Pressure System

In a differential air pressure system, it is desirable that the system accommodate as wide a range of users as possible. One of the most challenging aspects to this accommodation is to adjust the height of the opening that surrounds the waist of the individual in an efficient, effective, and user friendly manner while maintaining the structural integrity of the shell under the load resulting from pressurization of the chamber. A chamber that has a fixed height may only be operable over a narrow range of users. If the shell is optimized to reside at the iliac crest of a 6'4" user by example, a 5'0" user will have the opening above the stomach and not be able to use the apparatus effectively.

For a comfortable user experience the height adjustment process should be simple, quick and intuitive to perform and must allow adjustment over a wide range of heights. Further, the mechanism should be easy to operate and require little force to adjust, so it may be operated by elderly or weak individuals.

It is a further benefit if the height adjustment scheme provides for support of the user in the event that there is a depressurization or over pressurization. Having a fabric inflatable with straps anchored to a base or the floor can be an efficient means of maintaining a height of the chamber, but may in some variations provide insufficient safety should the fabric rip or a strap break, or the chamber bag rip and the user fall, for example.

Figure 11:
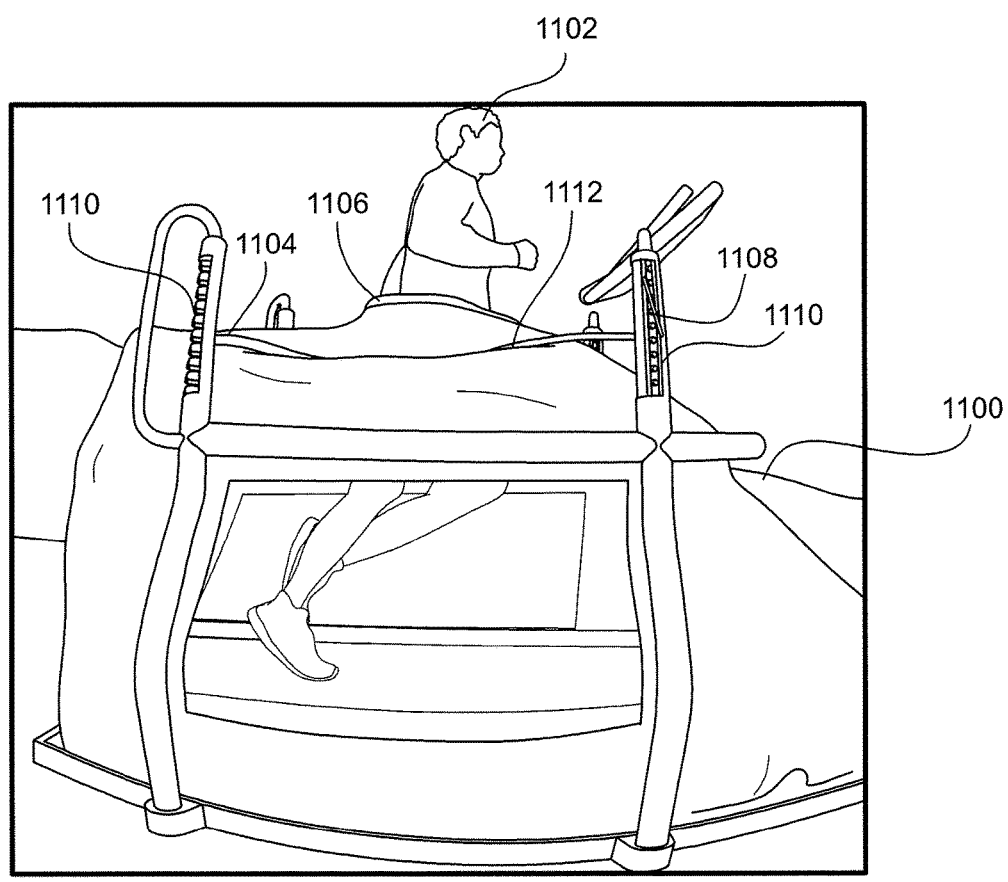
FIG. 11 illustrates one embodiment of a differential air pressure system with provisions for adjusting the height of the chamber opening and for providing safety support for a user.

FIG. 11 illustrates one embodiment of a differential air pressure system 1100, such as those discussed above in connection with FIG. 1 and FIG. 2. In this particular variation, the differential air pressure system 1100 includes a support bar 1104. In one embodiment, the height of opening 1106 may be adjusted and provide user 1102 with support in the event he trips, falls, or in the event that a sudden deflation of system 1100 occurs. In one embodiment, height adjustment and support are accomplished via separate mechanisms. Both aspects, support and height adjustment, are beneficial for a product that is safe, e.g. to prevent falling, and effective for users of a variety of heights.

The support bar 1104 in system 1100 represents one embodiment of a system that incorporates both a support and height adjustment features into a single mechanism or system. However, other embodiments of differential air pressure systems could include only one of these features. In the embodiment illustrated in FIG. 11, for example, a comfortable, safe, highly adjustable, and highly adaptable system is provided.

In some variations, a locking mechanism, such as a locking bar 1108 and height adjustment slots 1110 enable the adjustment of the angle of the support bar 1104, which is important in some circumstances, e.g. when system 1100 is configured to have user 1102 running at an incline. In systems that do not have an adjustable angle in a support bar, when a user runs at a steep incline, the user may collide with the edges of the orifice. A tall person may have the same issue regardless of incline. Thus, the adjustability of support bar's 1104 height and angle, relative to differential air pressure system, increases the range of users who can successfully use the system types and also increases the scope of uses of the system.

In one embodiment, support bar 1104 locks into locking bar 1108 at an angle to which the support bar 1104 has been adjusted. The locking mechanism of locking bar 1108 ensures that if user 1102 were to stumble or fall, the user 1102 would be able to safely support themselves on support bar 1104.

Figure 12:
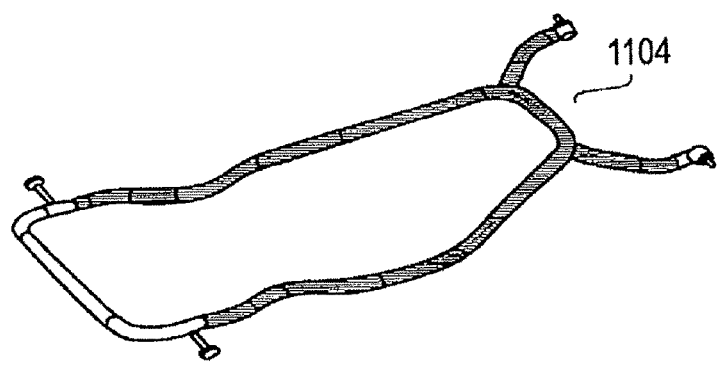
FIG. 12 is a perspective view diagram of one embodiment of a height adjustable support bar of a differential air pressure system.

FIG. 12 provides a perspective view diagram of one embodiment of a height adjustable support bar 1104 of a differential air pressure system, such as bar 1104 of FIG. 11. The height adjustment bar 1104 can be moved around freely by the user, and may be free floating or attached to a framing structure while remaining adjustable. In one embodiment, adjustable support bar 1104 is attached to a differential air pressure system bag through sleeves 1112 of bag 1100 as shown in FIG. 11. The configuration of the bar 1104 in FIG. 11, where the bar 1104 is detached from other structure components in the system 1100, allows for freedom of adjustment of the bar 1104 not only in the vertical position, but also in a tilt orientation.

In some variations, adjustment of the height of support bar 1104 in system 1100 is performed by configuring support bar 1104 at some tilt angle into height adjustment slots 1110. In one embodiment, there are multiple height adjustments slots (e.g. 2, 3, 4, 5, 6, or even more) 1110 constructed of material sufficiently strong so that should user 1102 fall and lean on support bar 1104, height adjustment slots 1110 will not bend or break and can support the full body weight of the user, at least for a short period of time.

Figure 13:
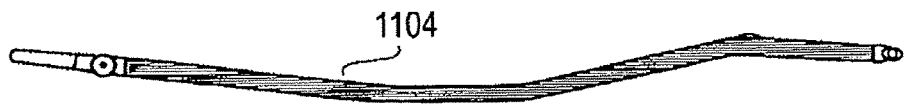
FIG. 13 is a side view diagram of one embodiment of a support bar of a differential air pressure system.

FIG. 13 is a side view diagram of one embodiment of a support bar 1104 of a differential air pressure system. As illustrated in FIG. 13, support bar 1104 is contoured to accommodate user 1102 sprinting, running, jogging, or walking in the differential air pressure system 1100. In one embodiment, the contour of the support bar 1104 is similar to the contour of a saddle. As shown in FIG. 13, support bar 1104 dips low at or near the user's 1102 hips so as to accommodate the user's arm swing, but is raised sufficiently high in the front and rear to accommodate leg kick and high knee action.

Figure 14:
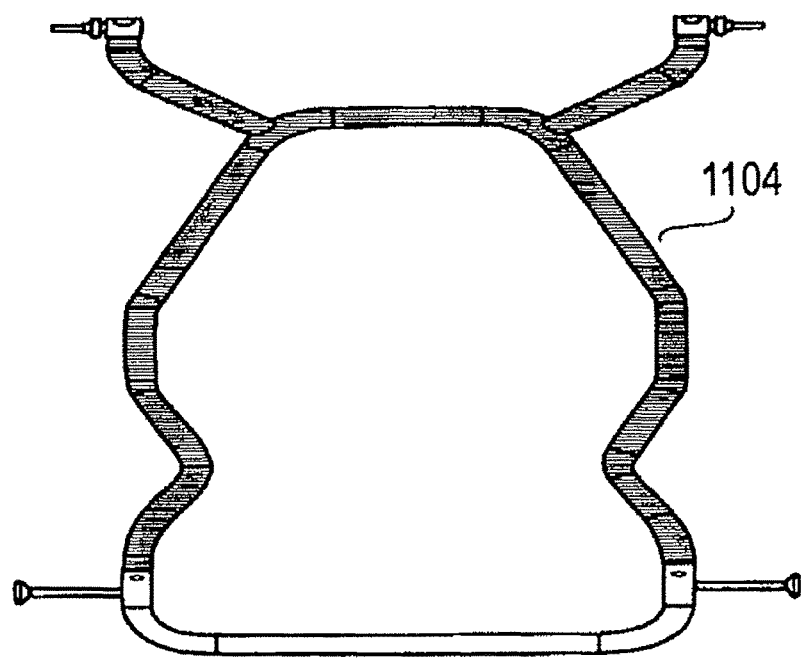
FIG. 14 is a top view diagram of one embodiment of a support bar of a differential air pressure system.

FIG. 14 is a top view diagram of one embodiment of a support bar 1104 of a differential air pressure system. In one embodiment, the perimeter shape of the support bar 1104 controls the perimeter shape of the shell of the differential air pressure system that the user fits into (e.g., a hard or soft shell). In some embodiments, the shape of the support bar 1104 is configured to control that of the shell in addition to any one of the other functions of the support bar as described herein. In an embodiment utilizing a hard shell instead of a soft shell (e.g. a fabric shell), the top portion of the hard shell that is closest to interface to the user may have a similar shape to a saddle for the reasons described above.

In one embodiment, support bar 1104 becomes fixed in place while under use in system 1100. Support bar 1104 is fixed in place via locking bar 1108. In some variations, locking bar 1108 swings down and locks in place once support bar 1104 has been set in a position. In certain variations, an automatic latching mechanism may be utilized. However, as illustrated in FIG. 11, support bar 1104 may be placed into a position on locking bar 1108 such that closing a latching mechanism of the locking bar 1108 secures support bar 1104 in place. In some variations, the support bar 1104 is latched to a front portion of a frame of the differential air pressure device 1100. The latch however still may be configured to allow the support bar 1104 to rotate about an axis even while latched.

Figure 15A:
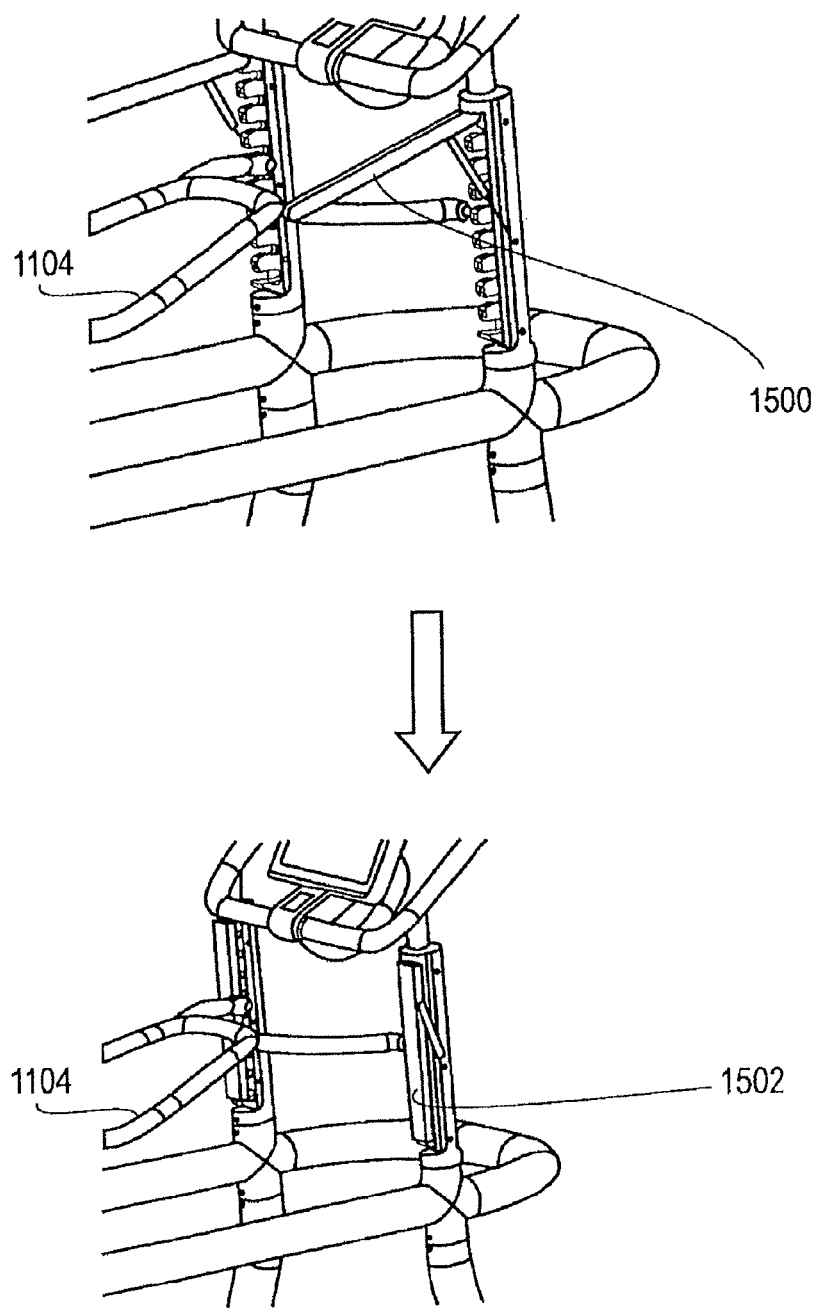
FIG. 15A is a diagram of one embodiment of a latching mechanism to secure support bar to a differential air pressure system.

FIG. 15A is a diagram of a variation of a latching mechanism to secure a support bar 1104 in a differential air pressure system 1100. As indicated by the arrow in FIG. 15A, the latching mechanism may be transitioned from an open position 1500 to a closed position 1502 to secure support bar 1104 in place in a differential air pressure system 1100.

Figure 15B:
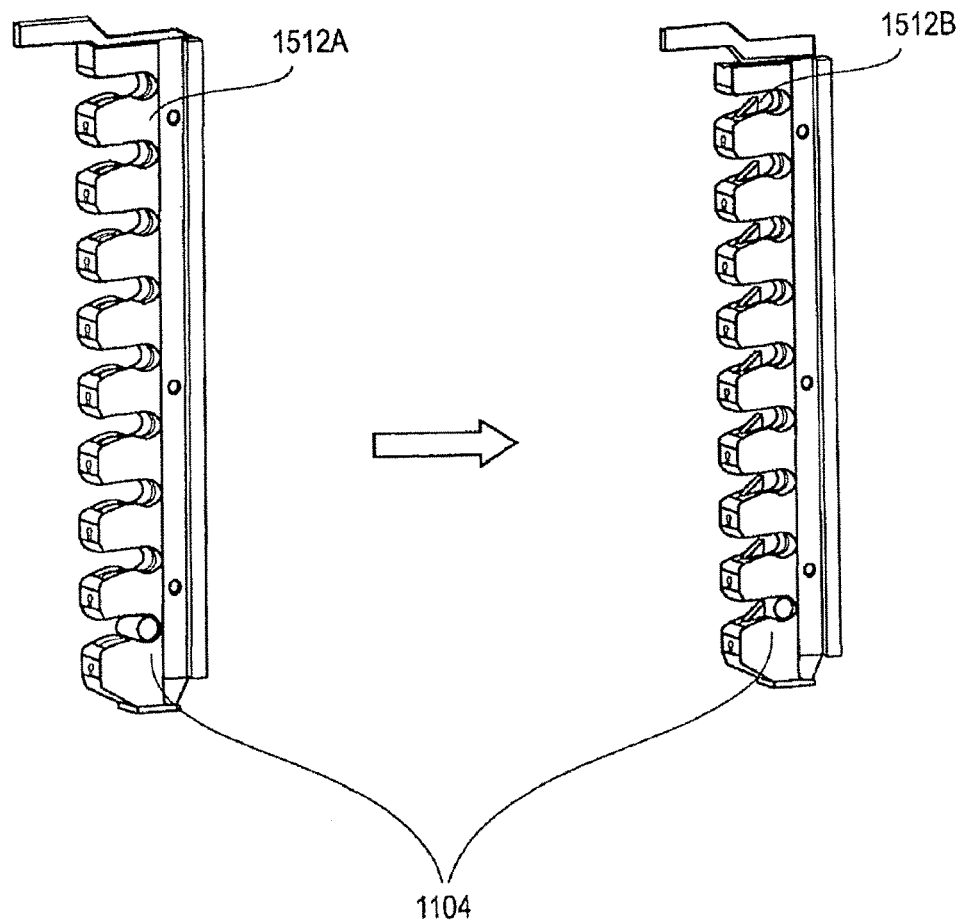
FIG. 15B is a diagram of another embodiment of a latching mechanism to secure support bar to a differential air pressure system.

FIG. 15B is a diagram of another variation of a latching mechanism to secure a support bar 1104 in a differential air pressure system 1100. In the variation illustrated in FIG. 15B, the latching mechanism includes one or more loaded cams 1512A, e.g. an array of loaded cams 1512A, with each loaded cam corresponding to a selectable position for support bar 1104. As illustrated, the bar 1104 is locked into position when spring loaded cams are in position 1512B.

Figure 16:
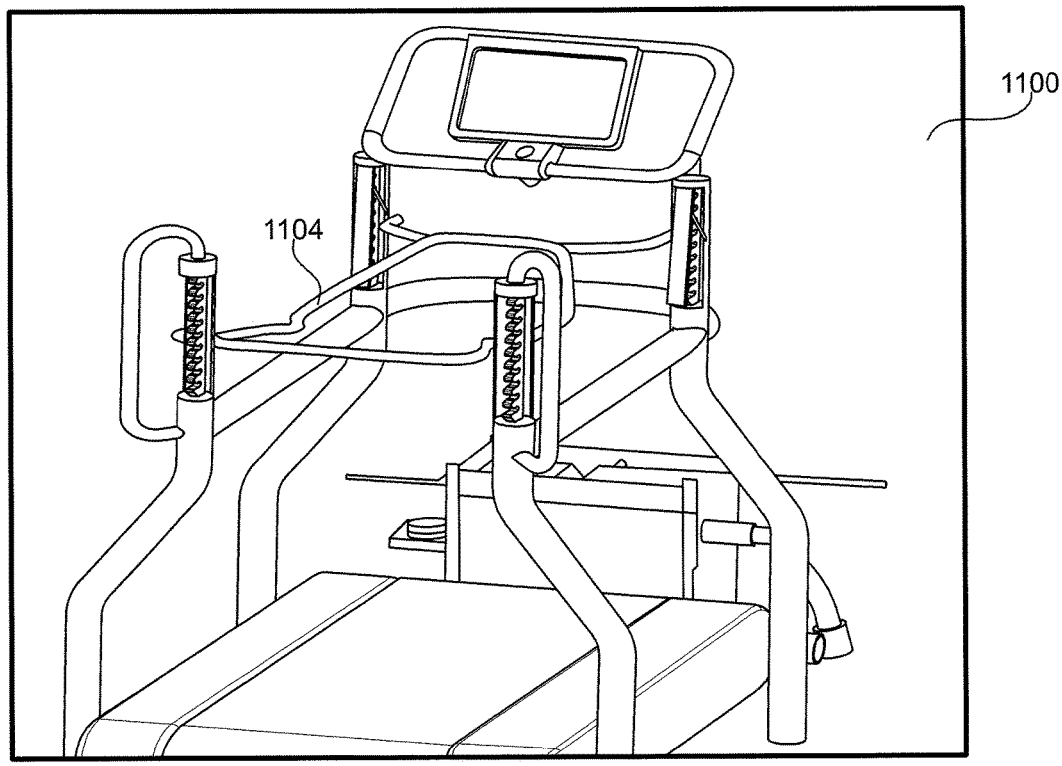
FIG. 16 is a perspective view diagram of an example of a support bar coupled to a differential air pressure system.

FIG. 16 is a perspective view diagram of a support bar 1104 coupled to a differential air pressure system 1100.

Figure 17:
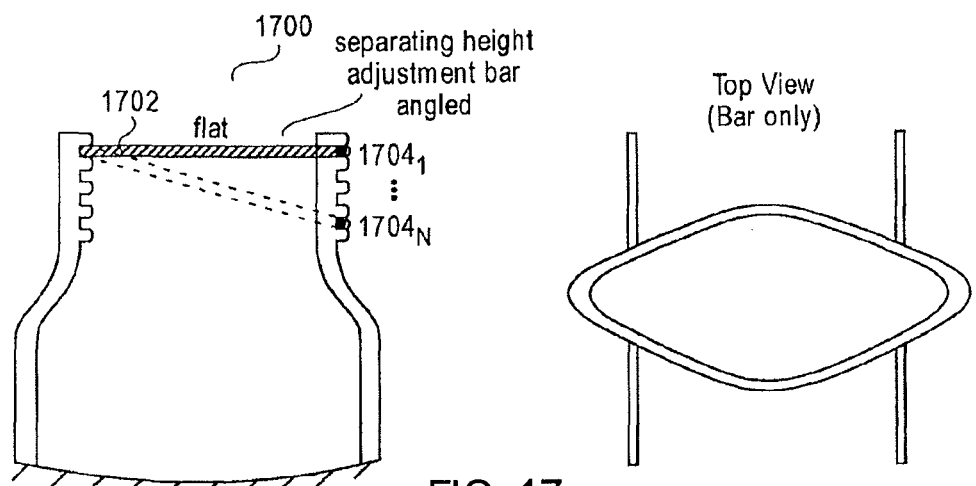
FIG. 17 illustrates one embodiment of a height adjustable structure for a differential air pressure system.

Another example of a height adjustable structure 1700 for a differential air pressure system is illustrated in FIG. 17. There, the structure 1700 comprises a series of horizontal slots 1704$_{1 \ldots N}$ in the front and in the rear of the system. As illustrated, a support bar 1702 extends between the horizontal slots in the front and rear of the system. In one embodiment, the support bar 1702 is affixed to the shell (e.g. a fabric shell) just below the opening in the shell, thus lifting the shell opening to an appropriate height that the user selects. This adjustment scheme allows the user to easily and conveniently attach himself to the shell (e.g. fabric shell) for pressurization. The bar 1702 allows for varying angles, should the user want to exercise at inclines or declines in the apparatus. The bar may be locked into place in the horizontal slots, or alternatively the slots may be formed such that the bar is locked into place under pressure and loose otherwise.

Figure 18A:
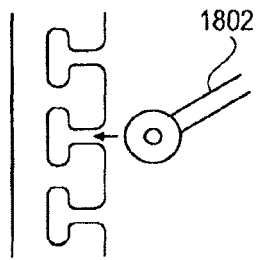
FIGS. 18A-18D illustrate additional embodiments for locking mechanisms for a height adjustment structure in a differential air pressure system.
Figure 18B:
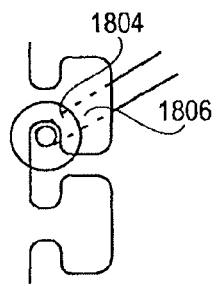
Figure 18C:
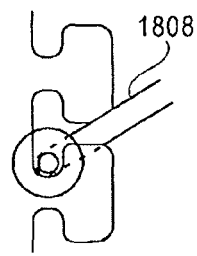
Figure 18D:
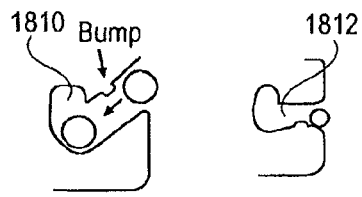

In some variations, the bar may be inserted into a slot and pushed to the rear of the slot, as illustrated in FIG. 18A. As the pressure inflates, the bar 1802 is lifted into a notch or groove 1804 with a portion 1806 to hook the bar and prevent the bar from moving under for/aft loading, as illustrated in FIG. 18B. Upon a reduction of pressure in the chamber the bar may fall back down 1808 and be pulled out by the user, as illustrated in FIG. 18C. Such notch designs as illustrated in FIGS. 18A-18C may be advantageous by requiring few user actions while maintaining a safe lock during use. Alternate variations of slot designs, such as 1810 and 1812, are shown in FIG. 18D. An additional function of a notch design as illustrated in FIGS. 18A-18D may be that the bar 1802 is capable of at least temporarily supporting the user in the event of an unexpected or sudden depressurization or in the event the user trips or falls. This safety feature may be important for frail users such as elderly patients or users with neuromuscular disorders. As there is a vertical load on the bar, the bar is forced into place and a horizontal force will not be able to dislodge the bar. The number of slots and distance between height adjustment slots as illustrated in FIGS. 17 and 18 can determine the range of height adjustability and the range of users that the system can accommodate. In certain variations, the height adjustment slots may be marked in some fashion. Such markings may include inscribing the a user height to a horizontal slot position, or simply a numbering scheme 1, 2, 3, etc. to indicate an arbitrary setting instead of an absolute height value, such as 5'0, 5'4", 5'6", etc.

In some variations, the height adjustment slots may include a bump, protrusion, or other mechanical barrier, e.g. as illustrated in FIG. 18D, such that the bar must be pushed past that protrusion or barrier to lock the bar into place, and/or there may be a second locking rod or bar that is put in place after insertion of the height adjustment bar into the slots. In one example, the bar is wedged past the bump or barrier using the elastic properties of a latch to spring open and lock the bar into place in a groove, e.g. similar to a gate locking mechanism.

In the systems described herein, the support bar and their support mechanisms and locking mechanisms are capable of withstanding high vertical force to support both the large force due to pressure and a dynamic load should the user fall on the height adjustment bar and use it for support. For reference, the vertical load may be approximated by the surface area of the bag on the bar multiplied by the pressure in the chamber. An estimate is 24".times.36".times.2 lb/sqin=.about.1700 lbs of vertical load due to pressure.

Figure 19A:
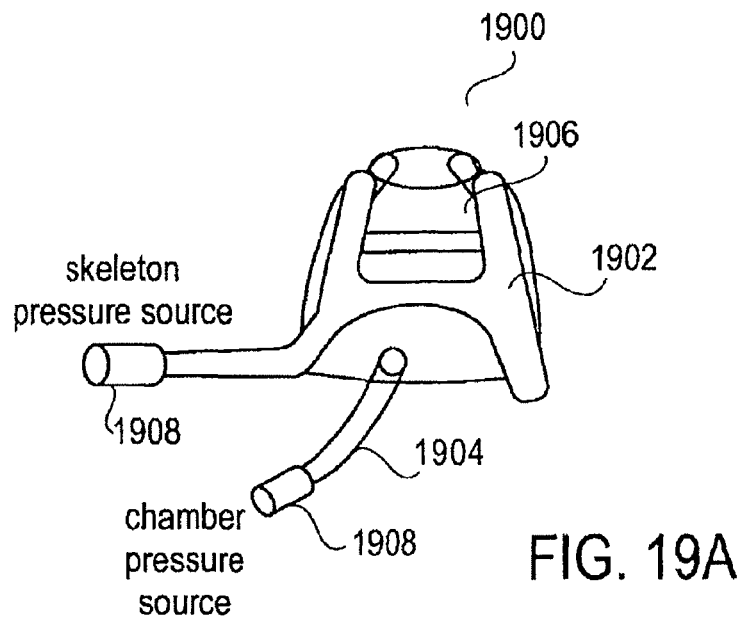
FIGS. 19A-19B illustrate additional embodiments for skeleton enforced shells to perform height adjustment in a differential air pressure system.
Figure 19B:
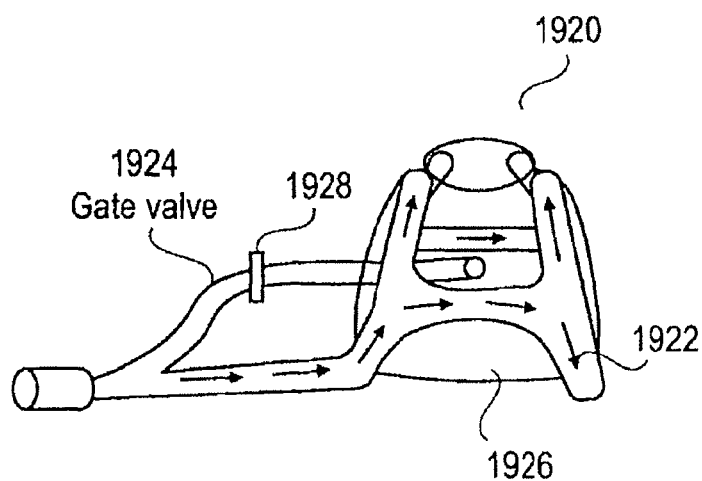

Additional embodiments of a height adjustment in a differential air pressure system are illustrated in FIGS. 19A and 19B. There, a differential air pressure system 1900 includes an inflatable skeleton 1902 for a fabric shell. This skeleton 1902 can comprise a plurality of connected inflatable tubes sewn or otherwise attached on the inside or the outside of the chamber 1906. The chamber 1906, when inflated, forms a semi stiff structure that pulls the enclosure fabric to a shape close to what it will adopt when under pressure. When the skeleton 1902 is inflated, the opening for the user will be at a vertical height at which a user can attach the user seal, as discussed herein, to the chamber and prepare for pressurization of the entire chamber in addition to the skeleton. The inflated skeleton shape may also provide some additional supporting force should the main fabric shell rip or tear and depressurize. The vertical height limit of the enclosure may be adjusted either with a rigid bar that fixes to an external frame, which would provide a supporting structure, or it may be limited by adjustably strapping the top of the enclosure and skeleton to the base of the apparatus or some other location on or outside the chamber that will put the strap in tension. In one embodiment, the pressure in the skeleton 1902 and the pressure for the main enclosure 1904 are provided with two separate pressure sources 1908.

In another embodiment, illustrated in FIG. 19B, a single pressure source 1924 may be used to inflate both the skeleton 1922 and the chamber 1926 by having a valve 1928 (e.g. a gate valve) that is configured to route air to the skeleton 1922 prior to routing air to the main chamber 1926. In some variations, once a desired pressure is reached in the skeleton 1922, the valve 1928 can allow for airflow into the chamber 1926. In one embodiment, the switch in routing air pressure may be controlled by a sensor (not shown) that sends a signal to a controller when the pressure in the skeleton is sufficient. In another embodiment, the switching of the air pressure supply from the skeleton 1922 to the chamber 1926 may be accomplished by waiting a minimum time for inflation of the skeleton before diverting air into the chamber. In any variation, the switch to divert flow from the skeleton to the main chamber may be activated automatically (e.g. after the desired pressure in the skeleton has been reached or after a minimum wait time has passed), or manually by a user-activated switch, or by any suitable switching scheme.

FIG. 20A illustrates an embodiment of an inflatable skeleton supported fabric shell for a differential air pressure system. In this particular variation, the inflatable skeleton 2002 may be sewn on the inside of the fabric shell 2004 and may be constructed of a slightly porous material that bleeds air into the interior of the chamber once a certain pressure has built up inside the fabric skeleton.

In different embodiments, illustrated in FIGS. 20B and 20C, the inflatable skeleton may be sewn out of air tight material and disposed either on the inside of the chamber, as illustrated in FIG. 20B, or the outside of the chamber, as illustrated in FIG. 20C, of the fabric enclosures 2020 and 2030, respectively. In some variations, one or more holes are made to connect an air circuit from the skeleton to the interior of the chamber so that once pressure is built up to a desired level in the inflatable skeleton, the air passes to the interior of the chamber during user operation. This method does not require a valve (e.g. a gate valve) to route air from the skeleton to the chamber.

Figure 21:
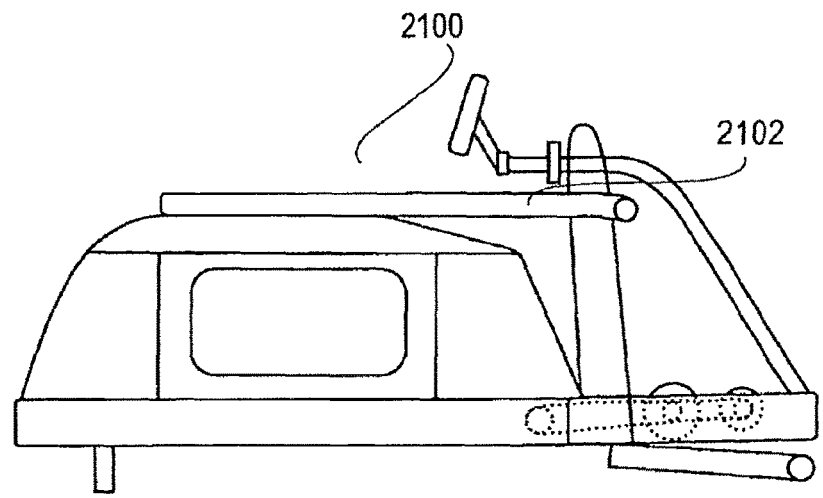
FIG. 21 illustrates one embodiment of a height adjustable opening in a differential air pressure system shell.
Figure 24A:
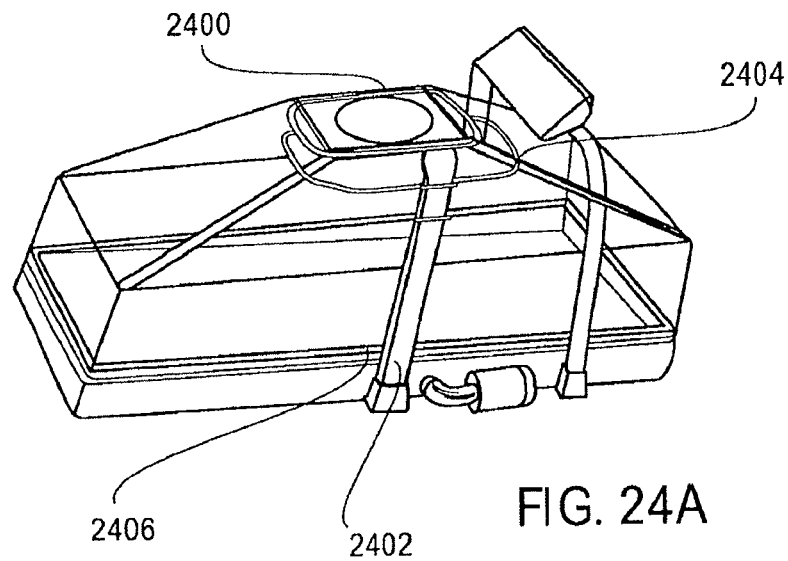
FIGS. 24A-24D illustrate various embodiments of height adjustment mechanisms for a differential air pressure system.

FIG. 21 illustrates an embodiment of a height adjustable opening in a differential air pressure system shell. There, for the system variation 2100, height of the opening for the user is adjusted via a rigid height adjustment structure 2102 that translates up and down on one or more guide posts similar to traditional weight lifting equipment. For example, the structure could slide, roll, move on a rack and pinion gear, or translate by other methods described herein, or otherwise known. In certain instances, the height adjustment structure may be cantilevered off a single guide post that is placed in proximity to the chamber, or may ride up and down several guide posts. In some variations, the height adjustment structure 2102 may be locked into position once the desired position is reached. Such locking may be accomplished by a pin, magnet, clamp, or other locking mechanism described herein or otherwise known. One example of a single cantilevered structure is shown in FIG. 24D and one example of a multiple guide post system is shown in FIG. 24C.

Figure 22:
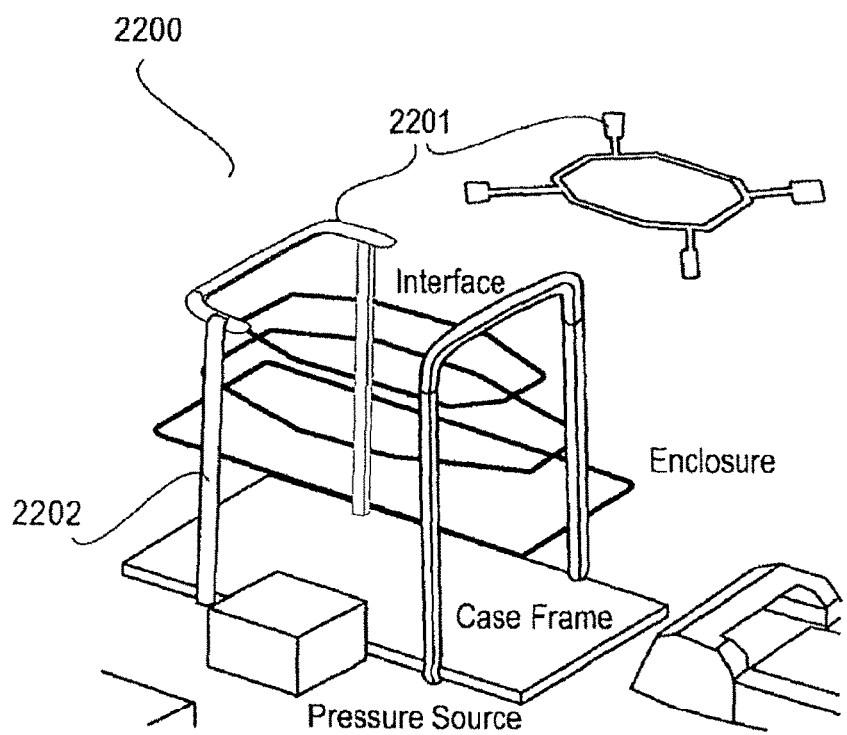
FIG. 22 illustrates another embodiment of a height adjustable opening in a differential air pressure system shell.

An example of a height adjustment bar which translates up and down multiple guide posts is shown in FIG. 22. There, system 2200 includes a height adjustment bar 2201 that is configured to translate up and down guide posts 2202. Once desired height is achieved, height adjustment bar 2201 is locked and coupled to guide posts 2202. Optionally, height adjustment bar 2201 may be counterbalanced so the lifting force is minimized for users that may be frail or weak and unable to lift a heavy object. Optionally, height adjustment bar 2201 may be motorized to move up and down guideposts 2202. In certain variations, any suitable locking mechanism such as pins, pinion gears that engage racks, etc. may be used to maintain a desired height adjusted position.

Figure 23A:
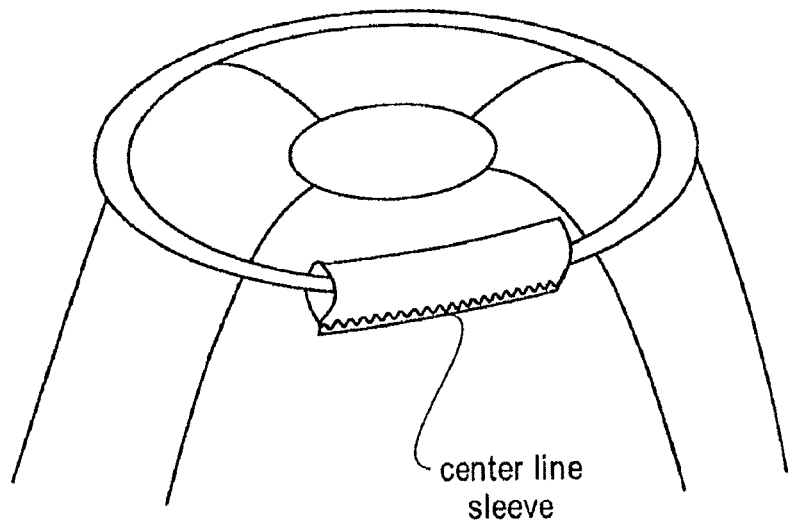
FIGS. 23A-23B illustrate various embodiments of a shaping structure coupled to a height adjustable structure for a differential air pressure system.

In some variations of differential air pressure systems, the enclosure may be coupled to a height adjustment structure so that adjustment of the height adjustment structure simultaneously adjusts the height of the enclosure or vice versa. The height of the height adjustment structure may be adjustable by any of the methods described herein or otherwise known. FIG. 23A illustrates one embodiment of a system in which the enclosure is coupled to the height adjustment structure, e.g. where the height adjustment structure is sewn into sleeves of the enclosure. In other variations, the enclosure may be coupled to the height adjustment structure using another suitable technique, e.g. adhesive, clamps, fasteners, and the like.

Figure 23B:
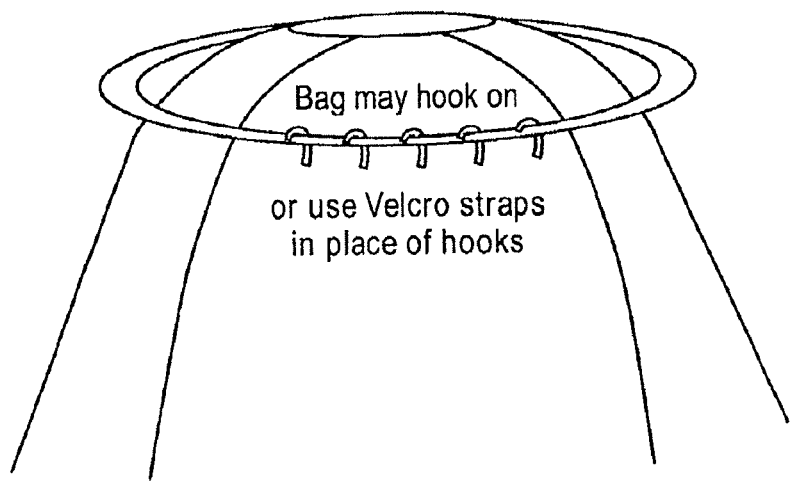

In another embodiment, the height adjustment structure may be separable from the enclosure so that the user may adjust the height of the height adjustment structure first and then attach the enclosure to the structure. FIG. 23B illustrates one embodiment in which a height adjustment structure is coupled to an enclosure via one or more reversible attachments, e.g. hooks, snaps, Velcro™ type closure straps, clamps, and the like, after the user has adjusted the height.

In one embodiment, to reduce the lifting force required to raise the height adjustment structure, and possibly the fabric enclosure as well if the enclosure is coupled to the height adjustment structure, the height adjustment structure may be counter balanced with weights or electro-mechanically lifted, for example by a motor, motor and belt system, etc. Other lifting systems may include lead screws, hoists, winches, hand cranks, scissor lift (manual or automated), hydraulics, or other means of mechanical or electromechanical advantage to reduce or eliminate the force required to lift the structure by the user. FIG. 24A illustrates one embodiment of a motorized height adjustment structure 2400, which includes a belt driven by a motor 2402, where the belt drives a height adjustment bar 2404 up and down a guide post 2406.

Figure 24B:
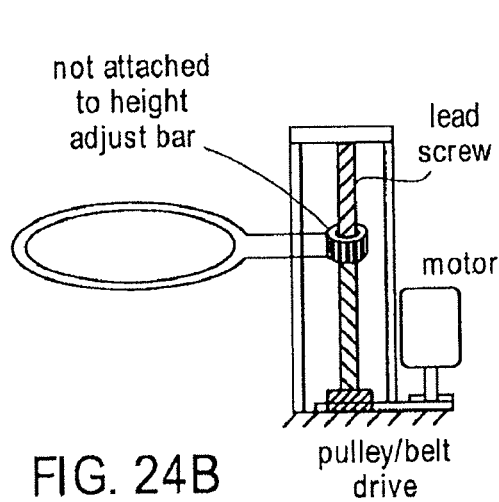
Figure 24C:
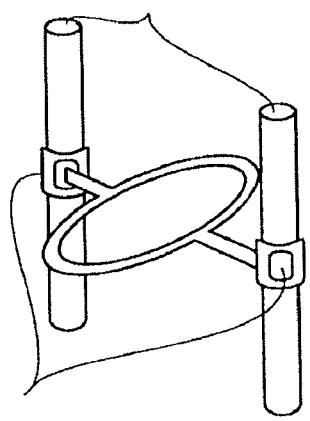
Figure 24D:
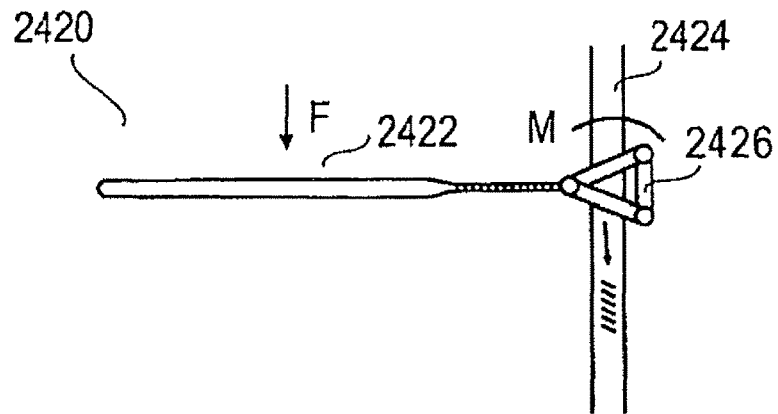

FIG. 24B illustrates one embodiment of a height adjustment mechanism, for use with a differential air pressure system, that utilizes a lead screw system.

FIG. 24C illustrates one embodiment of a height adjustment mechanism, for use with a differential air pressure system, that utilizes a counter balanced two guide post system.

Any of the height adjustment systems and lifting systems as described herein may further include a locking mechanism to secure the position of the height adjustment structure once the desired height is set. Such locking may be done with pins or other mechanical interference, worm gears or lead screws or other non-back-drivable gearing, strong electro magnets, straps to a portion of the main system structure, or use of friction as in a cantilevered system. Other means of mechanical locking are considered within the scope of this invention.

FIG. 24D illustrates an embodiment of a height adjustment mechanism, for use with a differential air pressure system that utilizes a cantilevered lifting system which uses friction to lock a height. In the illustrated embodiment, the center of mass 2422 of the height adjustment structure 2400 is to the left of the guide post 2424. The force of gravity exerts a downward force at the center of mass 2422 of the height adjustment structure 2420. This downward force creates a moment about the guide post 2424 which tries to rotate the structure counterclockwise. This moment produces normal forces between the points of contact of the structure with the guide post and the surface of the guide post. These normal forces produce a frictional force between the surface of the guide post 2424 and the contacting member 2426. The higher the moment, the higher the normal force, and the larger the resistance the structure has to overcome to translate vertically along the guide post. As long as the frictional force between the guide post and the contacting member is greater than other net external forces, such as the force due to gravity on the height adjustment structure, the height adjustment structure will not undergo displacement along the guide post.

Figure 25A:
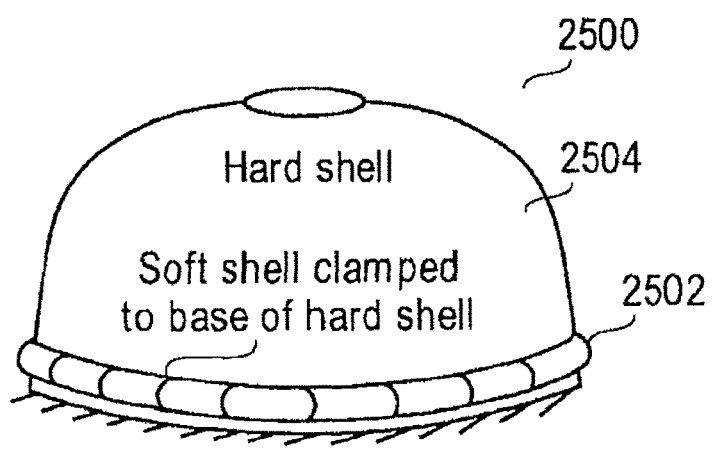
FIGS. 25A-25D illustrate various embodiments of height adjustment structures for a differential air pressure system.

Another system and related method for adjusting the height of an opening in a chamber for receiving the body of a user may include the use of a combination of one or more hard portions of a shell and one or more soft or flexible portions of the shell. In such system variations, the soft portion of the shell may expand or be compressed to allow for the vertical adjustment. The soft portion of the enclosure may reside at any point along the vertical direction of the hard shell, and may even divide the hard shell into two or more portions. FIG. 25A illustrates one embodiment of a height adjustable structure 2500 that includes a soft shell portion 2502 located below a hard shell portion 2504. Soft shell portion 2502 may be collapsed or expanded to give height adjustment to the upper hard shell portion 2504. Such a method may be used in conjunction with a locking mechanism such as a pin joint, clamp, or straps, or other locking device or method described herein or otherwise known.

Figure 25B:
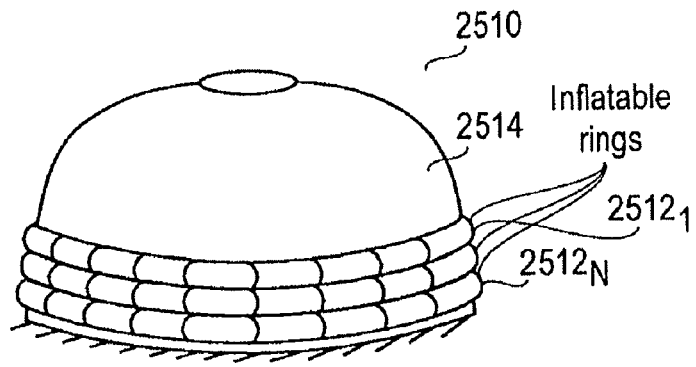

FIG. 25B illustrates one embodiment of a height adjustable structure 2510 that includes a plurality of soft shells portions, such as soft shell portions 2512$_1$ to 2512$_N$, located in vertical arrangement below a hard shell portion 2514. In one embodiment, soft shells portions 2512$_1$ to 2512$_N$ may be selectively inflated, or inflated at varying pressures, to lift the hard shell to different heights.

If a differential air pressure system comprises a hybrid shell comprising one or more soft portions and one or more hard or rigid portions, the hard shell portion may be movable by automation or by the user lifting the shell. In one embodiment, the hard shell portion may be counter balanced to allow for easier lifting by the user. The position of the hard shell portion may further be lockable in place once the proper height is achieved. Any means of lifting or locking as described herein or otherwise known may be implemented with a hard shell portion as well. The height of the hard shell portion may remain locked during use such that as pressure varies the shell remains fixed vertically.

Figure 25C:
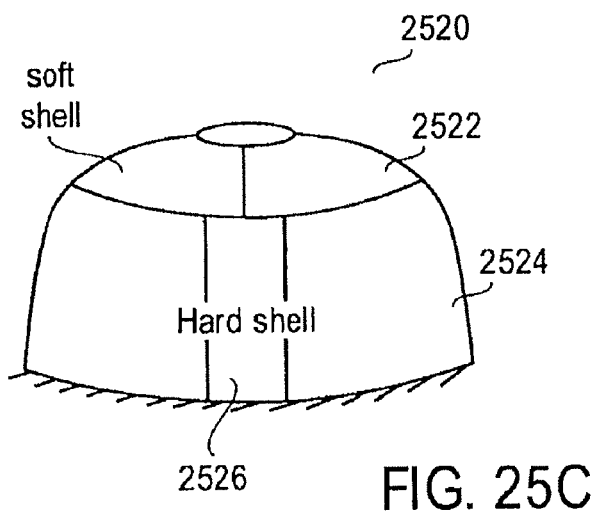

FIG. 25C illustrates another embodiment of a soft shell portion on top of a hard shell portion in a differential air pressure system. An upper soft shell portion 2522 may be considered advantageous in situations where a greater contouring ability about the user is desired. The soft shell portion 2522 may be either separable or split in one or more sections, for example, with a zipper, to allow the user simple access through the opening. Should the soft shell portion 2522 be separable from the chamber 2524, the soft shell portion 2522 may be coupled to the user, such as through a user seal, thereby essentially becoming an extension of the user seal outside the chamber, and then sealed to the chamber once the user is in position via a method described herein or otherwise known. Such a separable soft shell portion may for example be a kayak-style cinch to a lip on the chamber, a clamping bar secured to the enclosure around the perimeter of the upper soft shell top, or other means of clamping the soft shell to the chamber described herein or otherwise known. Further height adjustment or soft shell contouring, as discussed below, may then be performed, for example, using one or more straps that secure the softer upper shell portion to the lower hard shell portion and may be adjustable. Additional configurations and variations of shells including one or more hard shell portions and one or more soft shell portions are discussed in greater detail below.

Figure 25D:
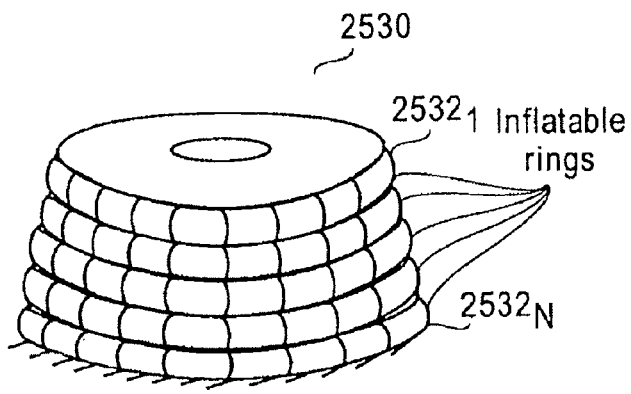

FIG. 25D illustrates one embodiment of a height adjustable structure 2530 that includes a plurality of inflatable rings stacked on top of one another. In one embodiment, to adjust the height of the structure 2530, one or more of the rings $2532_1$ to $2532_N$ are filled with a substance (such as air, other gas, or liquid) and others of the rings $2532_1$ to $2532_N$ are left empty, so that as rings are inflated the height of the chamber is incrementally increased. In some variations, the user may control which rings are inflated by either selecting an initial height and a controller (not shown) controls one or more valves to inflate the appropriate ring or rings. In another embodiment, the user may have the ability to choose one or more rings to inflate. Other methods for inflating rings may be used, e.g. by specifying a sequence with which to inflate rings, by specifying pressures to which certain rings are inflated, and the like.

Figure 26A:
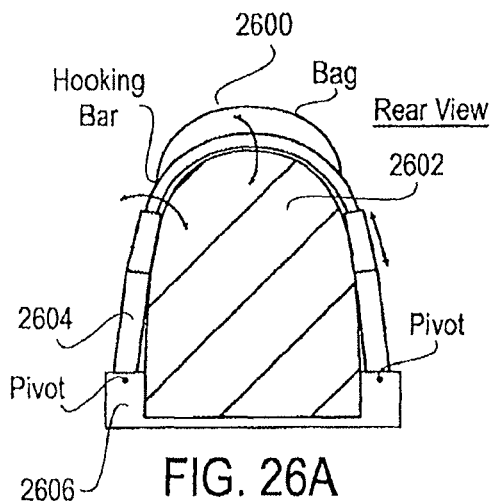
FIGS. 26A-26B illustrate various embodiments of an adjustable height differential air pressure system chamber.

FIG. 26A illustrates one embodiment of an adjustable height chamber 2602 in a differential air pressure system 2600. In this particular embodiment, the height of the chamber 2602 is adjustable via adjustable bars 2604 that can translate up and down relative to a user. In one embodiment, the bars 2604 may be locked at various points in the vertical direction. The bars 2604 may be attached to a soft shell enclosure, or the enclosure may be attached to the bars 2604 after the heights of the bars are adjusted. The adjustable bars 2604 may be connected into a ring or other geometry that creates a loop, e.g., parallel to the floor, and around the user's body, so that the adjustable bars are lockable and fixed in a looped configuration under pressure, as it is not a requirement that the adjustable bars 2604 be oriented in a vertical geometry. In one embodiment, the adjustable bars may be hinged or pivoted at point 2606 near the base of system 2600 so that the adjustable bars 2604 may be angled inward in addition to translating along an axis, to provide an additional important degree of freedom for chamber width adjustment and shell contour. The combination of angle adjustment or vertical adjustment allows for a wide range of positions for height and width of the bar.

Figure 26B:
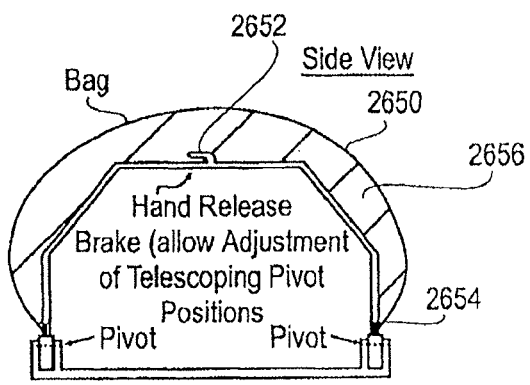

FIG. 26B illustrates an embodiment of a differential air pressure system that includes a locking mechanism. In this particular embodiment, the differential air pressure system structure 2650 may be locked in place once a desired geometry has been achieved (e.g., a specific height has been reached by adjustable vertical bars 2654). The locking mechanism may include one or more clamps, pins, magnets, or other means of locking described herein or otherwise known. For convenience, the locking mechanism may include a simple handbrake style adjustment 2652 where the user depresses a button or squeezes a lever to releases all pins or other locking mechanisms, and when the user releases the button or lever, the locking mechanisms are re-engaged and the structure holds it shape. In other variations, other locking mechanism may be utilized to secure a position of the differential air pressure system structure, and the illustrated handbrake does not limit the types of locking means. A locking mechanism makes it convenient for a user to operate a lever located on the rail or rails 2656 of the structure 2650, pull the rails to a convenient position, and release the lever. This type of height adjustment may allow for off-center structure positions to be obtained, which may potentially assist some users to combat abnormal gait mechanics in some configurations. Optionally, a locking or joining bar may be provided to transversely join two opposing sides of the structure (e.g. if such transverse bars are not already in place and connected as described herein). The incorporation of a transverse locking bar could serve as a gate mechanism that the user would swing shut and secure after entering and adjusting the side bars.

Figure 27:
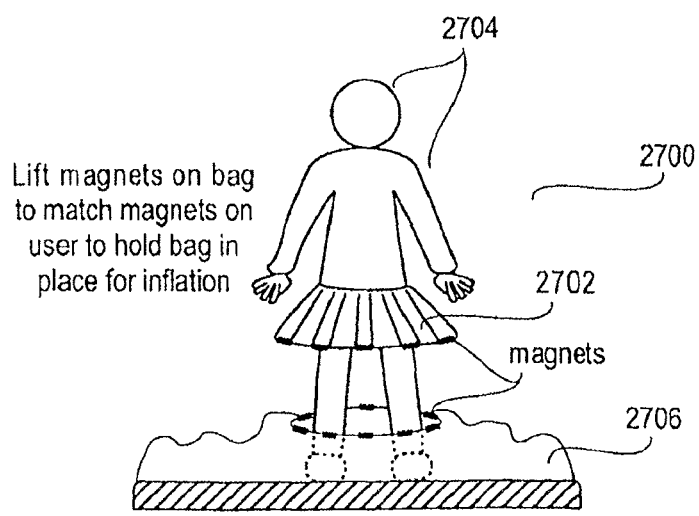
FIG. 27 illustrates one embodiment of a user seal attachment for a differential air pressure system enclosure.

FIG. 27 illustrates one embodiment of a user seal attachment 2702 for a differential air pressure system enclosure 2706. A difficulty in attaching a user to an enclosure is that the weight of an enclosure may make it difficult to simultaneously hold the enclosure near a user's body and attach the user to the enclosure. Thus, it may be useful to have one hands-free joining mechanism for connecting user 2704 to the chamber 2706 and creating an airtight seal until the air pressure within the chamber can support the weight of the enclosure. In one embodiment, raising the opening of the enclosure up to user level and maintaining enclosure height during inflation may be accomplished by providing magnets with which to attach the user seal to the enclosure. The user may wear a magnetic belt (not shown), or wear a special pair of flanged shorts comprising magnets 2702. In addition, magnets may be provided on the enclosure (e.g. fabric enclosure) so that a seal is created by magnetic attraction so that inflation of the chamber can support the enclosure. Height may be restricted with a system of straps anchored to the base or other structure as one example.

In another embodiment, a snapping mechanism worn by the user may be activated when a portion of the user seal is mated with a matching portion of the enclosure. An example of this concept is a ring around the user that fits in a concentric manner with a ring on the enclosure, and a latch (e.g. a rotating latch) positioned on either the user seal or the enclosure piece, such that the user may pick up the enclosure and fit the portion of the user seal inside the portion on the enclosure and activate the latch with their hand to secure the two pieces together. Other locking mechanisms may also be utilized in a differential air pressure system.

Figure 28:
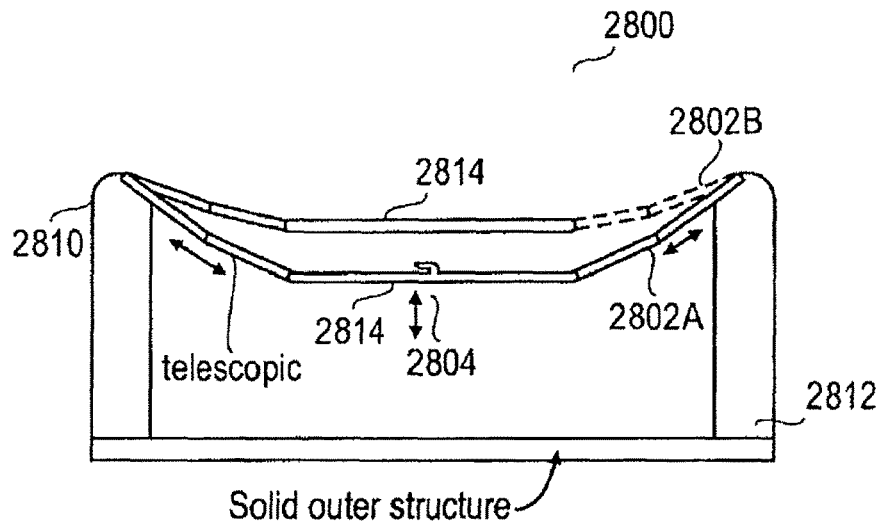
FIG. 28 illustrates one embodiment of a differential air pressure system height adjustment.

Another method of adjusting the height may be a linkage system comprising one or more translating or rotating members that may be locked to form the upper surface of the height adjustment structure and maintain shape under pressure. FIG. 28 illustrates one embodiment of a linkage system and related method for height adjustment via two vertical members. There, a linkage system for height adjustment 2800 comprises two vertical supports 2810 and 2812, one positioned in the front of the apparatus and one positioned in the rear of the apparatus. The linkage system 2800 may comprise a pair of central bars 2814 positioned along the user's sides, with two connecting bars 2802A connecting each central bar 2814 to the front vertical support 2810 and the back vertical support 2812. In one embodiment, these connecting bars 2802A may be telescoping. As the connecting bars 2802A are telescoped so as to be lengthened or shortened (for example to position 2802B indicated by a dashed line), the central bars 2814 may move up and down, and even forward and backward in some instances. The linkage system 2800 may be lockable and have a button or lever mechanism 2804 which allows for free movement of the apparatus, and when released locks the linkage in place. In one embodiment, the geometry of the structure, and more specifically the central bar 2814, may be configured such that the shape of the linkage system 2800 promotes freedom of arm movement or minimal impact with the user's body.

Figure 29:
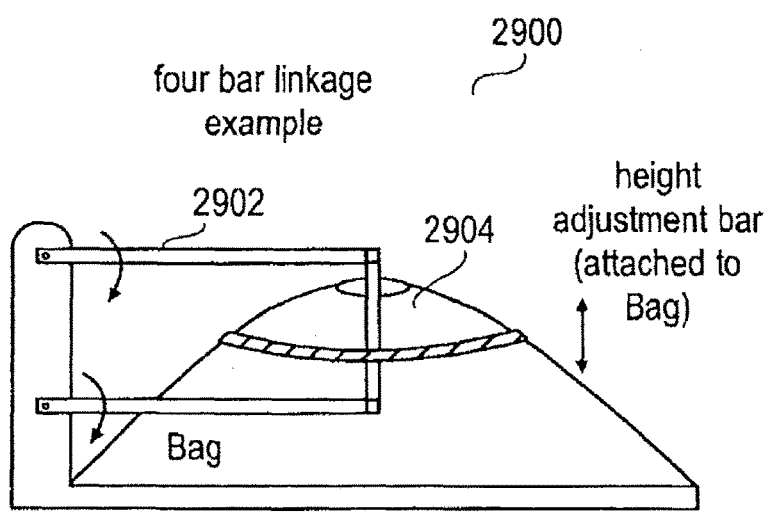
FIG. 29 illustrates another embodiment of a differential air pressure system height adjustment.

Another embodiment of a linkage system is shown in FIG. 29. The system shows a linkage system 2900 comprising four bars 2902 that create a central portion 2904 into which the user fits. The linkage system 2900 is configured to move up and down vertically while maintaining an orientation that is generally parallel to the ground. Such a system may be advantageous in some cases because it does not require telescoping bars or joints.

As has been discussed herein, straps can be used to adjust the vertical position of the chamber opening that attaches to the user. Ropes or cables may also be used to restrict the vertical position of the opening. Such a system with ropes or straps may be individually adjustable or may be connected via pulleys and routing so that a single cable, strap, or rope may be pulled to evenly adjust all cables or straps simultaneously to maintain a level top surface. The position of this adjustment may be locking with a knot, cable grip, cam lock, or the like. Many such locking mechanisms are seen in yachting or boating. If a vertical height adjustment system for a chamber does not itself provide a user support in the event of a tear in the enclosure or pressure failure, in some variations, a secondary vertical support system, e.g. similar to a harness, may be provided for the user.

It may be advantageous in some situations to have a hard shell to promote ease of access, for example by not having to step over fabric folds or the like. Hard shell differential air pressure system also can allow for height adjustment to accommodate users of varying statures. Furthermore, it may be advantageous to maintain the structural integrity of the hard shell, and instead to raise the height of the floor, exercise platform treadmill, or other exercise apparatus instead of changing the height of the opening on the shell itself. In those variations, the shell could be built to the largest desired size and smaller users would be raised up to meet the upper surface of the shell.

Figure 30A:
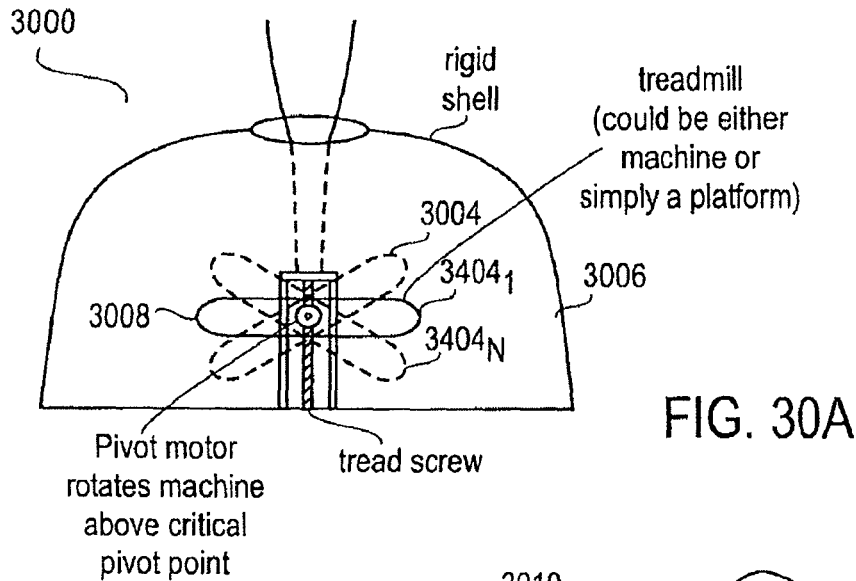
FIGS. 30A-30C illustrate various embodiments of lift mechanisms for a floor or exercise apparatus positioned at least partially inside a differential air pressure system.
Figure 30B:
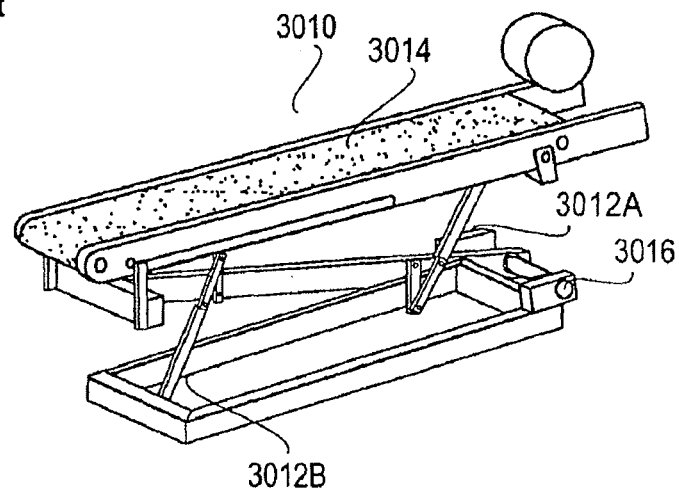
Figure 30C:
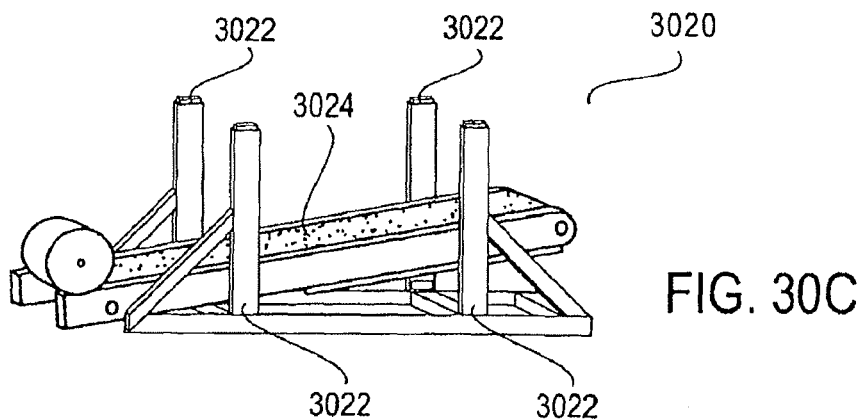

FIGS. 30A-30C illustrate a height adjustable treadmill in a hard shell differential air pressure system, however, any exercise device (e.g., a stepper, elliptical, bicycle, rowing device, etc.), may be utilized. Furthermore, even height adjustable simple platforms, balance platforms or small stepper machines may be used in a hard shell system. FIG. 30A illustrates one embodiment of a lift mechanism 3000 that comprises a lift and pivot mechanism. In this particular embodiment, the lifting operation is performed in the center of the treadmill with, for example two lead screws or linear actuators, which adjust the vertical height. Incline (i.e., adjustment between orientations $3004_1$ to $3004_N$ of treadmill 3008) may be performed by a pivot motor which rotates the treadmill to incline or decline and has a brake, either mechanical or electromechanical.

FIG. 30B illustrates another embodiment of a lift mechanism 3010 for a differential air pressure system. There, lift mechanism 3010 comprises two linear actuators, 3012A and 3012B. The treadmill 3014 (or other exercise machine or platform) is connected to a scissor lift style mechanism 3016. Controlling the length of the two actuators, 3012A and 3012B, will control the tilt and height of the treadmill 3014 surface. In one embodiment, the actuators may be controlled such that the treadmill is angled or vertically displaced without angle depending on the height of the user. In one embodiment, the user may input their height in a controller and the controller may adjust the control algorithm around this specific starting height. The actuators may be connected at pinned or ball joints to provide for rotation as they extend their length and move one portion of the structure relative to the other. This system can provide simplicity, can require less precision, and utilizes minimal framing and actuators.

FIG. 30C illustrates another embodiment of a lift mechanism 3020 for a differential air pressure system. In the embodiment of FIG. 30C, lift mechanism 3020 includes four lead screw or linear actuators 3022, where each screw or actuator is attached to a corner of the treadmill 3024 (or other exercise machine or exercise platform). In another embodiment, the screws or actuators are attached to a floor (not shown). In some variations, the lead screws or actuators 3022 may be controlled simultaneously or independently to create any manner of tilt, forward/backward, left/right, and height of the treadmill. Variable adjustment enables user performance of many different exercises with an angled surface. In one embodiment, where side tilting is to be performed, a spherical joint can be provided on each corner.

Another embodiment (not shown) of lifting a treadmill or other exercise machine may comprise placing one air bags under each of the front and the rear of the treadmill (or other exercise machine or exercise platform), and controlling the pressure inside each air bag. Air used to pressurize the air bags may even be routed into the chamber after it goes through the air bags. Air bags may be constrained or made like a bellows so that inflation causes primarily vertical motion. The amount of pressure in a bellow can determine the vertical position of the bellows. As the bellows expands, the pressure will drop and load is reduced until equilibrium is reached. Then additional pressure will raise the height and reduction of pressure will lower the height.

As discussed herein, an exercise machine (e.g., treadmill, stepper, elliptical, bicycle, etc.) may be utilized in a differential air pressure system. Furthermore, the differential air pressure system may be adjusted for various users, the exercise machine may be adjusted to provide for various workout environments, and the differential air pressure system enclosure, opening, and structure may be configured in many different ways. The wide range of adjustments and system configurations therefore provides for a variety of workout, therapy, and/or medical treatment environments heretofore not realized in differential air pressure systems.

Bag Shaping for a Differential Air Pressure System

While a user is enclosed in a differential air pressure system chamber at a portion of their body near the torso, such as those described herein, it may occur that the user would hit a part of their body on the chamber shell during exercise. However, a user may wish to exercise or move in some cases without this inhibition of movement. This issue of movement inhibition is further exacerbated by the reality that users of many different body shapes and sizes will be using the same physical device. For instance, a rotund individual will require a wide opening and upper surface of the shell to fit inside. If left alone, this same surface, when used by a diminutive person will cause the small person's arms and hands to contact the upper surface because natural motion is to swing the arms by the hips.

Furthermore, the enclosure should be contoured to be long to allow the user to extend their leg back during running and bring the knee high during the forward step portion of the gait cycle. This creates a long device, which must at the same time remain narrow to prevent interference with arm swing. Should a user contact the shell during a run, such contact may throw off the user's balance or cause trauma to the area that impacted the enclosure. To enhance the safety of the system it may be desirable to contour the shape of the shell to avoid contact with the user's body as much as possible.

As discussed herein, a differential air pressure system shell can be contoured to allow for freedom of movement of all limbs of the body during user activity. Furthermore, a differential air pressure system is made adjustable to accommodate individuals of different sizes to use a single differential air pressure system apparatus and accommodate a range of varying body types.

Figure 31A:
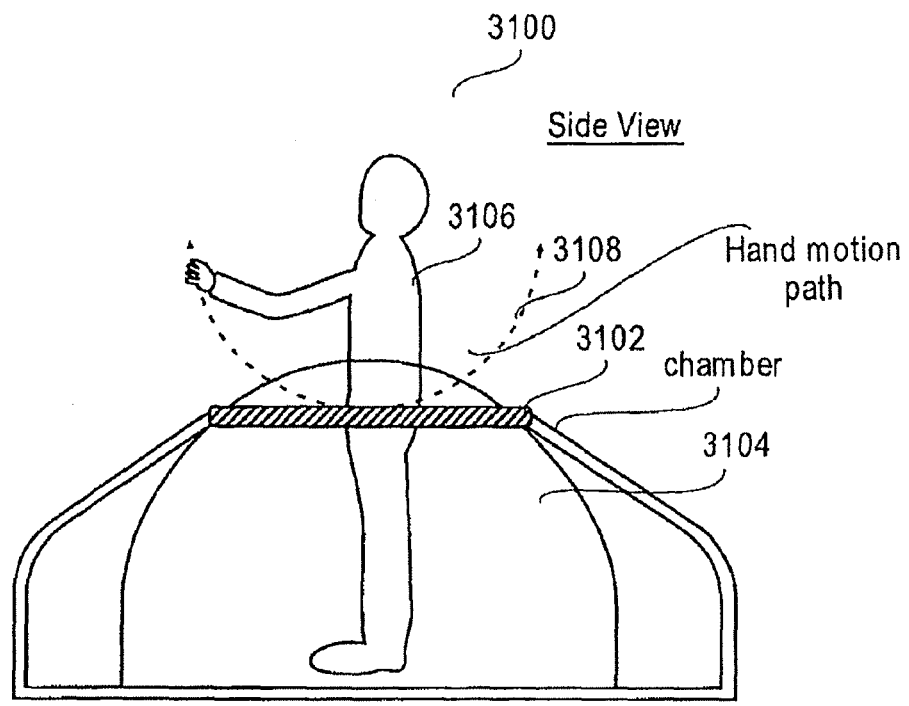
Figure 31B:
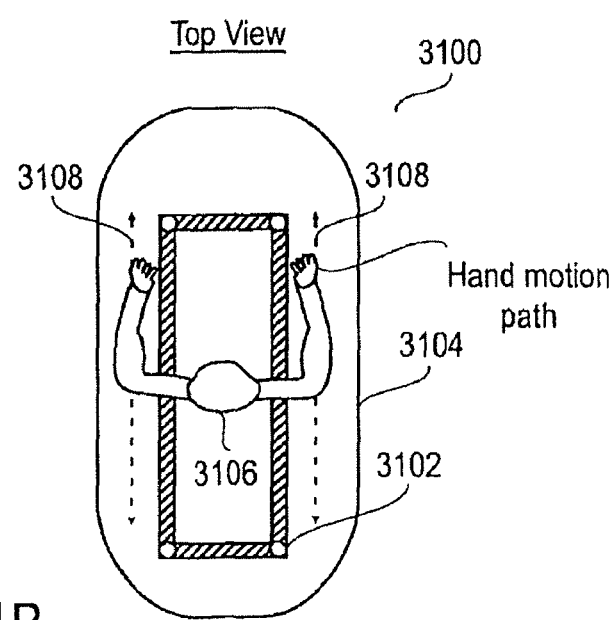

FIG. 31A illustrates a side view of one embodiment of a structural bar which contours and constrains a flexible inflatable shell in a differential air pressure system. FIG. 31B illustrates a top view of the structural bar. The differential air pressure system 3100 comprises a structural bar 3102 that contours and constrains a flexible inflatable shell 3104. The bar 3102 is formed in a shape around the user's 3106 waist such that the bar holds the fabric of the shell 3104 low and narrow on the side of the user to allow for freedom of arm and hand movement 3108. In one embodiment, the bar is configured to provide comfort in a system designed for walking or slow jogging.

Figure 31C:
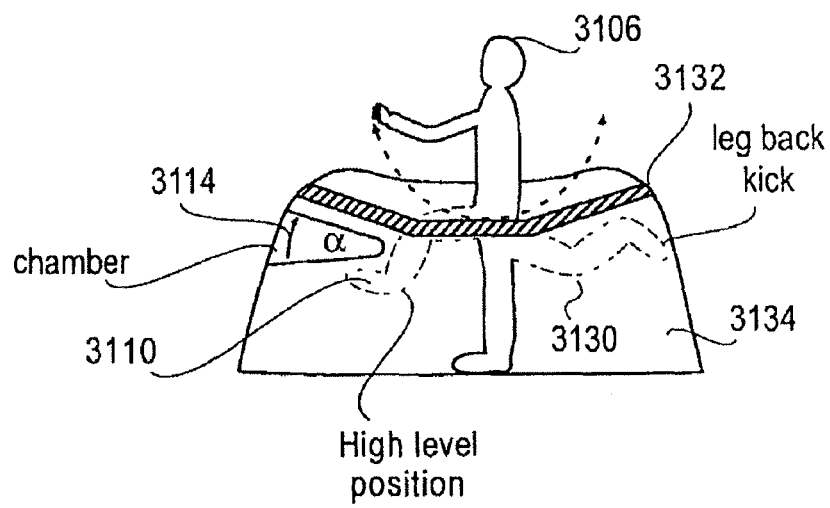
Figure 31D:
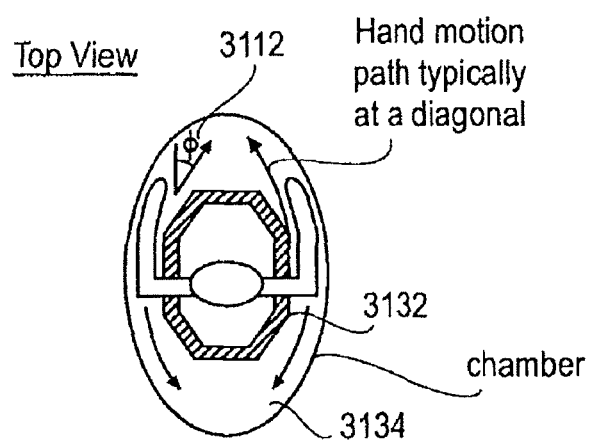

FIG. 31C illustrates a side view of another embodiment of a structural 3132 bar that contours and constrains a flexible inflatable shell in a differential air pressure system. FIG. 3D illustrates a top view of the structural bar 3132 of FIG. 31C. In the embodiments illustrated in FIGS. 31C and 31D, the bar 3132 may also be contoured upwards at an angle 3114 .alpha. in the front and the rear to accommodate a knee raising motion 3110 and/or a heel kick motion 3130 typically seen in faster running speeds. This more complex shape may be described as a saddle shape. In one embodiment, the structural material used in the shell 3134 has a significant strength and stiffness so as to not deform as the shell is pressurized and the shell tries to form a spherical shape to reduce wall stresses. In the top view of the structural bar, illustrated in FIG. 31D, the structural bar 3132 may be slanted in at the front and back at an angle 3112 .phi. In one embodiment, angle 3112 is consistent with the average angle of arm swing of a runner or person performing exercise. In one embodiment, the angles .alpha. and .phi. are adjustable with a series of telescoping and hinged tube pieces.

FIG. 31E illustrates one embodiment of a structural bar 3140 with adjustable angles and adjustable contour. In this particular embodiment, the width of the bar 3146 may be adjustable with telescoping bars or another sliding mechanism that allows length change while maintaining its structural integrity. Other configurations or adjustment mechanisms may also be utilized.

As illustrated in FIG. 31C, the front and back of structural bar 3102 may be substantially higher than the sides of the bar 3102, which reside lower on the user's 3106 body relative to the front and back to accommodate arm and hand movement. The height in the front and back of the bar allows for freedom of movement by the knees in the forward portion of the running gait and the height in the bag allows for heel kick without contacting the structure, which is a motion commonly seen in distance runners. The low side portion of the bar 3102 provides for arm swing of the individual.

The features discussed above with respect to shell height adjustment, rotational seals, translational seals, shell contour adjustment, etc. are all aimed at ensuring that an experience is provided that is as natural to normal exercise as possible. If the user must adjust their arm swing or position this may distort their gait and cause discomfort. Gait distortion and arm swing adjustment issues may be exacerbated in a sprinting situation versus a walking or jogging situation, but a user who feels awkward or self-conscious about contacting the shell will likely never feel completely natural. The embodiments discussed above may be used with a chamber constructed of fabric or a hybrid-type shell comprising a minimally deforming stiffer material as a lower portion with a flexible (e.g. fabric) top portion.

In one embodiment, a support bar is attached to the chamber in such a way that the fabric of the chamber contoured by the bar is restricted from moving past the bar, thus fixing the top shape of the fabric above the bar. To be implemented for users of different heights, the fabric below the bar is allowed to collapse or expand and deform to accommodate users of various heights. The bar can be secured in a vertical position with a locking or latching mechanism so as to maintain an appropriate height to match the individual who is exercising, such as illustrated in FIG. 11. The height of the bar may in some variations be dynamically controlled during a walking or running motion to maintain position throughout the gait cycle relative to the body.

In one embodiment, the contouring bar concept may be integrated into a minimally deforming shell enclosure. FIG. 32A illustrates one embodiment of a contoured top structure for a differential air pressure system. In that particular embodiment, system 3200 comprises an enclosure 3208. The top portion 3202 of the enclosure is molded or formed to provide a basic shape including a contour that is narrow and low by the user's hip, or more complex saddle shape, e.g. as produced by the bars in FIG. 31A-31E. The minimally deforming top shell portion 3202 may be part of a minimally deforming enclosure, or may be the top portion of the chamber that surrounds the user's 3204 waist and is attached to a lower fabric portion 3208 of the chamber in a substantially airtight manner. In one embodiment, vertical adjustment of the minimally deforming upper portion 3202 is allowed while maintaining the shape of the shell that is likely to be contacted by the user during motion. This upper portion 3202 may be formed from any structurally sound material such as plastic or fiberglass. In one embodiment, lightweight material is utilized since a user may have to lift the upper portion if it is not part of a fully rigid shell. In one embodiment, height adjustment may be provided by straps 3206, however, other forms of height adjustment described herein may be utilized to adjust and fix the height of upper portion 3202.

FIG. 32B illustrates a top view of a top portion of another embodiment of a minimally deforming shell enclosure. In this particular embodiment, a shell of a differential air pressure system is made fully of a minimally deforming material and has a contoured top portion 3211. As indicated by hinges (not shown), the top portion 3211 of the shell may be part of a door or clamshell style attachment to allow the user access into the shell without having to climb into the unit. In this embodiment, a locking mechanism 3212, such as a pin or clasp, is used to maintain the structural integrity and prevent deformation or separation of the clamshell or door halves under pressure.

FIGS. 32C and 32D illustrate additional embodiments of a minimally deforming top for a chamber (shell) of a differential air pressure system. In one embodiment, minimally deforming top 3222 may also be used as an attachment to a fabric portion of the shell. In this particular embodiment, a user may select a top 3222 and connect the selected top 3222 to a portion of a fabric shell 3224A, or a surrounding structure after they are secured into the chamber. Subsequently, the user can allow the deflated shell 3224A to inflate to form inflated shell 3224B underneath this minimally deforming shell top 3222 and, in some cases, to bubble up around the edges of the top 3222. The contoured configuration of shell top 3222 enables user freedom of movement similar to that discussed above.

Figure 33:
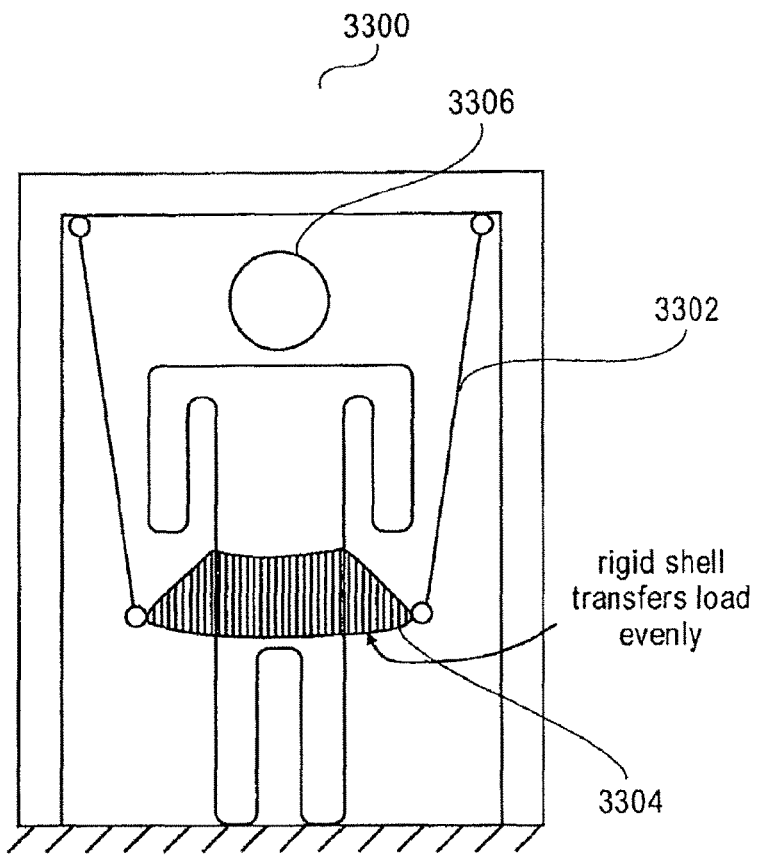
FIG. 33 illustrates one embodiment of a minimally deforming portion of a shell for use in an unloading device.
Figure 34:
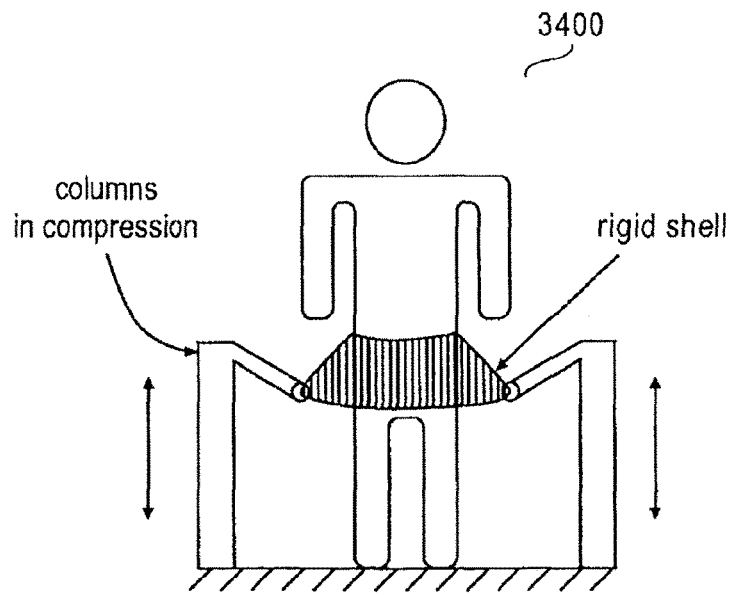
FIG. 34 illustrates one embodiment of a compression tension system for use with a minimally deforming portion of a shell.

FIG. 33 illustrates one embodiment of a minimally deforming portion of a shell for use in a traditional unloading device. In one embodiment, the unloading system is a harness system, where the lifting cabling or members 3302 are attached to the edges of the minimally deforming contoured shell 3304, thereby leaving an area around the user 3306 free of cables or other structural members that they may come into contact with. FIG. 34 illustrates one embodiment of a compression and tension system for use with a minimally deforming portion of a shell, similar to that discussed above with respect to FIG. 33.

Figure 35:
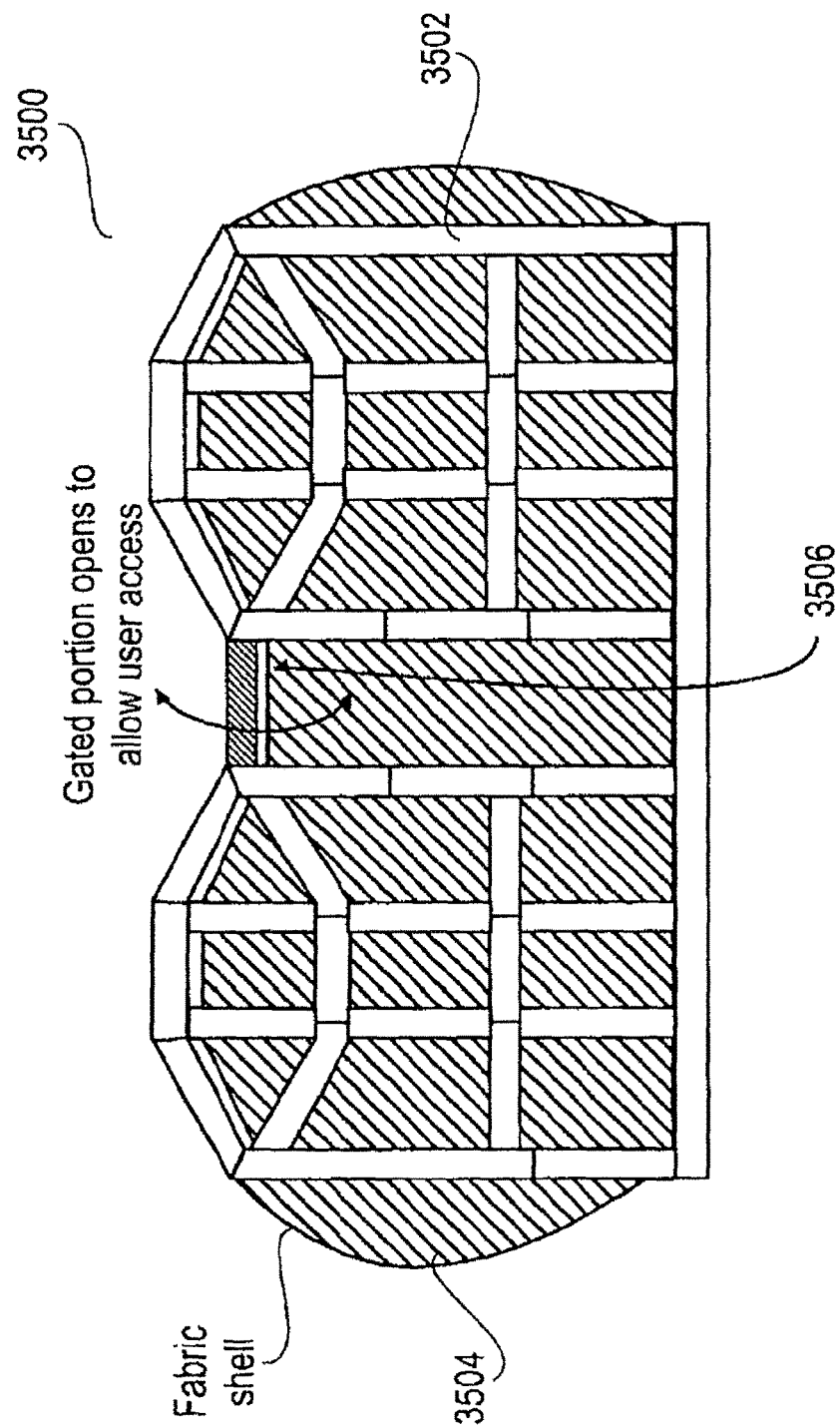
FIG. 35 illustrates one embodiment of a skeleton structure for constraining and shaping a flexible differential air pressure system enclosure.

In one embodiment, a structure, such as an endoskeleton or exoskeleton, may be utilized to constrain a fabric enclosure of a differential air pressure system. FIG. 35 illustrates one embodiment of a skeleton structure 3500 for constraining and shaping a fabric differential air pressure system enclosure. In this particular embodiment, when shell 3504 is inflated, skeleton 3502 constrains the shell 3504 to the shape of skeleton 3504. In one embodiment, exoskeleton or endoskeleton 3502 is constructed of connected lightweight structural support members to form the basic shell shape of an enclosure. The members may for example be welded together, connected via pipe joints as in ABS pipe couplings, or connected via sleeves. As discussed herein, an endoskeleton is a structure considered to be inside the shell enclosure, whereas an exoskeleton is considered to be outside of the enclosure.

A skeleton design is similar to a minimally deforming shell, discussed above, though reduces weight, fabrication costs, and potentially ingress and egress to the chamber by including a bar which acts as a gate 3506 to control user access to the chamber. In one embodiment, bar 3506 is placed to constrain the fabric 3504 shell from expanding outward and interfering with arm swing. In one embodiment, the upper portion and front and rear portions of the skeleton 3502 are contoured to provide a comparable shape described above to allow freedom of movement of user limbs during use. An exemplary construction may be a geodesic dome. In one embodiment, the skeleton 3502 may be vertically adjustable, and certain members of the skeleton 3502 may serve as hand rails.

Figure 36C:
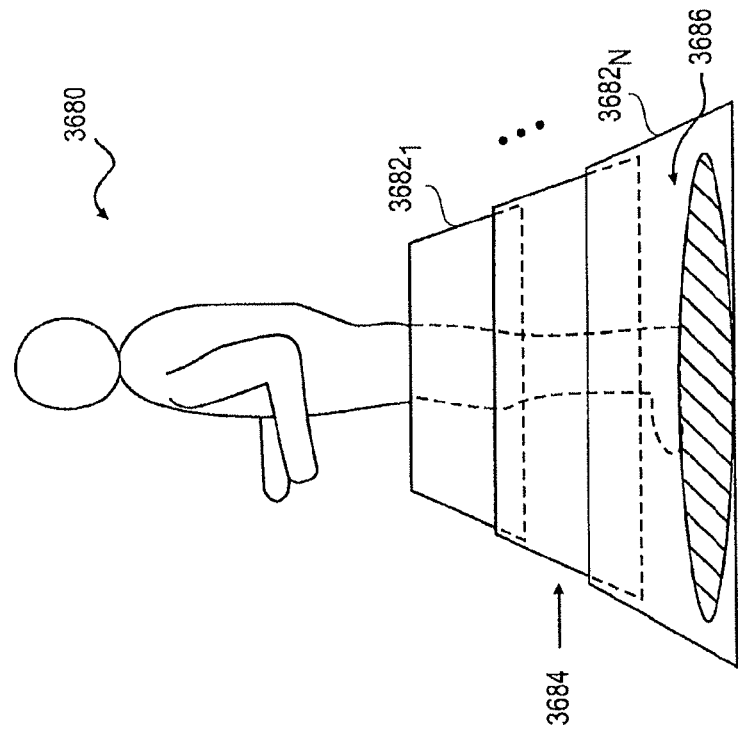
FIG. 36C illustrates one embodiment of a collapsible structure in a differential air pressure system.
Figure 36A:
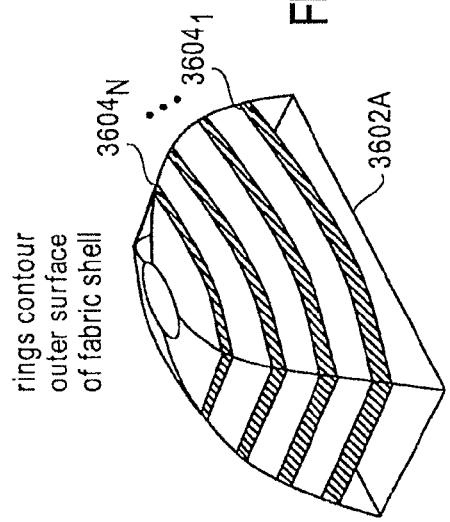
FIGS. 36A-36B illustrate various embodiments of a collapsible bag shaping mechanism in a differential air pressure system.
Figure 36B:
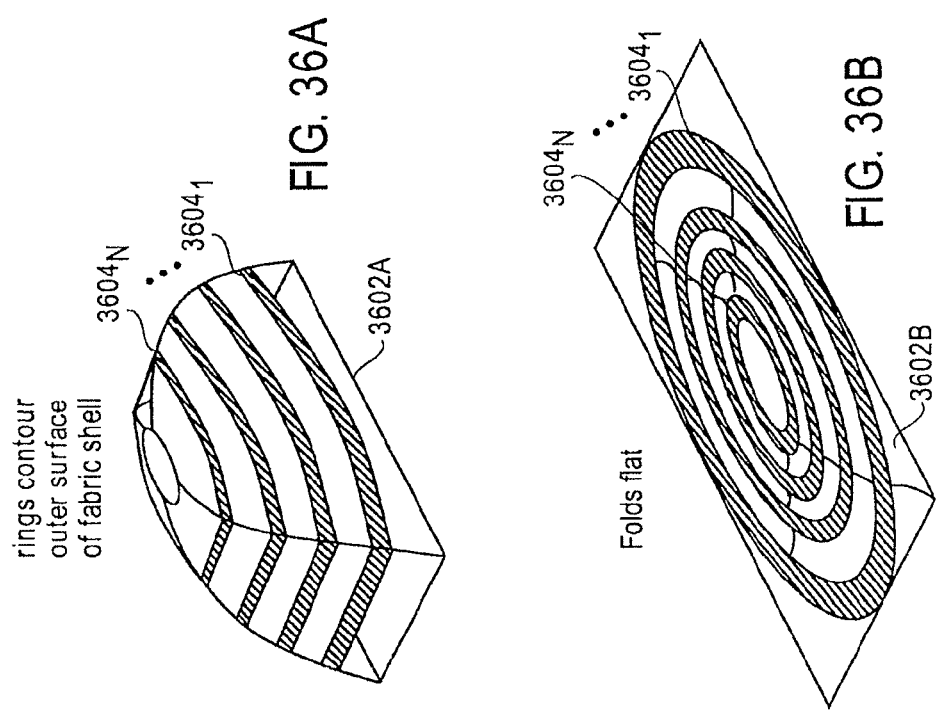

FIGS. 36A and 36B illustrate another embodiment for constraining and shaping a differential air pressure system bag. In one embodiment, to ensure that bag 3602A remains narrow along the user's sides but still allows for length of the bag and height in the front and back, one or more nested stays or one or more nested minimally deforming rings, such as rings $3604_1$ to $3604_N$, surround the shell, e.g. like a Japanese lantern. The series of minimally deforming rings surrounding the flexible (e.g. fabric) bag allows the fabric between stays or rings in configuration 3602A to collapse to form configuration 3602B when the bag is deflated.

In one embodiment, rings $3604_1$ to $3604_N$ are shaped approximately concentrically to allow deflation of bag 3602 in an organized fashion, rather than to freely crumple. Configuring rings in this fashion can further assist in controlling the shape of the fabric in a deflated state 3602B to make storage cleaner, as well as easier for a user walk over the deflated bag without tripping on a wrinkle or fold.

In one embodiment, instead of nested rings, one or more nested rigid structures may be utilized, as illustrated in FIG. 36C. Sections of plastic $3682_1$ to $3682_N$, or other rigid material, may be expanded to interfere with one another and form pyramid style structure 3684. When expanded, the nested rigid structures $3682_1 \ldots 3682_N$ contact one another and extend vertically to form a chamber 3686. The rigid pieces may in some variations have seals disposed between each layer (not shown) to create a sufficiently airtight environment inside the chamber 3686.

Figure 37:
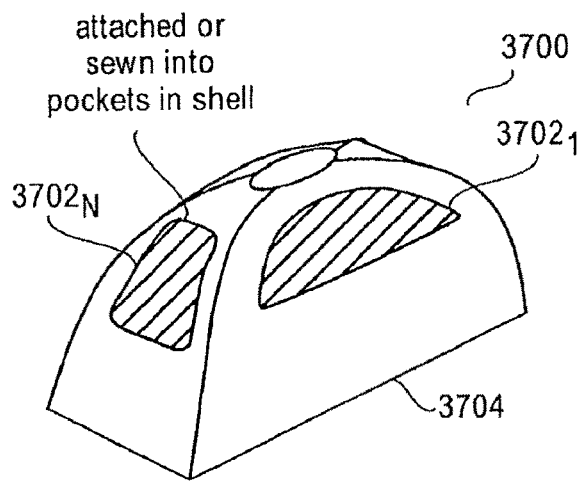
FIG. 37 illustrates an embodiment of a differential air pressure system comprising a contoured soft shell enclosure.

FIG. 37 illustrates an additional embodiment of a contoured soft enclosure in a differential air pressure system. In this particular embodiment, one or more minimally deforming shell portions, such as shell portions $3702_1$ to $3702_N$, are attached to the enclosure 3704 to cause the enclosure to conform to the shape of the minimally deforming shell portion or portions when inflated. In some variations, there can be multiple shell portions of various sizes located on the enclosure 3704. The shell portions may be affixed to the enclosure by any suitable attachment technique or means, e.g. sewn into pockets, or glued to the enclosure as non-limiting examples. The shell portions can in some circumstances provide local rigidity and structure to the enclosure 3704 without the bulk or weight of a fully hard shell forming the chamber for the user.

Figure 38:
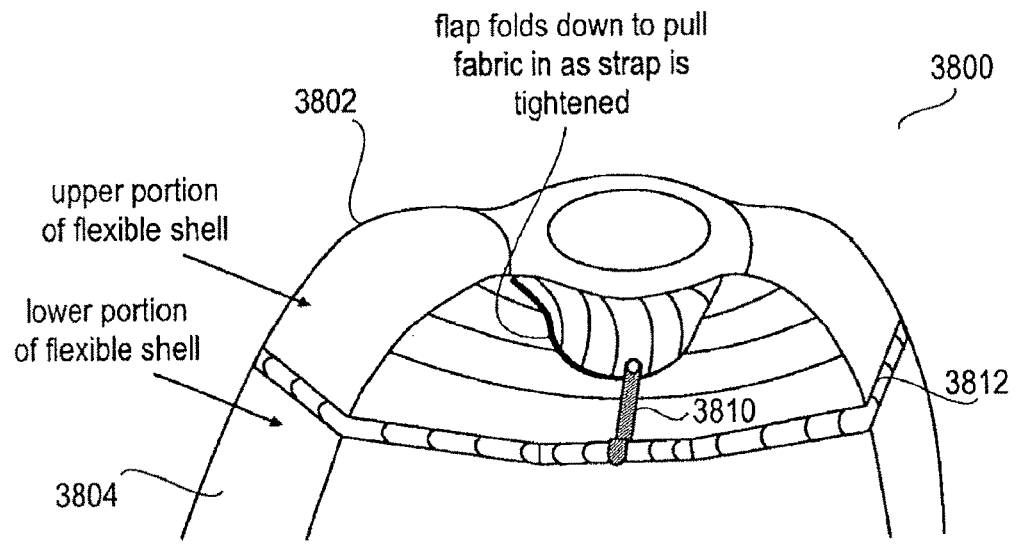
FIG. 38 illustrates an additional embodiment of a differential air pressure system comprising a contoured soft shell enclosure.

FIG. 38 illustrates yet an additional embodiment of a contoured soft shell enclosure in a differential air pressure system. In this particular embodiment, straps 3810 and contouring bar 3812 may be affixed to a portion of the enclosure 3802 such that when the straps are cinched down, the straps constrain a portion of the flexible (e.g. fabric) enclosure from expanding under pressure. In one embodiment, such straps may be placed in multiple positions (in addition to those illustrated) and may reside on any portion of the enclosure (different from those illustrated) that the user occupies during exercise. In one embodiment, the straps 3810 can be permanently attached to a differential air pressure system enclosure. In another embodiment, can be affixed to a separable portion of the differential air pressure system enclosure, e.g. a user seal, and may be affixed to a main portion of the enclosure to complete the enclosure.

As discussed above, the surface of hard and soft shell differential air pressure system cases may be contoured. The contouring allows for a wide degree of freedom of movement, which is as natural as possible, during exercise or therapy. Furthermore, as discussed above, the contouring may be easily adjusted during use by a user, a trainer, or therapist observing a routine, and the height of the contouring surface may also be adjustable by any method described herein or otherwise known. Optionally, the contouring method described above may be combined with any of the other inventions disclosed herein to promote freedom of movement and/or user ergonomics among other things.

Differential Air Pressure System Application

As discussed above, a differential air pressure system is described that is adjustable for users of different heights and body sizes. Furthermore, support systems and mechanisms are described that enable the differential air pressure systems to operate at different angles, speeds, etc. while the user is comfortable and safe, as well as allowing for a wide range of user motion. Embodiments of applications and uses for the differential air pressure system, such as any of systems described herein (e.g. in connection with FIG. 1 or FIG. 2), are described below.

Currently, obesity is driving people to become bedridden. As a person becomes increasingly obese, that person may not able to support his own weight or may not have the strength to sustain prolonged walking or jogging. Furthermore, such a person's joints may not be able to endure the stress of walking or other movement due to the excessive weight placed on the joints. As a consequence, obese people exercise less, and the downward cycle continues. One option open to obese people is to exercise in a pool. However, frequently obese people are embarrassed to enter pools and in some circumstances may require a hoist or other cumbersome means to actually enter the water. There is also risk of drowning with someone who is not fit. Walking and jogging are better forms of exercise for losing weight than aquatic exercise, or hand bikes, because of the rate of calorie burn. No practical harness systems are available for obese people, as these systems would be very uncomfortable because of the amount of weight the strapping would have to support, and the strapping may begin to cut into the skin. Strapping would also require significant setup time and multiple people to assist in getting the person into the machine.

Some embodiments of differential air pressure systems, which may be configured (or specifically designed) for wider persons, can allow for much simpler ingress and egress than aquatic exercise or harness systems, and the air pressure can provide a significant amount of weight support. Although an application of a differential air pressure system is described below for treatment of obesity, other maladies, such as, conditions that affect a person's motor system (e.g., multiple sclerosis, cerebral palsy, or Down Syndrome) or a person's exercise tolerance (e.g., cardiac disease, etc.) may also utilize the techniques described below.

Figure 39:
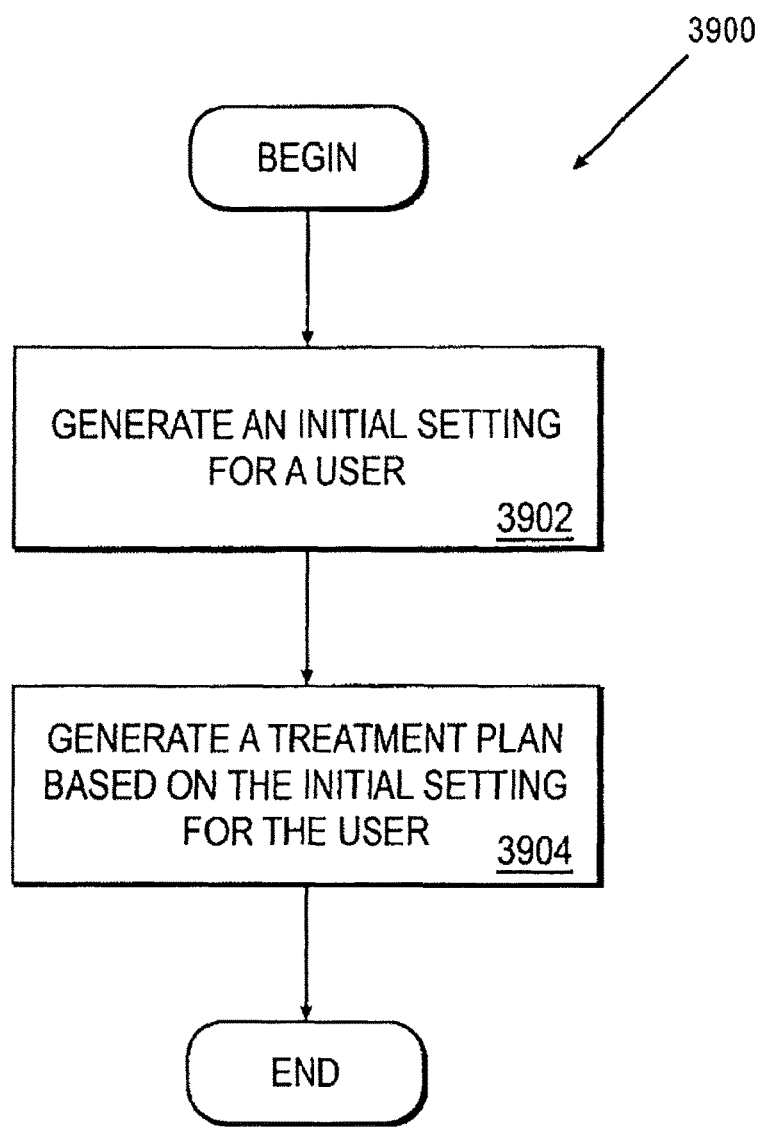
FIG. 39 is a flow diagram of one embodiment of a process for applying a differential air pressure system for treatment of obesity

FIG. 39 is a flow diagram of one embodiment of a process 3900 for applying a differential air pressure system to treat a condition, e.g. obesity, cardiac disease, multiple sclerosis, cerebral palsy, or Down Syndrome. The process is performed by processing logic that may comprise hardware (circuitry, dedicated logic, etc.), software (such as is run on a general purpose computer system or a dedicated machine), or a combination of both. In one embodiment, processor processing logic resides in processor 122 of FIG. 1 or processor 208 of FIG. 2.

Referring now to FIG. 39, the process begins by processing logic generating an initial setting for a user (processing block 3902). In one embodiment, the initial settings are for a user with obesity, though other maladies or conditions may be treated as described herein. This initial user setting may be based on a diagnostic value, such as a heart rate, perceived exertion, pain, a doctor's recommendation, therapist's treatment plan, etc. The initial setting may further be based on setting selected by a physical trainer, nutritionist, or other health professional. There are many choices and sources for initial settings.

Processing logic then develops a treatment plan based on the initial settings for the user (processing block 3904). A plan to combat obesity may include incrementally and systematically increasing the strenuousness of a workout by adjusting pressure in the chamber, adjusting incline of a treadmill, including intervals of strenuous and non-strenuous activity in a workout, etc., or any combination thereof. Additionally, processing logic may track user progress over time, or from session to session, to monitor weight loss or physical conditional of the user. Further, the treatment plan may be adjusted, either by processing logic, the user, an outside observer, a health professional, etc., to constantly improve the effectiveness of the treatment plan. By precisely controlling the forces against which the user is training using the differential air pressure systems and methods described herein, a precisely-controlled and quantifiable plan for weight loss with concomitant building of muscular strength and cardiovascular fitness may allow for an aggressive treatment plan of weight loss. Further, the differential air pressure systems can be somewhat self-adjusting for a user with obesity. For example, a treatment program may be designed so that a user exercises at a certain fraction of his body weight, so as the user loses weight, the pressure in the chamber may automatically drop to keep the user exercising at that same fraction of his new, lower body weight. This is important because weight loss drastically affects how a user can exercise. This allows, for example, the system to be more aggressive in treating obesity. The system may consist of periodic recalibration as weight is dropped and the user's bodyweight begins to change. By expanding this to record calibrations over a period of multiple workouts, weight loss of the user can be obtained. The weight loss can then affect other workout metrics such as speed, incline, etc. A composite of these metrics can give tangible feedback about the progress the user is making and make suggestions for workout adjustments to help the user more aggressively lose weight, regain mobility, improve cardiovascular fitness, etc. As a result, a consistent and safe workout is provided by the differential air pressure system, for a person suffering from obesity.

Calibration of a Differential Air Pressure System Via Pain Titration

Pain is a useful workout metric, especially for people rehabilitating an injury. In one embodiment, pain titration is utilized in an unloading device, such as the differential air pressure systems discussed herein, to record, adjust, and plan workouts. This can be beneficial by allowing a physician to create consistent workouts for patients, as well as storing and providing hard analytical data for evaluation of a patient's recovery process or injury. Furthermore, use of a differential air pressure system can also allow users to more quickly begin and complete a workout because their pain can be accurately and immediately controlled, without reliance on a physician or other health professional.

As discussed below, pain values may be measured or estimated using an arbitrary scale, from a knob, a numerical input, a graphical input, a series of questions, or other segmented scale method for accepting input from a user. Any of the above-listed pain level inputs that can be provided by the user can be used to evaluate the level of pain the user feels at one or more moments in a workout or therapy session, as well as to adjust metrics associated with a workout (i.e., maintaining a constant pain level).

Furthermore, user pain level inputs can be used to adjust a workout during a workout or therapy session. This allows adjustment of workouts (current and future) based on user input. In some embodiments, pain level inputs from the user can be used to create one or more protocols that, in turn, create a workout or series of workouts based on the user's pain level. The creation of one or more protocols corresponding to workout settings can allows users, physicians, and other health professionals to obtain consistent metrics of healing, either from a set different workouts by a single user, or by workouts across multiple users normalized to a generic pain scale. Furthermore, by storing or otherwise outputting pain metrics, a user can monitor how he has progressed, and a physician or other health professional can monitor how his patient is progressing, and in some cases may compare his patient's progress versus statistics of healing from people with similar injuries or conditions. This type of data collection for a single individual or across groups of individual can enable further refinement of workouts to assist in the healing process.

The workouts can be designed for recovery from a new injury, or for managing a chronic injury or condition. A workout designed to push ability and to heal a temporary injury is generally different than providing a workout regimen for someone with a chronic injury. For example, a protocol for increasing load on a person recovering from a stress fracture is likely to be different than a protocol to assist someone with arthritis exercise, because a health professional may expect a certain rate of healing to reach full health for an acute stress fracture injury versus a slower progression, stagnant performance, or even declining performance with a chronic injury or degenerative condition.

In some embodiments, pain inputs and/or pain level readings can be used to predict a rate of healing. Such a correlation may allow a user or physician to predict what activities are most appropriate to allow or restrict activity at certain points in the recovery cycle. The pain inputs and a predicted rate of healing associated with the pain inputs can be used to predict when the patient will be able to return to normal or safe use of the injured body part (e.g., use of the body part not previously allowed due to the injury). This capability may be useful, for example, in cases of injured athletes trying to decide when they can resume competition. The capability has other uses beyond that of athletes. For example, the pain inputs and a predicted rate of healing associated with the pain inputs can be applied to work-related injuries and the ability and/or timing of a user to resume work activity. In the case of athletes or workers deciding whether to resume their normal activities, or a health professional deciding on a course of treatment, the systematic pain data that can in some circumstances be obtained using a differential air pressure system may provide a more quantitative basis for making such decisions.

Furthermore, in some variations, pain inputs/readings can be used as a diagnostic tool to determine the source of an injury. Physicians often use manual stimulation to determine the site of pain. This system can allow for a user to change variables in a workout in a controlled manner and to have a protocol for a recovery workout, and the resulting pain input from the user may reveal a more specific description of the condition for a physician or other health professional. The pain inputs can further be used to evaluate the extent of an injury. The extent of an injury can be estimated by pain during manual stimulation or through scanning (x-ray, MRI, CAT, etc). Differential air pressure systems that are configured to receive pain input from a user can allow for the user to change workout constants such as, but not limited to, speed, incline, and effective bodyweight to identify the acceptable load on the injury. The system may record the progression and different pain levels for a given set of functional system parameters, and a protocol developed based on the level of pain at multiple points of adjustment. Optionally, these data may be output to a physician or other health professional for creation of a new, separate protocol or for adjustment of a system generated protocol.

In some embodiments, the user pain input may be provided to a sensor of a differential air pressure system, for example a sensor that senses a biological parameter of the user, e.g. swelling, blood pressure, muscle effort, tissue strain, blood flow, brain activity, etc., or any combination thereof. These extra sensors may, but do not have to be, directly connected to the user. In these configurations, the system may utilize other external factors that have been linked to pain in lieu of or in addition to direct pain readings from the user to manage and modify a workout. The sensors can be, but are not limited to, mechanical or electrical sensors.

The pain inputs, workout determination, injury evaluation, and/or calibration can take place individually or in conjunction with one another, and take place in hardware, software, or both hardware and software. The software may reside on the machine itself or on an external computer or evaluation center. The data may be transferred from the machine by a memory storage device or transmitted over a network, e.g. a wireless network.

Because different conditions may require different programs and settings for a differential air pressure system, the system can be calibrated. In some variations, the system calibration is performed based on a condition, personal factors of a user, malady, etc. For example, a person with a torn anterior cruciate ligament (ACL) in his knee may not need the same initial settings in a differential air pressure system as a person suffering from obesity, or a child suffering from Down Syndrome.

Figure 40:
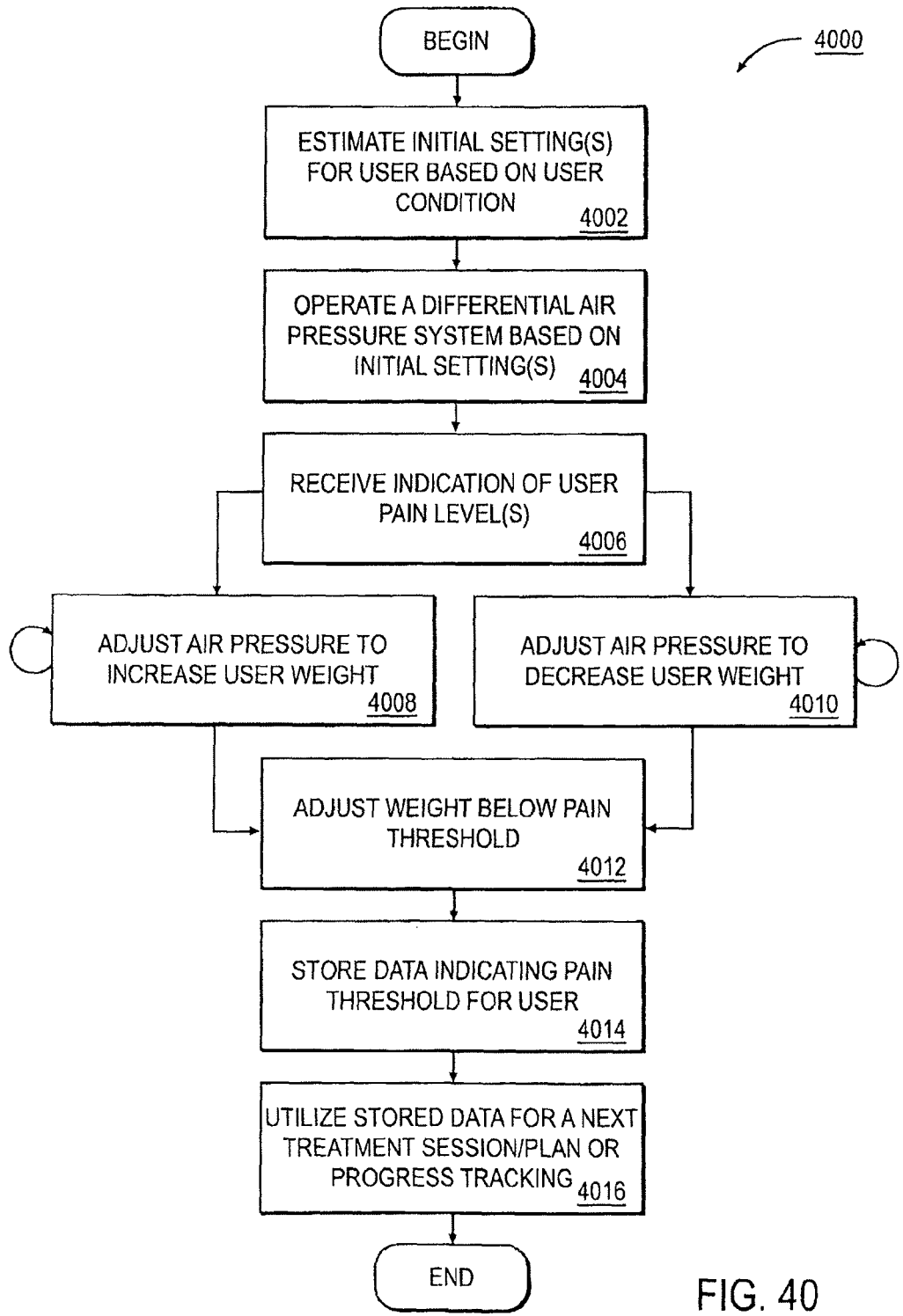
FIG. 40 is a flow diagram of one embodiment of a process for calibrating a differential air pressure device based on user pain levels.

FIG. 40 is a flow diagram of one embodiment of a process 4000 for calibrating the differential air pressure device based on user pain levels. The process is performed by processing logic that may comprise hardware (circuitry, dedicated logic, etc.), software (such as is run on a general purpose computer system or a dedicated machine), or a combination of both hardware and software. In one embodiment, processor processing logic resides in processor 122 of FIG. 1 or processor 208 of FIG. 2.

Referring to FIG. 40, the process begins by processing logic estimating initial settings for a user based on the user's condition (processing block 4002). In one embodiment, an educated guess as to how much pressure (e.g., a reduction in active body weight) may provide an initial setting. In some situations, the estimate is made to err on the side of caution given specific conditions. For example, for a user with a torn anterior cruciate ligament (ACL), processing logic may specify that the differential air pressure system should be configured to 30% of that user's body weight, while processing logic may specify 50% of a user's body weight in a pediatrics case.

Processing logic then operates a differential air pressure system according to the initial settings (processing block 4004).

Processing logic may further receive an indication of a user's pain level (processing block 4006). In various embodiments, a user may operate a user interface (which may be on a control panel 118), e.g. hit a button, turn a dial, speak, touch a screen or other touch sensor, etc. to indicate that they are in pain, or to indicate a level of pain that they are experiencing. In one embodiment, processing logic may receive data corresponding to a user's pain from an arbitrary user-actuated dial. For example, control panel 118 of a differential air pressure system may include a dial from 0-100 that corresponds to zero pressure and full pressure, respectively, and/or a scale of 0-10 for indicating the level of pain. This dial would control the pressure set point, so the first time a patient comes in the knob could be set to 80 (i.e., meaning 80% of full pressure, not full body weight) and system adjustment based on a pain level can be made thereafter. The position of the pressure dial and/or pain dial could be adjusted by processing logic in a future treatment.

Based on the received data indicating user pain, air pressure in the system is adjusted to either increase weight (processing block 4008) or decrease weight (processing block 4010). In some variations, if data are received that indicates a user feels pain or feels pain of a certain level, weight experienced by the user is reduced in small increments by increasing chamber pressure until data are received that indicates no more pain is felt or that pain is within a desired range. Furthermore, if a user indicates that no pain is felt, body weight experienced by the user may be increased by decreasing the chamber pressure until the user begin to feel the pain of his injury. Weight experienced by the user is then adjusted using pressure so that pain indicated by the user and/or sensed by one or more sensors as described above is below the known threshold (processing block 4012). In some variations of the method, pressure is adjusted so that the body weight percentage is reduced by a few percentage points per adjustment.

Processing logic stores data indicating this point (processing block 4014), e.g. a pressure at which the user starts to feel pain or a certain amount of pain. As a result, the stored data point (e.g., applied pressure as an indication of an effective body weight) may later be used by processing logic as a reference to start, increase, or decrease the chamber pressure the next time the user undergoes a treatment (processing block 4016). Furthermore, the data points may be stored and tracked over time to provide a relative progress of treatment.

In different embodiments, user pain readings can occur before, during, or after an unloading session. Because the pain readings can be taken at any time, or almost any time depending on the protocol used, the system has a chance not only to calibrate the user to workout at expected pain levels, but to also dynamically modify the calibration and/or workout at any point during the workout. The pain inputs can involve either static or dynamic forces which include, but are not limited to, ground reaction forces, weight, foot strike forces, torque, or combinations of those forces. Furthermore, calibration based on these forces or torques may allow for the physician (or other health professional) or the system to devise a workout targeted more directly to a specific injury. Some injuries are more prone to torque on a body part than direct ground forces and vice versa.

Pain titration is used in medicine to treat many maladies. The process and system described above may enable fine adjustment in conjunction with accurate and repeatable control for offloading user weight. Furthermore, an efficient method is provided for quantitatively accounting for and calibrating against a measure, pain, that is typically not quantifiable, or not quantified in practice. Furthermore, settings may be stored and tracked to further refine treatment programs, as well as to predict and proscribe future treatment, future device settings, etc. For example, if a user with an ankle injury is only able to perform a 45 minute first workout, but a 50 minute second workout, then a prediction of a future starting setting (e.g., a 55 minute workout) may be set and progress gauged.

In some variations of the embodiments described herein, there may be no need to know or measure an initial specific body weight or percentage of body weight as a function of pressure, because metrics such as pain threshold of a user are used to calibrate the system.

Exemplary Computer System

Figure 41:
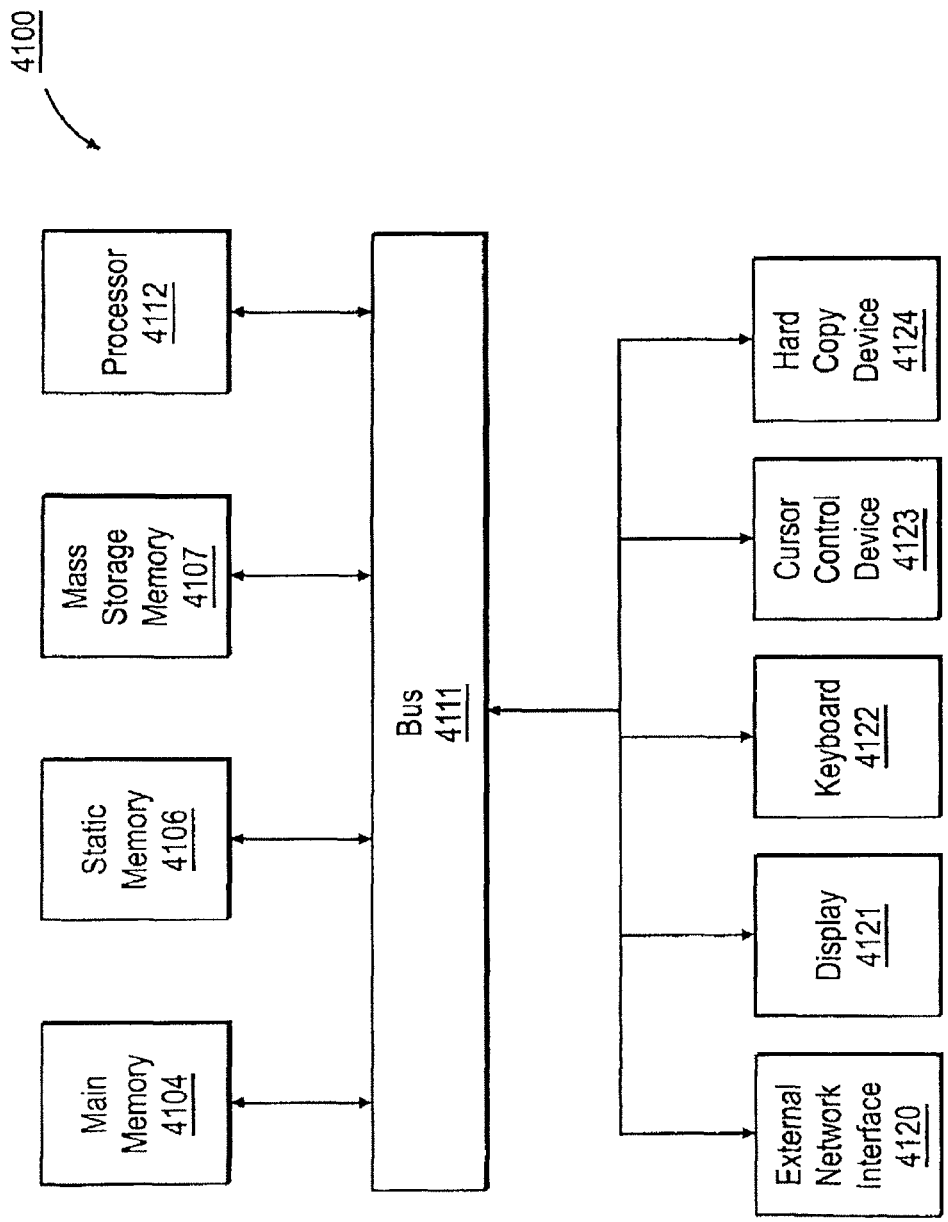
FIG. 41 is a block diagram of an exemplary computer system that may perform one or more of the operations described herein.

FIG. 41 is a block diagram of an exemplary computer system that may perform one or more of the operations described herein. Referring to FIG. 41, computer system 4100 may comprise an exemplary client or server computer system. Computer system 4100 comprises a communication mechanism or bus 4111 for communicating information, and a processor 4112 coupled with bus 4111 for processing information. Processor 4112 may in some variations be a microprocessor, but is not limited to a microprocessor.

System 4100 further comprises a random access memory (RAM), or other dynamic storage device 4104 (referred to as main memory) coupled to bus 4111 for storing information and instructions to be executed by processor 4112. Main memory 4104 also may be used for storing temporary variables or other intermediate information during execution of instructions by processor 4112.

Computer system 4100 also comprises a read only memory (ROM) and/or other static storage device 4106 coupled to bus 4111 for storing static information and instructions for processor 4112, and a data storage device 4107, such as a magnetic disk or optical disk and its corresponding disk drive. Data storage device 4107 is coupled to bus 4111 for storing information and instructions.

Computer system 4100 may further be coupled to a display device 4121, such as a cathode ray tube (CRT) or liquid crystal display (LCD), coupled to bus 4111 for displaying information to a computer user. An alphanumeric input device 4122, including alphanumeric and other keys, may also be coupled to bus 4111 for communicating information and command selections to processor 4112. An additional user input device is cursor control 4123, such as a mouse, trackball, trackpad, stylus, or cursor direction keys, coupled to bus 4111 for communicating direction information and command selections to processor 4112, and for controlling cursor movement on display 4121.

Another device that may be coupled to bus 4111 is hard copy device 4124, which may be used for marking information on a medium such as paper, film, or similar types of media. Another device that may be coupled to bus 4111 is a wired/wireless communication capability 4125 to communication to a phone or handheld palm device.

Note that any or all of the components of system 4100 and associated hardware may be used in the present invention. However, it can be appreciated that other configurations of the computer system may include some or all of the devices. Certain variations of system 4100 may include peripherals or components not illustrated in FIG. 41, e.g. components configured to receive different types of user input, such as audible input, or a touch sensor such as a touch screen.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

The digital processing device(s) described herein may include one or more general-purpose processing devices such as a microprocessor or central processing unit, a controller, or the like. Alternatively, the digital processing device may include one or more special-purpose processing devices such as a digital signal processor (DSP), an application specific integrated circuit (ASIC), a field programmable gate array (FPGA), or the like. In an alternative embodiment, for example, the digital processing device may be a network processor having multiple processors including a core unit and multiple microengines. Additionally, the digital processing device may include any combination of general-purpose processing device(s) and special-purpose processing device(s).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

While embodiments and applications of this invention have been shown and described, it would be apparent to those skilled in the art having the benefit of this disclosure that many more modifications than mentioned above are possible without departing from the inventive concepts herein. For example, the present invention may be applicable to containing any part of the body, such as the upper body, torso area, etc. The invention, therefore, is not to be restricted except in the spirit of the appended claims. Furthermore, embodiments of the systems, apparatuses, and methods described herein may be practiced individually, or in combination. Many different combinations would be apparent to those skilled in the art having the benefit of this disclosure.

It shall be understood that any of the concepts described herein may be joined together, or combined, to form a useful invention. For instance, an adjustable orifice may be combined with a contoured shell to provide an effective means for accepting uses or various body types and maintaining a natural running experience. For the sake of brevity, and to avoid obscuring the individual concepts discussed above, not all combinations of the inventions described herein have been listed, but combinations shall be held within the scope of this patent. Additionally, it shall be understood that systems that described a pressurized chamber may be construed to include both positive and negative pressure configurations. Positive versus negative pressure may require different configurations of the inventions but such modifications from those explicitly described herein shall be considered within the scope of this patent.

What is claimed is:

1. A structure for enclosing and sealing a portion of a body of a user into a differential air pressure system, the structure comprising:
    a chamber inflatable by a pressurizing system under control of a processor to at least partially unweight the user;
    a height adjustable structure having a plurality of height adjustment slots in a front of the chamber and a plurality of height adjustment slots in a rear of the chamber;
    a user seal coupled to the chamber, the user seal comprising an adjustable opening that is capable of receiving and sealing around the user's body so that at least a portion of the user's body is sealed into the chamber, wherein a sufficiently airtight junction is formed between the user's body and the chamber so that a nonzero differential pressure provided by the pressurizing system can be sustained in the chamber, and the adjustable opening in the chamber is capable of accommodating a range of user body sizes; and
    a support bar around the user seal having a front engagement member to couple to one height adjustment slot of the plurality of height adjustment slots in the front of the chamber and a rear engagement member to couple to one height adjustment slot of the plurality of height adjustment slots in the rear of the chamber.

2. The structure of claim 1 further comprising a treadmill within the chamber positioned for use by the user when sealed in the chamber by the user seal.

3. The structure of claim 2 wherein the support bar is contoured to accommodate for a movement associated with the use of the treadmill by the user coupled to the user seal.

4. The structure of claim 3 wherein the movement associated with the use of the treadmill is one of sprinting, running, jogging and walking.

5. The structure of claim 1 wherein when the support bar is coupled to one height adjustment slot in the front of the chamber and one height adjustment slot in the rear of the chamber the user seal is tilted.

6. The structure of claim 1 wherein a sleeve of the chamber connects the support bar attached to the chamber.

7. The structure of claim 1 wherein when the support bar is coupled to one height adjustment slot in the front of the chamber and one height adjustment slot in the rear of the chamber the user seal is adapted to a height and a tilt for the user coupled to the user seal.

8. The structure of claim 1 wherein the support bar is contoured to have a dip at or near a hip of the user when coupled to the user seal.

9. The structure of claim 1 further comprising a latching mechanism that transitions from an open position to a closed position, wherein when the latching mechanism is in the closed position the support bar is secured in place relative to the chamber.

10. The structure of claim 1 wherein the support bar is contoured to accommodate an arm swing motion of the user when coupled to the user seal.

11. The structure of claim 1 wherein the support bar is contoured to provide for the user, when coupled to the user seal, a lower portion at or near a hip of the user and a front raised portion and a rear raised portion to accommodate a leg kick and a high knee action of the user.

12. The structure of claim 1 wherein a perimeter shape of the support bar controls a perimeter shape of the chamber adjacent to the user seal.

13. The structure of claim 1 further comprising a locking bar to fix the support bar in place in a height adjustment slot in the front of the chamber and a locking bar to fix the support bar in place in a height adjustment slot in the rear of the chamber.

14. The structure of claim 1 wherein the support bar can support the weight of the user when coupled to the user seal without bending or breaking.

15. The structure of claim 1 wherein the plurality of height adjustment slots in the front of the chamber and the plurality of height adjustment slots in the rear of the chamber are configured as horizontal slots.

16. The structure of claim 1 wherein the plurality of height adjustment slots in the front of the chamber and the plurality of height adjustment slots in the rear of the chamber are configured as spring loaded cams.

17. The structure of claim 1 wherein the plurality of height adjustment slots in the front of the chamber and the plurality of height adjustment slots in the rear of the chamber are configured so that the support bar is locked into place when the chamber is under pressure.

18. The structure of claim 1 wherein the plurality of height adjustment slots in the front of the chamber and the plurality of height adjustment slots in the rear of the chamber further comprise a mechanical barrier such that the support bar is pushed past the mechanical barrier before being locking into a height adjustment slot.

19. The structure of claim 1 wherein the chamber is inflated by the pressurizing system under control of the processor in response to instructions provided to the processor indicating an initial setting by a user and a generated treatment plan.

20. The structure of claim 1 further comprising a touch screen adjacent to the chamber, within reach of the user when coupled to the user seal and in communication with the processor.

* * * * *